US012648811B2

(12) United States Patent
Mahmoudi et al.

(10) Patent No.: US 12,648,811 B2
(45) Date of Patent: Jun. 9, 2026

(54) PUNCTURE ELEMENTS FOR SHUNTING CATHETERS

(71) Applicant: THERAHEART INC., Irvine, CA (US)

(72) Inventors: Rani Abdullah Mahmoudi, Huntington Beach, CA (US); Wei Gan, Irvine, CA (US); Ajay Kumar Dass, Costa Mesa, CA (US)

(73) Assignee: Theraheart Inc., Irvine, CA (US)

( * ) Notice: Subject to any disclaimer, the term of this patent is extended or adjusted under 35 U.S.C. 154(b) by 0 days.

(21) Appl. No.: 18/766,903

(22) Filed: Jul. 9, 2024

(65) Prior Publication Data

US 2026/0013933 A1    Jan. 15, 2026

(51) Int. Cl.
  *A61B 18/14* (2006.01)
  *A61B 17/34* (2006.01)
  *A61B 18/00* (2006.01)
(52) U.S. Cl.
  CPC ...... *A61B 18/1492* (2013.01); *A61B 17/3415* (2013.01); *A61B 2017/3456* (2013.01); *A61B 2018/00351* (2013.01); *A61B 2018/00577* (2013.01)
(58) Field of Classification Search
  CPC .......... A61B 17/00234; A61B 17/3403; A61B 17/3415; A61B 17/3456; A61B 2017/00199; A61B 2017/00252; A61B 2017/00305; A61B 2017/00411; A61B 2017/00544; A61B 2017/00557; A61B 18/1492; A61B 2018/00351; A61B 2018/00577
  See application file for complete search history.

(56) References Cited

U.S. PATENT DOCUMENTS

| | | | |
|---|---|---|---|
| 4,861,336 | A | 8/1989 | Helzel |
| 5,255,679 | A | 10/1993 | Imran |
| 5,328,472 | A | 7/1994 | Rupp et al. |
| 5,800,450 | A | 9/1998 | Lary et al. |
| 6,179,832 | B1 | 1/2001 | Tartaglia et al. |
| 6,726,677 | B1 | 4/2004 | Flaherty et al. |

(Continued)

FOREIGN PATENT DOCUMENTS

| | | |
|---|---|---|
| CA | 2472701 C | 11/2012 |
| CN | 109965974 A | 7/2019 |

(Continued)

OTHER PUBLICATIONS

Babaliaros et al., "Emerging Applications for Transseptal Left Heart Catheterization: Old Techniques for New Procedures," J. Am. Coll..Cardiol., 2008; 51:2116-22.

(Continued)

*Primary Examiner* — Khadijeh A Vahdat
(74) *Attorney, Agent, or Firm* — Faegre Drinker Biddle & Reath LLP

(57) ABSTRACT

At least some embodiments of the present disclosure are directed to systems and methods for creating a shunt in a patient. In some embodiments, a shunting catheter includes: a catheter shaft having a distal end and a proximal end, the catheter shaft including a shaft lumen; a shunting component including one or more electrodes; and a puncture assembly disposed in the shaft lumen at a first state and extended from the catheter shaft at a second state.

21 Claims, 22 Drawing Sheets

(56) References Cited

U.S. PATENT DOCUMENTS

| | | | |
|---|---|---|---|
| 7,018,400 B2 | 3/2006 | Haarstad et al. |
| 7,150,745 B2 | 12/2006 | Stern et al. |
| 7,655,005 B2 | 2/2010 | Bhola |
| 7,674,256 B2 | 3/2010 | Marrouche et al. |
| 7,966,057 B2 | 6/2011 | Macaulay et al. |
| 8,021,359 B2 | 9/2011 | Auth et al. |
| 8,043,360 B2 | 10/2011 | McNamara et al. |
| 8,157,860 B2 | 4/2012 | McNamara et al. |
| 8,172,896 B2 | 5/2012 | McNamara et al. |
| 8,214,015 B2 | 7/2012 | Macaulay et al. |
| 8,226,619 B2 | 7/2012 | Smith et al. |
| 8,252,042 B2 | 8/2012 | McNamara et al. |
| 8,374,680 B2 | 2/2013 | Thompson |
| 8,585,596 B1 | 11/2013 | Flaherty et al. |
| 8,617,152 B2 | 12/2013 | Flaherty et al. |
| 8,728,073 B2 | 5/2014 | McDaniel |
| 8,758,363 B2 | 6/2014 | Nishtala et al. |
| 8,874,237 B2 | 10/2014 | Schilling |
| 8,882,697 B2 | 11/2014 | McNamara et al. |
| 8,900,250 B2 | 12/2014 | Fritscher-Ravens et al. |
| 8,926,602 B2 | 1/2015 | Pageard |
| 8,968,233 B2 | 3/2015 | Duffy et al. |
| 9,089,314 B2 | 7/2015 | Wittenberger |
| 9,345,858 B2 | 5/2016 | Flaherty et al. |
| 9,468,744 B2 | 10/2016 | Arana et al. |
| 9,642,993 B2 | 5/2017 | McNamara et al. |
| 9,789,294 B2 | 10/2017 | Taft et al. |
| 9,808,303 B2 | 11/2017 | Gelfand et al. |
| 9,808,304 B2 | 11/2017 | Lalonde |
| 9,814,483 B2 | 11/2017 | Vardi |
| 9,918,789 B2 | 3/2018 | Bagley et al. |
| 10,016,620 B2 | 7/2018 | Aljuri et al. |
| 10,039,905 B1 | 8/2018 | Taft et al. |
| 10,154,878 B2 | 12/2018 | Greenlaw et al. |
| 10,188,375 B2 | 1/2019 | McNamara et al. |
| 10,207,126 B2 | 2/2019 | Benson |
| 10,245,352 B2 | 4/2019 | Wilson et al. |
| 10,327,791 B2 | 6/2019 | Argentine et al. |
| 10,426,497 B2 | 10/2019 | Chou et al. |
| 10,449,339 B2 | 10/2019 | Wilson et al. |
| 10,568,688 B2 | 2/2020 | Hu et al. |
| 10,568,751 B2 | 2/2020 | McNamara |
| 10,624,621 B2 | 4/2020 | Celermajer |
| 10,639,060 B2 | 5/2020 | Vardi et al. |
| 10,722,300 B2 | 7/2020 | Gupta et al. |
| 10,729,492 B2 | 8/2020 | Brown et al. |
| 10,758,714 B2 | 9/2020 | Laby et al. |
| 10,842,562 B2 | 11/2020 | Zhang et al. |
| 10,857,328 B2 | 12/2020 | Walzman |
| 10,864,041 B2 | 12/2020 | Urbanski et al. |
| 10,932,723 B2 | 3/2021 | Eliason et al. |
| 10,980,552 B2 | 4/2021 | Mustapha |
| 10,987,494 B2 | 4/2021 | Skinner et al. |
| 10,993,735 B2 | 5/2021 | Vardi et al. |
| 10,993,736 B2 | 5/2021 | Vardi et al. |
| 11,052,246 B2 | 7/2021 | Stewart et al. |
| 11,065,019 B1 | 7/2021 | Chou et al. |
| 11,071,585 B2 | 7/2021 | Zhang et al. |
| 11,083,520 B2 | 8/2021 | Ghaly et al. |
| 11,135,410 B2 | 10/2021 | Finch et al. |
| 11,224,449 B2 | 1/2022 | Chou et al. |
| 11,224,450 B2 | 1/2022 | Chou et al. |
| 11,350,990 B2 | 6/2022 | Gupta et al. |
| 11,369,346 B2 | 6/2022 | Stigall et al. |
| 11,369,405 B2 | 6/2022 | Vardi et al. |
| 11,399,852 B2 | 8/2022 | Wilson et al. |
| 11,534,239 B2 | 12/2022 | Bishara et al. |
| 11,612,432 B2 | 3/2023 | Pate et al. |
| 11,648,042 B2 | 5/2023 | Kelley |
| 11,690,609 B2 | 7/2023 | Celermajer |
| 11,717,429 B2 | 8/2023 | Schwartz et al. |
| 11,752,314 B2 | 9/2023 | Taft et al. |
| 11,793,529 B2 | 10/2023 | Chou et al. |
| 11,806,032 B2 | 11/2023 | Chou et al. |
| 11,865,282 B2 | 1/2024 | Nae et al. |
| 11,957,374 B2 | 4/2024 | Vardi et al. |
| 12,004,802 B2 | 6/2024 | Scott et al. |
| 2005/0154386 A1 | 7/2005 | West et al. |
| 2005/0171527 A1 | 8/2005 | Bhola |
| 2006/0135961 A1 | 6/2006 | Rosenman et al. |
| 2007/0083194 A1 | 4/2007 | Kunis et al. |
| 2009/0125097 A1 | 5/2009 | Bruszewski et al. |
| 2011/0087211 A1 | 4/2011 | Kulesa |
| 2012/0123466 A1 | 5/2012 | Porter et al. |
| 2012/0130417 A1 | 5/2012 | Lepulu et al. |
| 2014/0277054 A1 | 9/2014 | Mcnamara et al. |
| 2015/0209526 A1 | 7/2015 | Matsubara et al. |
| 2016/0136398 A1* | 5/2016 | Heilman .......... A61M 25/0108 604/9 |
| 2016/0175041 A1 | 6/2016 | Govari et al. |
| 2018/0236211 A1 | 8/2018 | Henschel |
| 2019/0374254 A1 | 12/2019 | Arevalos et al. |
| 2020/0030588 A1 | 1/2020 | Heilman et al. |
| 2020/0038672 A1 | 2/2020 | Satake |
| 2020/0170662 A1 | 6/2020 | Vardi et al. |
| 2020/0238059 A1 | 7/2020 | Wang et al. |
| 2020/0261704 A1 | 8/2020 | Wang et al. |
| 2020/0289196 A1* | 9/2020 | Arevalos ........ A61B 17/320016 |
| 2020/0367924 A1 | 11/2020 | Lenker et al. |
| 2020/0376239 A1 | 12/2020 | Heilman |
| 2021/0038298 A1 | 2/2021 | Scott et al. |
| 2021/0045805 A1 | 2/2021 | Govari et al. |
| 2021/0085384 A1 | 3/2021 | Morey et al. |
| 2021/0196373 A1 | 7/2021 | He et al. |
| 2021/0228227 A1 | 7/2021 | Vardi et al. |
| 2021/0315629 A1 | 10/2021 | Yang et al. |
| 2021/0369321 A1 | 12/2021 | Yang et al. |
| 2021/0393324 A1 | 12/2021 | Moriyama et al. |
| 2022/0022954 A1 | 1/2022 | Shuros et al. |
| 2022/0110679 A1 | 4/2022 | Wang et al. |
| 2022/0249160 A1 | 8/2022 | Pate et al. |
| 2022/0257318 A1 | 8/2022 | Belalcazar |
| 2022/0265346 A1 | 8/2022 | Gupta et al. |
| 2022/0273279 A1* | 9/2022 | Valdez ............... A61M 27/002 |
| 2022/0330975 A1 | 10/2022 | Rafiee et al. |
| 2023/0000515 A1 | 1/2023 | Pollack |
| 2023/0041021 A1 | 2/2023 | Urbanski et al. |
| 2023/0078647 A1 | 3/2023 | Sharma et al. |
| 2023/0099410 A1 | 3/2023 | Primeaux |
| 2023/0210592 A1 | 7/2023 | Agnew et al. |
| 2023/0248425 A1 | 8/2023 | Iijima |
| 2023/0270491 A1 | 8/2023 | Mori et al. |
| 2023/0293877 A1 | 9/2023 | Hoem |
| 2024/0050717 A1 | 2/2024 | Rickerson et al. |

FOREIGN PATENT DOCUMENTS

| | | |
|---|---|---|
| CN | 115475001 A | 12/2022 |
| CN | 115590605 A | 1/2023 |
| EP | 1878453 B1 | 12/2014 |
| EP | 3238646 A2 | 11/2017 |
| EP | 3705154 A1 | 9/2020 |
| JP | 5237572 B2 | 7/2013 |
| WO | 2003/049643 A1 | 6/2003 |
| WO | 2018/229768 A2 | 12/2018 |
| WO | 2018/229768 A9 | 12/2018 |
| WO | 2020/024612 A1 | 2/2020 |
| WO | 2020/232384 A1 | 11/2020 |
| WO | 2020/242491 A1 | 12/2020 |
| WO | 2021/091566 A1 | 5/2021 |
| WO | 2021/190547 A1 | 9/2021 |
| WO | 2022/113054 A1 | 6/2022 |
| WO | 2022/135375 A1 | 6/2022 |
| WO | 2022/166973 A1 | 8/2022 |
| WO | 2022/246158 A1 | 11/2022 |
| WO | 2023/088572 A1 | 5/2023 |

OTHER PUBLICATIONS

Patent Cooperative Treaty, International Search Report, mailed Jul. 17, 2024, in PCT/US2024/022547.
Patent Cooperative Treaty, International Search Report, mailed Jul. 25, 2024, in PCT/US2024/023345.

(56) References Cited

OTHER PUBLICATIONS

Patent Cooperative Treaty, International Search Report, mailed Jun. 24, 2024, in PCT/US2024/018244.

Patent Cooperative Treaty, Written Opinion, mailed Jul. 17, 2024, in PCT/US2024/022547.

Patent Cooperative Treaty, Written Opinion, mailed Jul. 25, 2024, in PCT/US2024/023345.

Patent Cooperative Treaty, Written Opinion, mailed Jun. 24, 2024, in PCT/US2024/018244.

Tanaka et al., "Treatment of Hepatic Encephalopathy Due to Inferior Mesenteric Vein/Inferior Vena Cava and Gonadal Vein Shunt Using Dual Balloon-Occluded Retrograde Transvenous Obliteration," Cardiovasc Intervent Radiol, 2009, 32:390-393 (published online Oct. 7, 2008).

United States Patent and Trademark Office, Office Action mailed Jul. 12, 2024, for U.S. Appl. No. 18/593,832.

United States Patent and Trademark Office, Office Action mailed Jun. 20, 2024, for U.S. Appl. No. 18/623,954.

United States Patent and Trademark Office, Office Action mailed May 17, 2024, for U.S. Appl. No. 18/624,014.

Wilson et al., "Successful Tanscatheter Occlusion of an Anomalous Pulmonary Vein With Dual Drainage to the Left Atrium," Catheter Cardiovasc Interv, 2015, 85:1212-1216 (published online in Wiley Online Library, Apr. 7, 2015).

Patent Cooperative Treaty, International Search Report , mailed Feb. 6, 2025, in PCT/US2024/037165.

Patent Cooperative Treaty, Written Opinion, mailed Feb. 6, 2025, in PCT/US2024/037165.

* cited by examiner

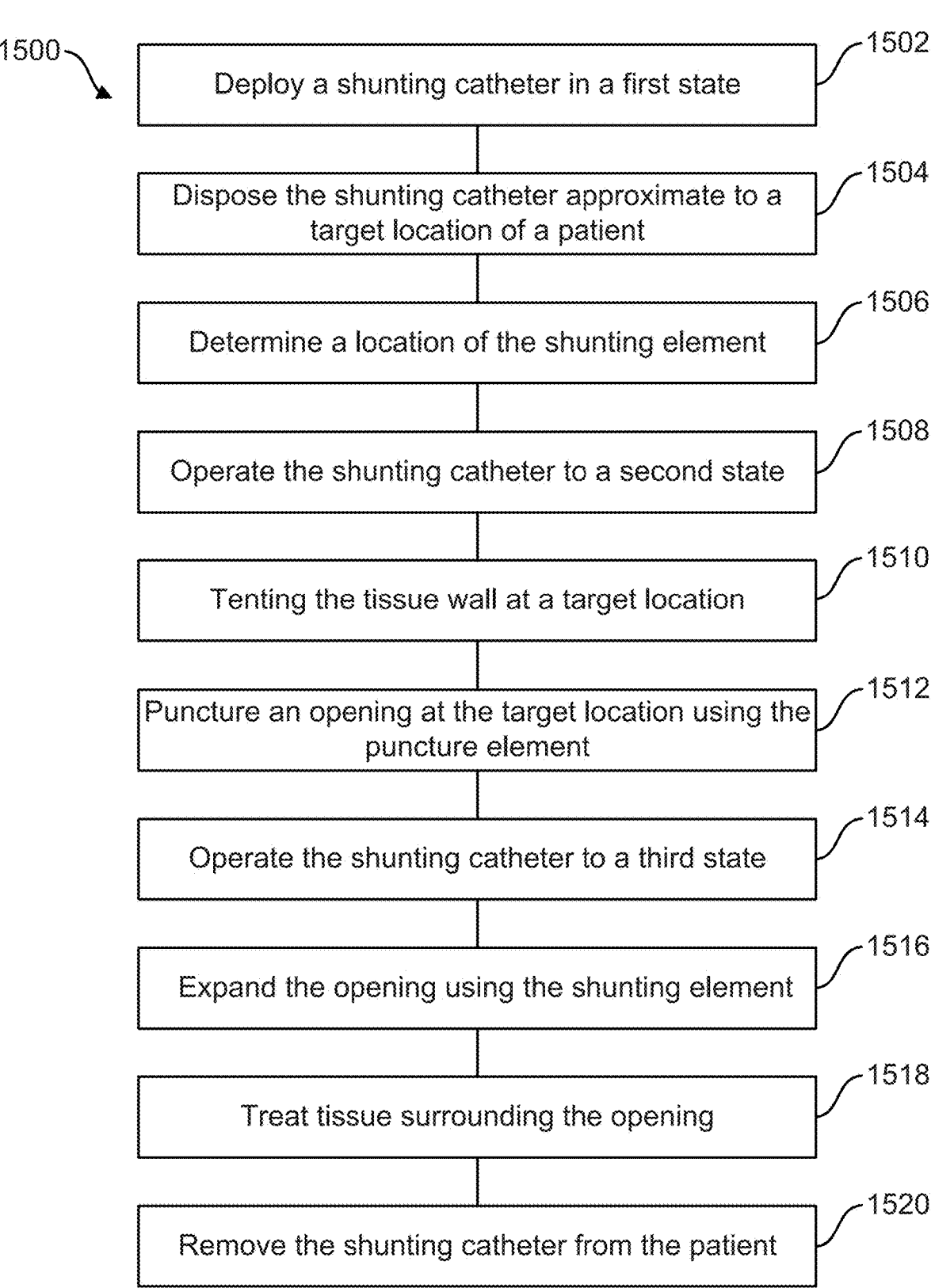

1500

1502 — Deploy a shunting catheter in a first state

1504 — Dispose the shunting catheter approximate to a target location of a patient 1506 — Determine a location of the shunting element 1508 — Operate the shunting catheter to a second state 1510 — Tenting the tissue wall at a target location 1512 — Puncture an opening at the target location using the puncture element 1514 — Operate the shunting catheter to a third state 1516 — Expand the opening using the shunting element 1518 — Treat tissue surrounding the opening 1520 — Remove the shunting catheter from the patient

FIG. 15

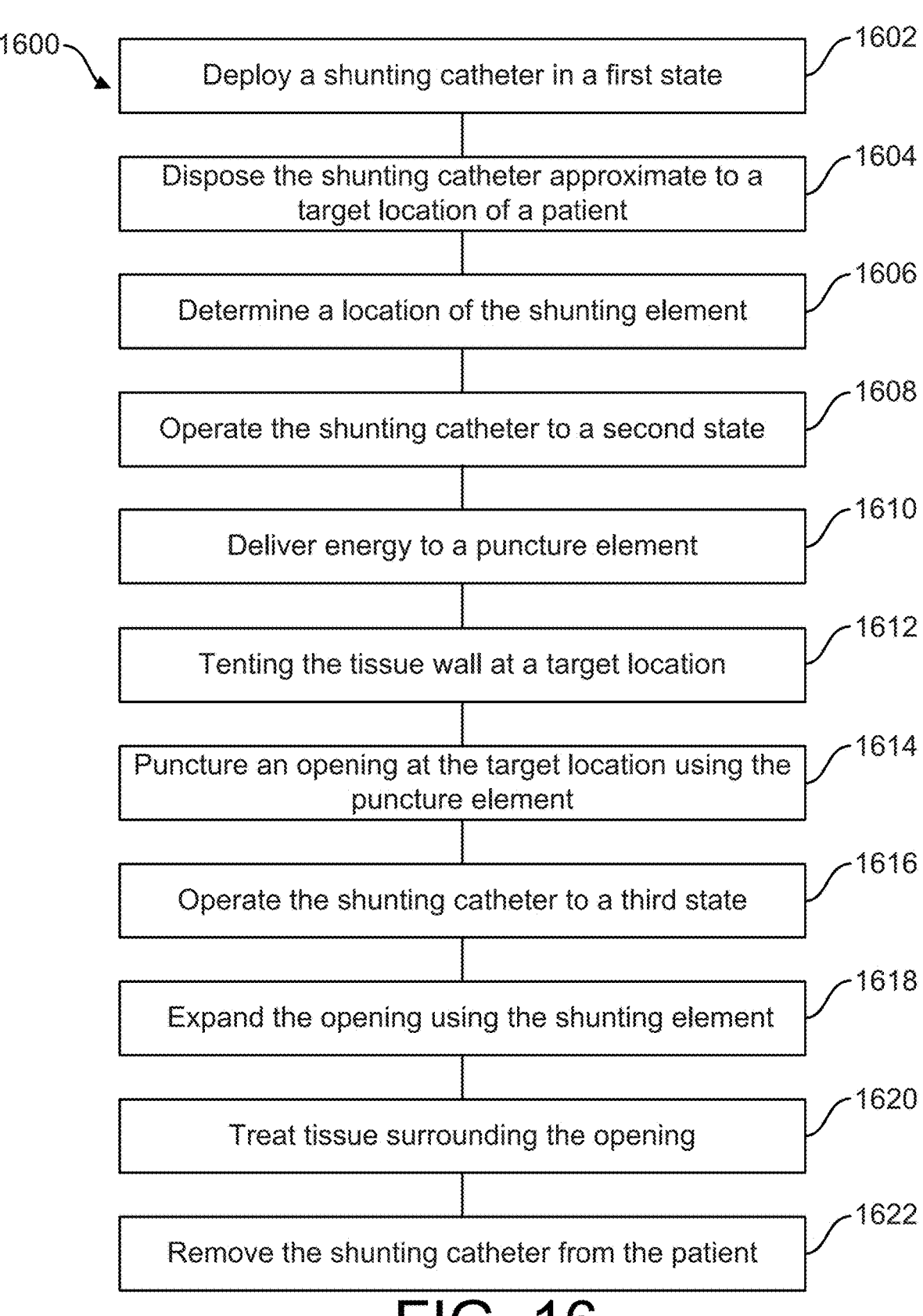

1600

1602 Deploy a shunting catheter in a first state

1604 Dispose the shunting catheter approximate to a target location of a patient 1606 Determine a location of the shunting element 1608 Operate the shunting catheter to a second state 1610 Deliver energy to a puncture element 1612 Tenting the tissue wall at a target location 1614 Puncture an opening at the target location using the puncture element 1616 Operate the shunting catheter to a third state 1618 Expand the opening using the shunting element 1620 Treat tissue surrounding the opening 1622 Remove the shunting catheter from the patient

FIG. 16

PUNCTURE ELEMENTS FOR SHUNTING CATHETERS

FIELD

Certain embodiments of the present disclosure relate to medical systems, apparatus, and methods for creating a shunt in a patient. More specifically, some embodiments of the present disclosure relate to medical systems, apparatus, and methods for creating a shunt on a cardiovascular system wall in a patient.

BACKGROUND

Heart failure is a serious condition that happens when heart cannot pump enough blood and oxygen to support other organs in your body. Heart failure is classified according to left ventricular (LV) function as "heart failure with reduced ejection fraction (EF)" (HFrEF; EF<40%), "mid-range EF" (HFmrEF; EF 40-49%), or "preserved EF" (HFpEF; EF≥50%). About half the patients with heart failure have HFpEF. HFpEF generally happens when LV and left atrial filling pressures increase significantly during exercise, with an associated increase in pulmonary pressures leading to pulmonary congestion. Structural interventions to lower elevated either left or right atrial filling pressures are gaining attention.

Studies in heart failure show that lowering left atrial pressure may reduce cardiovascular events while improving functional capacity. The creation of an interatrial shunt has emerged as a therapy to decompress the left atrium in patients with acute and chronic left HF. As such, attention has turned toward the development of interatrial shunt devices (IASDs) as a means of reducing the detrimental increase in left-sided filling pressures with exercise in an effort to improve symptomatology. The IASDs may be used to treat various kinds of heart failure and/or other diseases that may result in too high of a pressure in the right atrium of a patient.

SUMMARY

Current IASDs reside in the interatrial septum, with risk for right-to-left shunting and systemic embolization. Moreover, preservation of the interatrial septum is important with an increasing number of left-sided transseptal transcatheter interventions. Ways to improve IASDs for safer and better procedures are needed.

According to some embodiments, a shunting catheter includes a catheter shaft having a distal end and a proximal end, the catheter shaft including a shaft lumen; a shunting component including one or more electrodes; and a puncture assembly disposed in the shaft lumen at a first state and extended from the catheter shaft at a second state.

According to certain embodiments, a shunting catheter includes a catheter shaft having a distal end and a proximal end, the catheter shaft including a shaft lumen; and a puncture assembly disposed in the shaft lumen at a first state and extended from the catheter shaft at a second state. In some embodiments, the puncture assembly includes: a puncture element defining a longitudinal axis and including: a blade section including: a blade edge defining a first end, a second end, and a line following the blade edge, wherein the line and the longitudinal axis form an angle greater than zero degrees; and a tip defining a distal point of the puncture element, wherein the tip includes a first end of the blade edge.

According to some embodiments, a shunting catheter includes a catheter shaft having a distal end and a proximal end, the catheter shaft including a shaft lumen; a shunting component including one or more electrodes; and a puncture assembly disposed in the shaft lumen at a first state and extended from the catheter shaft at a second state; wherein the puncture element defines a conical shape, and wherein a distal tip of the puncture element is a tip of the conical shape.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 15 is a flow diagram illustrating a process of creating a shunt in a patient, in accordance with embodiments of the present disclosure.

FIG. 16 is a flow diagram illustrating a process of creating a shunt in a patient, in accordance with embodiments of the present disclosure.

Figure 1:
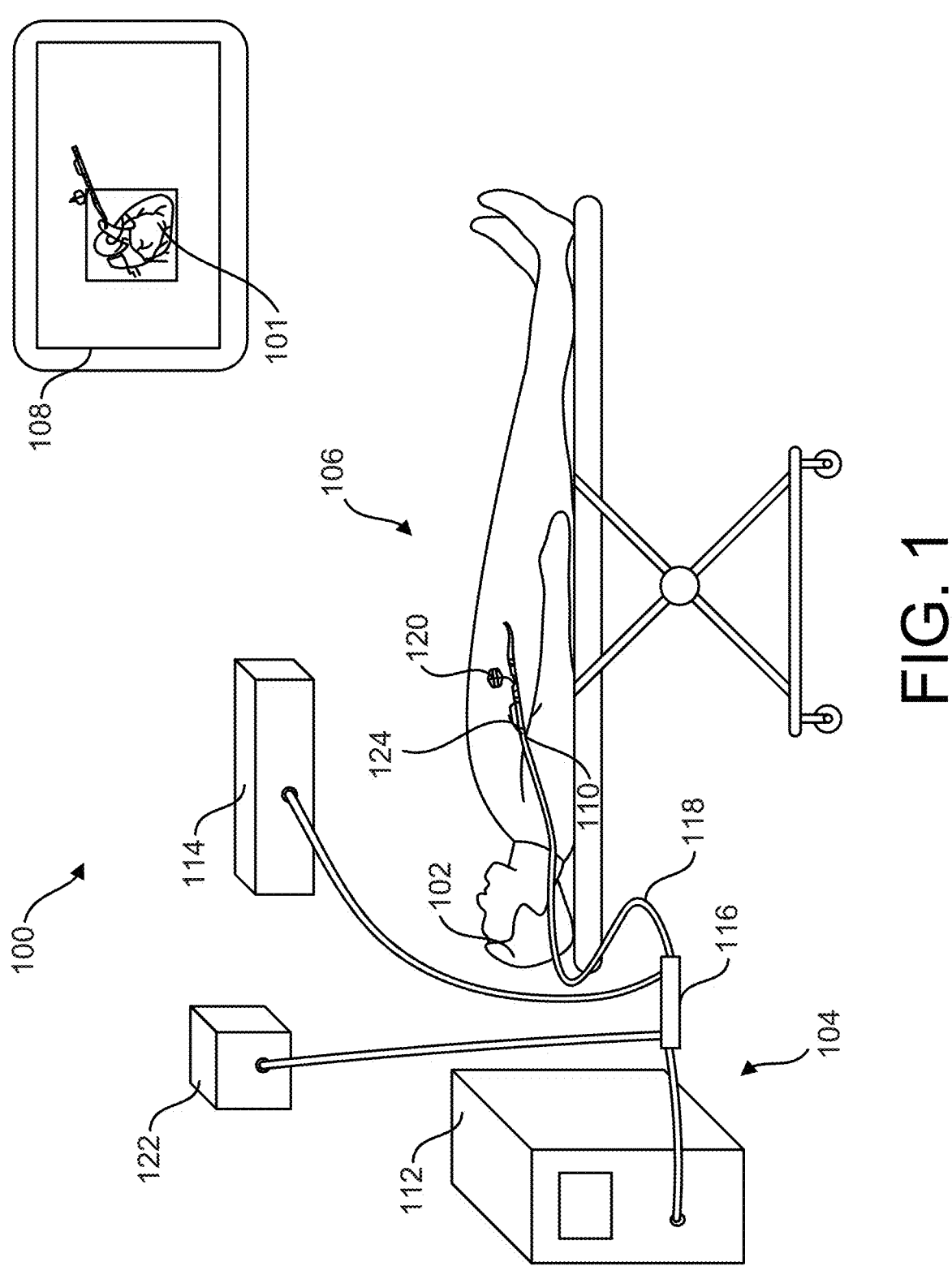
FIG. 1 is a diagram illustrating an exemplary clinical setting for treating a heart of the patient, using a shunting catheter system, in accordance with embodiments of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and/or dimensions are provided for selected elements. Those skilled in the art will recognize that many of the noted examples have a variety of suitable alternatives.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g., 1 to 5 includes 1, 1.5, 2, 2.75, 3, 3.80, 4, and 5) and any number within that range.

Although illustrative methods may be represented by one or more drawings (e.g., flow diagrams, communication flows, etc.), the drawings should not be interpreted as implying any requirement of, or particular order among or between, various steps disclosed herein. However, some embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information. In some embodiments, the term "receive" or "receiving" means obtaining from a data repository (e.g., database), from another system or service, from another software, or from another software component in a same software. In certain embodiments, the term "access" or "accessing" means retrieving data or information, and/or generating data or information.

There are various approaches for creating an interatrial shunt, which is a connection or gateway between the left and right atria of a patient's heart for blood to flow through. In some embodiments, examples of interatrial shunt devices (IASDs) include implants or shunting catheters. For example, devices reside in the interatrial septum, with risk for right-to-left shunting and systemic embolization. In some examples, preservation of the interatrial septum is important with an increasing number of left-sided transseptal transcatheter interventions. Ways to improve IASDs for safer and better procedures are needed. At least some embodiments of the present disclosure are directed to a shunting catheter for deployment through a patient's coronary sinus (CS) for creating a shunt between the CS and the patient's left atrium (LA). At least some embodiments of the present disclosure are directed to a shunting catheter for deployment through a patient's atrial septum (AS) for atrial septal shunting.

A patient's CS ostium may have a diameter of from about 10 mm to about 20 mm. As the CS is a relatively small vessel, at least some embodiments of the present disclosure are directed to features of a shunting catheter that helps angle a puncture element towards a patient's vessels during deployment. In some embodiments, the shunting catheter includes a catheter shaft, a shunting element, and a puncture assembly disposed in the shaft at a first state and extended from the catheter shaft at a second state and/or third state. In some embodiments, the catheter shaft is made of flexible materials that bend according to the anatomy of the CS to conform to the shape of the patient's CS. In yet some embodiments, the catheter shaft includes a stabilizing element such as distal tip that has a curve (e.g., a pre-existing curve) conforming to the shape of a patient's CS to help stabilize the catheter and minimize potential damage to a patient's tissue wall (e.g., the vessel wall of a patient's CS).

In some embodiments, an apposition element is protruded from the catheter shaft during deployment to help stabilize the catheter at a desired location for creating the shunt. In certain embodiments, the shunting element further includes an expandable element (e.g., a balloon, a basket) and a tube (e.g., a hypotube) to support the expandable element. The tube may have a plurality of cuts along the tube to help facilitate bending of the tube. In some embodiments, a shunt is formed in a patient's CS vessel by creating an opening between the patient's CS and LA. In certain embodiments, the shunting catheter is inserted through the patient's superior vena cava (SVC) via a transjugular approach. In certain embodiments, the shunting catheter is inserted through the patient's inferior vena cava (IVC) via a transfemoral approach.

FIG. 1 is a diagram illustrating an exemplary clinical setting 100 for treating a heart 101 of the patient 102, using a shunting catheter system 104, in accordance with embodiments of the present disclosure. The shunting catheter system 104 includes a shunting device 106. As will be appreciated by the skilled artisan, the clinical setting 100 may have other components and arrangements of components that are not shown in FIG. 1. In some embodiments, the shunting catheter system 104 includes or is coupled to an imaging system (e.g., an X-ray system) which may include one or more visualization elements and a display 108. In some embodiments, one or more visualization elements may be disposed on the shunting device 106. In certain embodiments, the imaging system can help guide a physician's operation of the shunting catheter 110 during procedure.

The shunting device 106 includes a shunting catheter 110, a controller 112, and an energy source 114 (e.g., a generator). The controller 112 is configured to control functional aspects of the shunting device 106. In some embodiments, the controller 112 is configured to control the energy source 114 to deliver energy to the shunting catheter 110. The controller 112 may be connected to the one or more visualization elements to facilitate positioning of the shunting catheter 110 in a patient's heart during procedure. In some embodiments, the energy source 114 is connected to the controller 112. In yet some embodiments, the energy source 114 may be incorporated into the controller 112.

As will be appreciated by the skilled artisan, the depiction of the shunting catheter system 104 shown in FIG. 1 is intended to provide a general overview of the various components of the shunting catheter system 104 and is not in any way intended to imply that the disclosure is limited to any set of components or arrangement of the components. For example, the skilled artisan will readily recognize that additional hardware components, e.g., breakout boxes, workstations, and the like, can and likely will be included in the shunting catheter system 104.

According to some embodiments, the shunting device 106 includes a handle 116, a catheter shaft 118, a puncture element (e.g., a puncture needle) configured to puncture through a tissue wall, and a shunting element 120 configured to provide shunting at a target location. In certain embodiments, the puncture element may be curved. In some instances, the puncture element may be curved or angled to bias a distal tip of the puncture element towards a tissue wall of the patient 102 when in use. In certain embodiments, the shunting element 120 is inflatable and connected to an inflation source 122. In some instances, the shunting element 120 includes an expandable element (e.g., a balloon, a basket). In certain embodiments, the shunting element 120 is connected to the energy source 114 to provide shunting. For example, the shunting element 120 includes electrodes to receive electrical power from the energy source 114 to deliver ablation energy to the target location (e.g., a target tissue) at a cardiovascular system (e.g., a circulatory system) wall. In certain embodiments, the handle 116 is configured to be operated by a user to position the puncture element and the shunting element 120 at the desired anatomical location. The catheter shaft 118 generally defines a longitudinal axis of the shunting catheter 110. In some embodiments, the shunting element 120 may be connected to a shunting element shaft positioned within the catheter shaft 118 at a first state (e.g., before a deployment and/or during a deployment to position the shunting element 120). In certain embodiments, the shunting element shaft has a pre-determined curve. In some examples, the shunting element shaft has a pre-determined curve for the shunting element to deploy. In certain embodiments, the shunting element shaft is extended from the catheter shaft 118 at a second state (e.g., a puncture state to puncture through a tissue wall of a patient) and/or a third state (e.g., a shunting state to use the shunting element).

According to certain embodiments, during deployment, the shunting device 106 including the catheter shaft 118 enters through a patient's CS ostium located in the patient's right atrium. The shunting device 106 may then be oriented through one or more mechanisms in the patient's CS, as will be discussed in more details below. In some embodiments, in order to conform to the shape of the patient's CS, the catheter shaft 118 is made of flexible materials that may bend according to the anatomy of the CS.

In certain embodiments, the shunting catheter 110 includes an apposition element 124 disposed proximate to the shunting element 120. In some embodiments, the apposition element is disposed within a shaft (e.g., an outer shaft) at the first state. In some embodiments, the apposition element 124 is protruded from the catheter shaft 118 at the first state, the second state, and/or the third state. In certain embodiments, the apposition element 124 can appose to a cardiovascular system wall (e.g., the front wall or back wall of the CS, a left atrium wall, a right atrium wall, etc.) at the second state and/or third state, for example, to help position and/or stabilize the shunting element 120. In certain embodiments, the apposition element 124 includes a braid structure. In some embodiment, the apposition element 124 may include a nitinol braid that can be held within the catheter shaft 118. In some embodiments, the shunting catheter 110 does not include an apposition element.

According to some embodiments, various components (e.g., the controller 112) of the shunting catheter system 104 may be implemented on one or more computing devices. A computing device may include any type of computing device suitable for implementing embodiments of the disclosure. Examples of computing devices include specialized computing devices or general-purpose computing devices such as workstations, servers, laptops, portable devices, desktop, tablet computers, hand-held devices, general-purpose graphics processing units (GPGPUs), and the like, all of which are contemplated within the scope of FIG. 1 with reference to various components of the shunting catheter system 104.

In some embodiments, a computing device (e.g., the controller 112) includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in some embodiments, the computing device may include a number of processors, a number of memory components, a number of I/O ports, a number of I/O components, and/or a number of power supplies. Additionally, any number of these components, or combinations thereof, may be distributed and/or duplicated across a number of computing devices. In some embodiments, various components or parts of components (e.g., controller 112, shunting catheter 110, etc.) can be integrated into a physical device.

In some embodiments, the shunting catheter system 104 includes one or more memories (not illustrated). The one or more memories includes computer-readable media in the form of volatile and/or nonvolatile memory, transitory and/or non-transitory storage media and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In some embodiments, the one or more memories store computer-executable instructions for causing a processor (e.g., the controller 112) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Program components may be programmed using any number of different programming environments, including various languages, development kits, frameworks, and/or the like. Some or all of the functionality contemplated herein may also, or alternatively, be implemented in hardware and/or firmware.

In some embodiments, the memory may include a data repository which may be implemented using any one of the configurations described below. A data repository may include random access memories, flat files, XML files, and/or one or more database management systems (DBMS) executing on one or more database servers or a data center. A database management system may be a relational (RDBMS), hierarchical (HDBMS), multidimensional (MDBMS), object oriented (ODBMS or OODBMS) or object relational (ORDBMS) database management system, and the like. The data repository may be, for example, a single relational database. In some cases, the data repository may include a plurality of databases that can exchange and aggregate data by a data integration process or software application. In an exemplary embodiment, at least part of the data repository may be hosted in a cloud data center. In some cases, a data repository may be hosted on a single computer, a server, a storage device, a cloud server, or the like. In some other cases, a data repository may be hosted on a series of networked computers, servers, or devices. In some cases, a data repository may be hosted on tiers of data storage devices including local, regional, and central.

Various components of the shunting catheter system 104 can communicate via or be coupled to via a communication interface, for example, a wired or wireless interface. The communication interface includes, but is not limited to, any wired or wireless short-range and long-range communication interfaces. The wired interface can use cables, umbilicals, and the like. The short-range communication interfaces may be, for example, local area network (LAN), interfaces conforming to known communications standards, such as Bluetooth™ standard, IEEE 802 standards (e.g., IEEE 802.11), a ZigBee™ or similar specification, such as those based on the IEEE 802.15.4 standard, or other public or proprietary wireless protocol. The long-range communication interfaces may be, for example, wide area network (WAN), cellular network interfaces, satellite communication interfaces, etc. The communication interface may be either within a private computer network, such as intranet, or on a public computer network, such as the internet. Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

Figure 2:
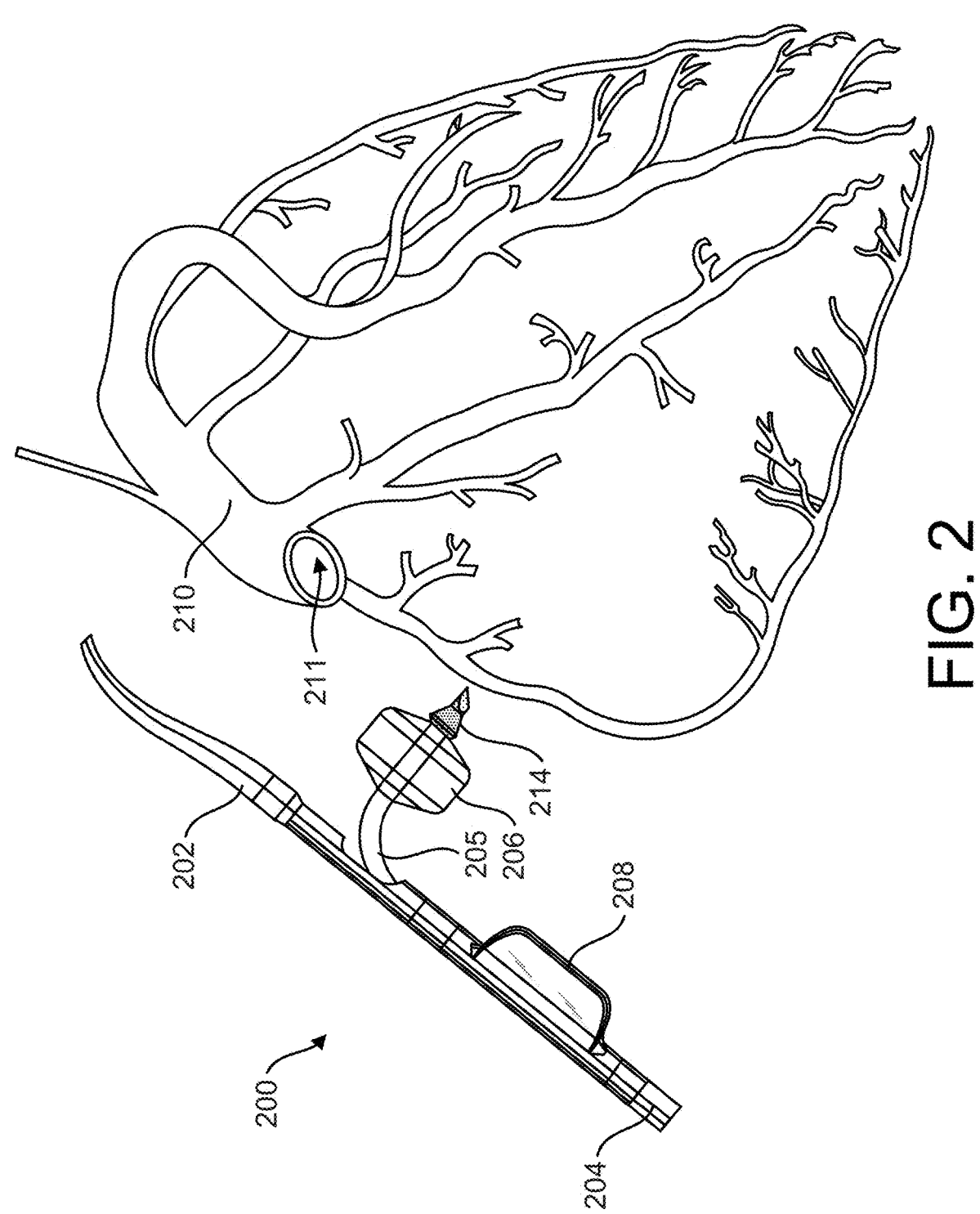
FIG. 2 is a schematic diagram illustrating an example of a shunting device to be deployed in a heart of a patient, in accordance with embodiments of the present disclosure.

FIG. 2 is a schematic diagram illustrating an example of a shunting device 200 to be deployed in a heart of a patient, in accordance with embodiments of the present disclosure. FIG. 2 is merely an example. One of the ordinary skilled in the art would recognize many variations, alternatives, and modifications. As shown, the shunting device 200 includes a shunting catheter 202 to be delivered through a patient's coronary sinus (CS) 210 via the CS ostium 211. In some embodiments, the shunting catheter 202 includes a catheter shaft 204, a shunting element 206, and a puncture assembly 214. In some embodiments, the shunting catheter 202 may further include an apposition element 208. In certain embodiments, the catheter shaft 204 has a curve at its distal end 205. In some embodiments, as illustrated, the shunting element 206 is extended from the catheter shaft 204 at a second state (e.g., a puncturing state) and/or a third state (e.g., a state to provide shunting). In certain embodiments, the shunting element 206 may include an expandable element (e.g., a balloon, a basket) connected to a shunting element shaft positioned within an expandable element sheath (not shown), and collectively within the catheter shaft 204, at a first state (e.g., before a deployment and/or during a deployment to position the shunting element 206). In certain examples, the shunting element 206 forms an angle greater than 30 degrees from the distal end 205 of the catheter shaft 204. In some embodiments, the shunting element 206 forms an angle proximate to 90 degrees from the catheter shaft 204. In some embodiments, the shunting element 206 forms an angle in the range of 30 degrees to 120 degrees from the catheter shaft 204.

In some embodiments, the puncture assembly 214 (e.g., along with the shunting element 206) is extended from the catheter shaft 204 at a second state (e.g., a state to puncture a tissue wall). According to some embodiments, the puncture assembly 214 includes a puncture element having a tip defining a distal point of the puncture element and a blade section. In some embodiments, the blade section of the puncture element has a tapered shape and includes a blade edge. For example, the blade section has a distal end at the blade edge and a proximal end close to the shunting element 206, with the blade section at the proximal end having a first thickness and the blade section at the distal end having a second thickness, where the second thickness is smaller than the first thickness. In some embodiments, a distal end of the blade edge is the tip of the puncture element. In certain embodiments, the blade section includes two flat surfaces, where the intersection of the two flat surfaces defines the blade edge, and a curved surface surrounding the two flat surfaces (see e.g., FIG. 9B).

In some embodiments, the puncture element of the puncture assembly 214 may be configured to deliver energy, or include one or more electrodes configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall of a patient).

In some embodiments, the catheter shaft 204 is made of flexible material that may curve with the anatomy of the patient's CS 210. In certain embodiments, for example, the catheter shaft 204 may include polyether block amide, nylon, silicone, or a combination thereof. In some instances, the catheter shaft 204 may be a multi-layered and multi-material component. In some examples, the catheter shaft 204 is reinforced with a braid and can have an etched or casted liner. In certain examples, the catheter shaft 204 is reinforced with a laser cut hypotube. The braid and/or hypotube used for reinforcing the catheter shaft 204 may be made of nitinol, stainless steel, or other metals, as well as rigid plastics (e.g., polyetheretherketone (PEEK)). The liner may be made from polyetheretherketone (PEEK), polytetrafluoroethylene (PTFE), copolymers of polyamide and polyether, or a combination thereof. In some embodiments, the catheter shaft 204 is coated for lubricity with a hydrophilic coating, or other types of coating suitable for coating a catheter shaft as known by a skilled person in the art.

In some embodiments, the shunting catheter 202 has a diameter of from about 2 mm to about 10 mm. In certain embodiments, the shunting catheter 202 has a diameter of from about 3.5 mm to about 8.5 mm. In some embodiments, the shunting catheter has a diameter of from about 5 mm to about 7 mm. In certain embodiments, the shunting catheter 202 may have a diameter allowing it to pass through vessels and parts of the cardiovascular system to reach a target location.

Figure 3:
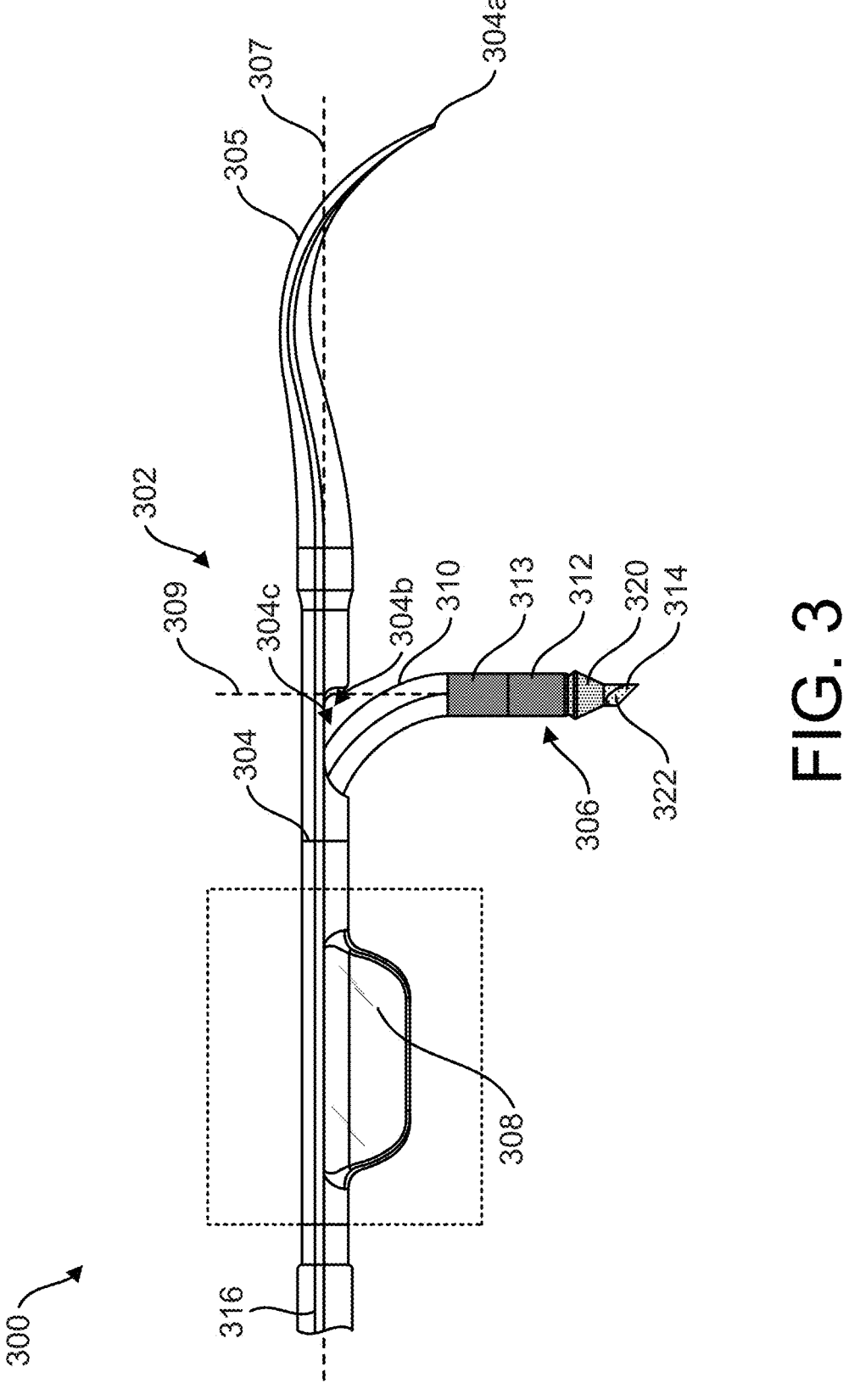
FIG. 3 is a schematic diagram of a side view of an example of a shunting device, in accordance with embodiments of the present disclosure.

FIG. 3 is a schematic diagram of a side view of an example of a shunting device 300, in accordance with embodiments of the present disclosure. FIG. 3 is merely an example. One of the ordinary skilled in the art would recognize many variations, alternatives, and modifications. As shown, in some embodiments, the shunting device 300 includes a shunting catheter 302 to be delivered through a patient's coronary sinus (CS). In certain embodiments, the shunting catheter 302 includes a catheter shaft 304, a shunting element 306, also referred to as a shunting component, and a puncture assembly 314. In some embodiments, the shunting catheter 302 may further include an apposition element 308.

According to certain embodiments, the catheter shaft 304 has a distal end 304*a*, a proximal end (not shown), and a shaft lumen 304*b*. In some embodiments, the catheter shaft 304 is made of flexible material that may curve with the anatomy of the patient's CS. In certain embodiments, catheter shaft 304 may include polyether block amide, nylon, silicone, and/or a combination thereof. In some instances, the catheter shaft 304 may be a multi-layered and multi-material component. In some examples, the catheter shaft 304 is reinforced with a braid and can have an etched or casted liner. In certain examples, the catheter shaft 204 is reinforced with a laser cut hypotube. The braid and/or hypotube used for reinforcing the catheter shaft 204 may be made of nitinol, stainless steel, or other metals, as well as rigid plastics (e.g., polyetheretherketone (PEEK)). The liner may be made from polyetheretherketone (PEEK), polytetrafluoroethylene (PTFE), copolymers of polyamide and polyether, or a combination thereof. In certain embodiments, the catheter shaft 304 may be injection molded or extruded. In some embodiments, the catheter shaft 304 is coated for lubricity with a hydrophilic coating, or other types of coating suitable for coating a catheter shaft as known by a skilled person in the art. In some instances, the catheter shaft 304 may have multiple lumens.

According to some embodiments, the catheter shaft 304 may include a stabilizing element such as distal tip 305 at the distal end 304*a*. In some embodiments, the distal tip 305 has a curve (e.g., a pre-existing curve), for example, a curve conforming to the anatomy of a patient's CS. In certain embodiments, the distal tip 305 is straight. In some instances, the distal tip 305 may be made of a different material than other parts of the catheter shaft 304. In some instances, for example, the distal tip 305 may be made of a material more flexible than the material of other parts of the catheter shaft 304. The distal tip 305 may be injection molded or machined to have a unique geometry (e.g., a curve) for better stabilizing the catheter shaft 304 during deployment.

According to some embodiments, the distal tip 305 may have a length of from about 5 mm to about 85 mm. In certain embodiments, the catheter shaft 304 includes a shaft opening 304*c*. In some embodiments, a portion of the catheter shaft from the shaft opening 304*c* and the distal end 304*a* has a curve. In some embodiments, the catheter shaft 304 defines a first axis 307, and the shunting element 306 defines a second axis 309 at the second state after deployment. In certain embodiments, the second axis 309 and the first axis 307 form an angle greater than zero degree.

According to certain embodiments, the shunting element 306 is disposed in the shaft lumen 304*b* at a first state (e.g., before a deployment and/or during a deployment to position the shunting element 306). In some embodiments, the shunting element 306 includes an expandable element 312 (e.g., a balloon, a basket) disposed within a shunting element shaft 310. In certain embodiments, the expandable element 312 may be positioned within an expandable element sheath 313, and collectively within the catheter shaft 304, at a first state. In some embodiments, the expandable element 312 is crimped when positioned within the expandable element sheath 313 at a first state. In certain embodiments, the expandable element 312 is an elongated element. The shunting element 306 may be connected to the shunting element shaft 310 positioned within the shaft lumen 304*b* of the catheter shaft 304 at a first state. In certain embodiments, the shunting element shaft 310 has a pre-determined curve. In some examples, the shunting element shaft 310 has a pre-determined curve for the shunting element 306 to deploy. In certain embodiments, the shunting element shaft is extended from the shaft lumen 304*b* of the catheter shaft 304 at a second state (e.g., a puncturing state to puncture through a tissue wall of a patient) and/or a third state (e.g., a shunting state to use the shunting element). In some examples, the expandable element 312 may be a balloon or a basket configured to deliver ablative energy, and is expanded when the shunting element 306 is at a third state. In some embodiments, the shunting element 306 does not include an expandable element 312, and instead include one or more electrodes configured to deliver ablative energy to a patient's tissue, where the one or more electrodes are placed directly on the shunting element shaft 310.

According to certain embodiments, the width of the expandable element 312 (w) after expansion, for example in a third state as shown in FIG. 2, can range from about 3 mm to about 15 mm. In some embodiments, the width of the expandable element 312 (w) can range from about 3.5 mm to about 12 mm. In certain embodiments, the width of the expandable element 312 (w) can range from about 4 mm to about 10 mm. In some embodiments, the width of the expandable element 312 (w) can range from about 4.5 mm to about 8 mm.

According to certain embodiments, the puncture assembly 314 is disposed in the shaft lumen 304*b* at a first state. The puncture assembly 314 may be connected to the shunting element 306 positioned within the shaft lumen 304*b* of the catheter shaft 304 at a first state (e.g., before a deployment and/or during a deployment to position the shunting element 306).

In some embodiments, the puncture assembly 314 (e.g., along with the shunting element 306) is extended from the catheter shaft 304 at a second state (e.g., a puncturing state to puncture through a tissue wall). According to some embodiments, the puncture assembly 314 includes a puncture element 322 having a tip defining a distal point of the puncture element and a blade section. In some embodiments, the blade section of the puncture element has a tapered shape and includes a blade edge. For example, the blade section has a distal end at the blade edge and a proximal end close to the expandable element 312, with the blade section at the proximal end having a first thickness and the blade section at the distal end having a second thickness, where the second thickness is smaller than the first thickness. In some embodiments, a distal end of the blade edge is the tip of the puncture element. In certain embodiments, the blade section includes two flat surfaces, where the intersection of the two flat surfaces defines the blade edge, and a curved surface surrounding the two flat surfaces (see e.g., FIG. 9B).

In some embodiments, the puncture element of the puncture assembly 314 may be configured to deliver energy, or include one or more electrodes configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall of a patient).

In certain embodiments, puncture assembly 314 further includes a puncture element 322. In some instances, the puncture element 322 may include a curve at a distal portion (e.g., the puncture element 322 of the puncture assembly 314 may be angled or curved. See e.g., FIGS. 8-13). In some embodiments, the puncture assembly 314 may include a dilator 320.

In certain embodiments, the puncture assembly 314 has a pre-determined curve. In some embodiments, the puncture assembly 314 may form an angle proximate to 90 degrees from the catheter shaft 304. In some embodiments, the puncture assembly 314 may form an angle in the range of 30 degrees to 120 degrees from the catheter shaft 304. In certain embodiments, the puncture assembly 314 is extended from the shaft lumen 304b of the catheter shaft 304 at a second state (e.g., a puncturing state to use the puncture element on a distal end of the puncture assembly 314). In some examples, the puncture assembly 314 may include one or more electrodes configured to deliver ablative energy when the puncture assembly 314 is at a second state. In certain examples, the puncture assembly 314 may include a puncture element made of conductive material and configured to deliver ablative energy when the puncture assembly 314 is at a second state.

According to some embodiments, the shunting catheter 302 further includes an outer shaft 316 disposed outside of at least a part of the catheter shaft 304 during deployment. In some embodiments, the outer shaft 316 is made of flexible material that may curve with the anatomy of the patient's CS. In certain embodiments, for example, the outer shaft 316 may include polyether block amide, nylon, silicone, or a combination thereof. In some instances, the outer shaft 316 may be a multi-layered and multi-material component. In some examples, the outer shaft 316 is reinforced with a braid and/or can have an etched or casted liner. In certain examples, the catheter shaft 204 is reinforced with a laser cut hypotube. The braid and/or hypotube used for reinforcing the catheter shaft 204 may be made of nitinol, stainless steel, or other metals, as well as rigid plastics (e.g., polyetheretherketone (PEEK)). The liner may be made from polyetheretherketone (PEEK), polytetrafluoroethylene (PTFE), copolymers of polyamide and polyether, or a combination thereof. In certain embodiments, the outer shaft 316 may be injection molded or extruded. In some embodiments, the catheter shaft 304 is coated for lubricity with a hydrophilic coating, or other types of coating suitable for coating a catheter shaft as known by a skilled person in the art.

According to certain embodiments, the shunting device 300 does not include an apposition element. In some embodiments, the shunting device 300 includes an apposition element 308 disposed within the outer shaft 316 at a first state (e.g., during deployment). In some embodiments, the apposition element 308 protrudes from the catheter shaft 304 during deployment. The apposition element 308 is flexible and compressed to fit within the outer shaft 316, and configured to decompress and protrude from the catheter shaft 304 during deployment. In some embodiments, the apposition element 308 is disposed proximate to the shunting element 306 and/or the one or more shaft openings 304c. In some instances, the apposition element 308 is a braided structure including one or more nickel titanium wires. In yet some instances, the apposition element 308 is made of a flexible material having a portion protruding from the catheter shaft 304. In some examples, the flexible material may be a foam. In some instances, the flexible material may be a balloon filled with a contrast solution that shows up under fluoroscopy. In yet some instances, the flexible material may be a polymer with a radiopaque marker added for visualization. The radiopaque marker may include tantalum, gold, or any radiopaque marker known by a skilled person in the art.

In certain embodiments, the apposition element 308 is configured to appose a patient's tissue wall (e.g., the vessel wall of a patient's CS or LA) such that the shunting catheter 302 is stabilized in one position once deployed. According to some embodiments, the apposition element 308 has several benefits, one of which is the stabilization of catheter 302 after deployment. Any movement or lack thereof of the apposition element 308 provides an estimated distance of how far the catheter 302 is away from a tissue wall (e.g., the vessel wall of patient's CS). In some instances, the apposition element 308 may include a braided element (not shown), even when the apposition element 308 is apposing a tissue wall (e.g., the vessel wall of a patient's CS), the openings between the braids still allow blood flow through the apposition element 308, thus reducing the risk of thrombus formation caused by any occlusion in the vessel.

Figure 4:
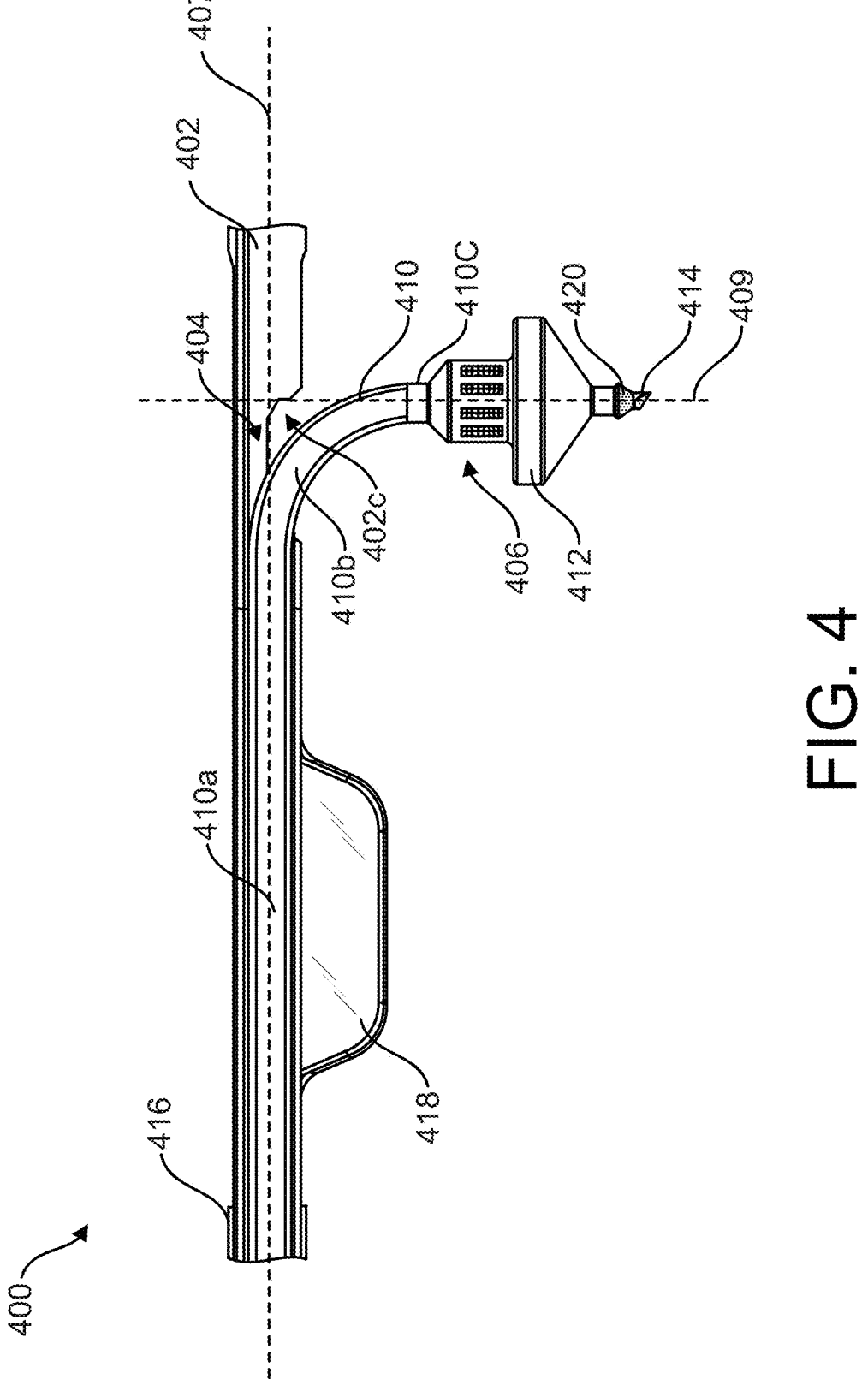
FIG. 4 is a schematic diagram of a cross-sectional view of an example of a shunting catheter, in accordance with embodiments of the present disclosure.

FIG. 4 is a schematic diagram of a cross-sectional view of an example of a shunting catheter 400, in accordance with embodiments of the present disclosure. As shown, the shunting catheter 400 includes a catheter shaft 402 having a shaft lumen 404, and a shunting element 406 and puncture assembly 414 disposed within the shaft lumen 404 at a first state (e.g., during deployment). In some embodiments, the puncture assembly 414 may include a dilator 420.

In some embodiments, the shunting element 406 is extended from the catheter shaft 402 at a second state and/or third state. The shunting element 406 may include an expandable element 412 (e.g., a balloon, a basket) disposed within a shunting element shaft 410. In certain embodiments, the expandable element 412 may include an anchor component configured to facilitate the placement of the expandable element 412 within a patient (e.g., at a target location of a vessel). In some examples, the expandable element 412 may be a balloon or a basket configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue.

In some embodiments, the shunting element 406 is positioned within the catheter shaft 402 at a first state (e.g., before a deployment and/or during a deployment to position the shunting element 406). In certain embodiments, the shunting element shaft 410 has a pre-determined curve. In some examples, the shunting element shaft 410 has a pre-determined curve for the shunting element 406 to deploy. In certain embodiments, the shunting element shaft 410 is extended from the catheter shaft 402 at a third state (e.g., a shunting state, a shunting state to use a shunting element). In certain embodiments, the puncture assembly 414 has a predetermined curve. In certain embodiments, the puncture assembly 414 is extended from the catheter shaft 402 at a second state (e.g., a puncturing state to use the puncture element).

In some embodiments, the puncture assembly 414 (e.g., along with the shunting element 406) is extended from the shaft lumen 404 at a second state (e.g., a puncturing state to puncture a tissue wall). According to some embodiments, the puncture assembly 414 includes a puncture element having a tip defining a distal point of the puncture element and a blade section. In some embodiments, the blade section of the puncture element has a tapered shape and includes a blade edge. For example, the blade section has a distal end at the blade edge and a proximal end close to the expandable element 412, with the blade section at the proximal end having a first thickness and the blade section at the distal end having a second thickness, where the second thickness is smaller than the first thickness. In some embodiments, a distal end of the blade edge is the tip of the puncture element. In certain embodiments, the blade section includes two flat surfaces, where the intersection of the two flat surfaces defines the blade edge, and a curved surface surrounding the two flat surfaces (see e.g., FIG. 9B).

In some embodiments, the puncture element of the puncture assembly 414 is configured to deliver energy, or includes one or more electrodes configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall of a patient), for example, to create an opening.

According to some embodiments, the catheter shaft 402 includes a shaft opening 402c. In some embodiments, the catheter shaft 402 defines a first axis 407, and the shunting element 406 defines a second axis 409. In certain embodiments, the second axis 409 and the first axis 407 form an angle greater than zero degree. In certain examples, the second axis 409 and the first axis 407 forms an angle greater than 30 degrees. In some embodiments, the second axis 409 and the first axis 407 form an angle proximate to 90 degrees. In some embodiments, the second axis 409 and the first axis 407 form an angle in the range of 30 degrees to 120 degrees. In some instances, the catheter shaft 402 includes a pre-curve formed from a semi-rigid or rigid material. The semi-rigid or rigid material may include nitinol or stainless steel (SS) with a curve built in before deployment. In some instances, the puncture assembly 414 includes a pre-curve formed from a semi-rigid or rigid material. The semi-rigid or rigid material of the puncture assembly 414 may include nitinol or SS with a curve built in before deployment.

In some embodiments, the shunting element shaft 410 includes a curved portion 410b that forms an arc connecting a first straight portion of shunting element shaft 410a disposed inside the shaft lumen 404 and a second straight portion 410c of the shunting element shaft 410 extended outward from the shaft lumen 404. In some embodiments, for example as shown, the curved portion 410b of the shunting element shaft 410 is adjacent the shaft opening 402c. In certain embodiments, the expandable element 412 is located at the second straight portion 410c and outside of the curved portion 410b of the shunting element shaft 410.

According to certain embodiments, the shunting catheter 400 may further include an outer shaft 416 disposed outside of the catheter shaft 402 and enclosing the catheter shaft 402 and the shunting element 406 in a compressed state before deployment. In some embodiments, the shunting catheter 400 may further include an apposition element 418 disposed within the outer shaft 416 in a compressed state before deployment. The outer shaft 416 may have a diameter of from about 12 to about 22 french, or from about 14 to about 20 french, or from about 16 to about 18 french, or may have a diameter encompassed within these ranges. In some embodiments, for example during deployment, the outer shaft 416 is pulled back to deploy and/or position the catheter shaft 402 including the shunting element 406 and/or the apposition element 418. In some embodiments, a diameter of the puncture assembly 414 may be approximately the same as a diameter of the shunting element 406 at a deployment state. In some examples, the largest diameter of the puncture assembly 414 may be approximately the same as the largest diameter of the shunting element 406 when the shunting element 406 is in a compressed state for deployment of catheter 400.

In certain embodiments, the shunting catheter 400 includes multiple compartments (e.g., lumens) for various elements to provide more targeted control during deployment. For example, the shunting catheter 400 may include an additional lumen in between the catheter shaft 402 and the shunting element shaft 410 for more precise control during deployment of the shunting element 406. Similarly, for example, the shunting catheter 400 may include an additional lumen in between outer shaft 416 and the catheter shaft 402 for more precise control during deployment of the apposition element 418. In some embodiments, the shunting catheter 400 may include lumens for containing functional components such as a guidewire or pull wire assembly, as will be discussed further below. In yet some embodiments, the shunting catheter 400 may include additional lumens for holding shunted tissue from a tissue wall.

Figure 5:
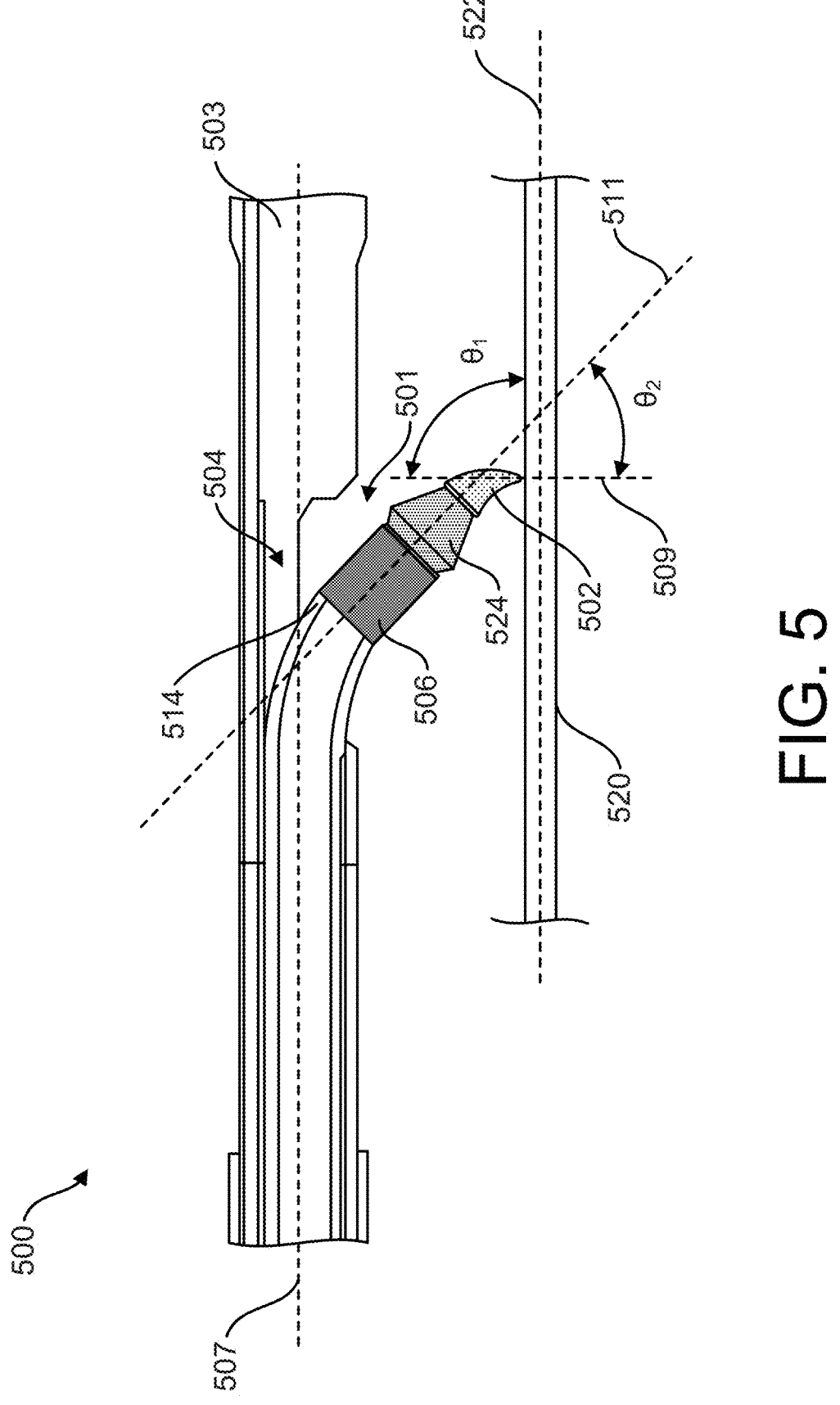
FIG. 5 is a schematic diagram of a cross-sectional view of an example of a shunting catheter and a side view of an example puncture element that is curved, in accordance with embodiments of the present disclosure.

FIG. 5 is a schematic diagram of a cross-sectional view of an example of a shunting catheter 500 and a side view of an example puncture element 502 that is curved, in accordance with embodiments of the present disclosure. The shunting catheter 500 includes a catheter shaft 503 having a shaft lumen 504, and puncture assembly 501 connected to a shunting element 506 disposed within the shaft lumen 504 at a first state (e.g., during deployment).

In some embodiments, the shunting element 506 is disposed or positioned within an expandable element sheath 514, and further within the shaft lumen 504, at a first state (e.g., before a deployment and/or during a deployment to position the puncture assembly 501). In some embodiments, the shunting element 506 is crimped when positioned within the expandable element sheath 514 at a first state. In certain embodiments, the shunting element 506 is an elongated element. The shunting element 506 may be disposed within the expandable element sheath 514 which is positioned within a shaft lumen of the catheter shaft 304 at a first state. In certain embodiments, the expandable element sheath 514 has a pre-determined curve. In some examples, the expandable element sheath 514 has a pre-determined curve for the shunting element 506 to deploy. In certain embodiments, the shunting element shaft is extended from the shaft lumen of the catheter shaft 304 at a third state (e.g., a shunting state to use the shunting element 506). In some examples, the shunting element 506 may be an expandable element (e.g., a balloon or a basket) configured to deliver ablative energy, and is expanded when the shunting element 506 is at a third state (e.g., a shunting state to use the shunting element 506).

In certain embodiments, the puncture assembly 501 is extended from the catheter shaft 503 at a second state. The puncture assembly 501 may include a dilator 524. The dilator 524 may be connected to an expandable element sheath 514 on one end, and a puncture element 502 on the other end. In some embodiments, the puncture element 502 may be configured to deliver energy, or include one or more electrodes configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall 520 of a patient) to facilitate puncturing through a tissue wall 520. In some embodiments, the dilator 524 may be configured to deliver energy, or include one or more electrodes configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall 520 of a patient).

In some embodiments, the puncture assembly 501 is positioned within the catheter shaft 503 at a first state (e.g., before a deployment and/or during a deployment to position the puncture assembly 501). In certain embodiments, a distal portion of the expandable element sheath 514 has a pre-determined curve. In some examples, the curved distal portion of the expandable element sheath 514 is directly adjacent or in close proximity with the puncture assembly 501. In certain embodiments, the expandable element sheath 514 is extended from the catheter shaft 503 at a second state (e.g., a puncturing state to puncture tissue wall 520 and/or a shunting state to use a shunting element). In certain embodiments, the expandable element sheath 514 does not have a predetermined curve, but is made of an at least semi-malleable material that may allow a physician to manipulate the distal portion of the expandable element sheath 514 into a curve. The curve of the expandable element sheath 514 may facilitate directing the puncture assembly towards a tissue wall at the second state during a puncturing procedure and/or at a third state during a shunting procedure. In certain embodiments, the puncture assembly 501, including a distal portion of the expandable element sheath 514, is extended from the catheter shaft 503 at a second state (e.g., a puncturing state to use the puncture element 502) and/or a third state (e.g., a shunting state to use a shunting element). In certain embodiments, the puncture element 502 has a predetermined curve. The curve of the puncture element 502 may bias the puncture element 502 (e.g., a tip thereof) towards the tissue wall of the patient at the second state or third state during a puncturing or shunting procedure when in use.

According to some embodiments, the catheter shaft 503 includes a shaft opening. In some embodiments, the catheter shaft 503 defines a first axis 507, and where the tip of the puncture element 502 contacts a tissue wall 520 defines a second axis 509. In certain embodiments, the second axis 509 and the first axis 507 form an angle greater than zero degrees. In certain examples, the second axis 509 and the first axis 507 form an angle greater than 30 degrees. In some embodiments, the second axis 509 and the first axis 507 form an angle proximate to 90 degrees. In some embodiments, the second axis 509 and the first axis 507 form an angle in the range of 30 degrees to 120 degrees. In some instances, the puncture element 502 includes a pre-curve formed from a semi-rigid or rigid material. The semi-rigid or rigid material of the puncture element 502 may include nitinol or stainless steel (SS) with a curve built in before deployment.

In some embodiments, the expandable element sheath 514 includes a curved portion that forms an arc connecting a first straight portion of the expandable element sheath 514 disposed inside the shaft lumen 504 and a second straight portion of the expandable element sheath 514 extended outward from the shaft lumen 504, the second straight portion of the expandable element sheath 514 adjacent the dilator 524 defines an axis 511. In some embodiments, for example as shown, the curved portion of the expandable element sheath 514 is adjacent a shaft opening. In certain embodiments, the dilator 524 is located at the end of the second straight portion of the expandable element sheath 514 and outside of the curved portion of the expandable element sheath 514. In some embodiments, the puncture element 502 includes a curve, thus having a concave shape on one side of the puncture element 502, and a convex shape on the other side of the puncture element 502. As shown, the curve of the puncture element 502 is configured to bias the tip of the puncture element 502 away from the axis 511, for example, biasing the tip of the puncture element 502 toward the tissue wall 520 when in use. In certain embodiments, the axis 509 and axis 511 defines an angle $\theta_2$. In some embodiments, the angle $\theta_2$ may be above zero degrees and below 180 degrees. In some embodiments, the angle $\theta_2$ may be above zero degrees and below 90 degrees. In certain embodiments, puncture element 502 forms an angle $\theta_1$ with respect to a tissue wall 520 when in use. In the angle $\theta_1$ may be above zero degrees and below 180 degrees, or above 45 and below 135 degrees, or above 60 and below 120 degrees, or about 75 and below 105 degrees, or around 90 degrees.

In certain embodiments, the shunting catheter 500 includes multiple compartments (e.g., lumens) for various elements to provide more targeted control during deployment. For example, the shunting catheter 500 may include an additional lumen in between the catheter shaft 503 and the expandable element sheath 514 for more precise control during deployment of the puncture assembly 501. In some embodiments, the shunting catheter 500 may include lumens for containing functional components such as a guidewire or pull wire assembly. In yet some embodiments, the shunting catheter 500 may include additional lumens for holding shunted tissue from a tissue wall.

In some embodiments, the angle between the second axis 509 and the first axis 507 may be a result of the curve in expandable element sheath 514 and a curve of puncture element 502, where the curve of the puncture element 502 further biases the puncture element 502 towards the tissue wall 520 when in use. Therefore, the angle $\theta_1$ between the second axis 509 and a third axis 522 defined by the tissue wall 520 may also result from the curve in expandable element sheath 514 and the curve of puncture element 502. When a puncture assembly is extended from a catheter shaft at a second state or a third state, the distance between an outer surface of the catheter shaft and a surface of a patient's tissue wall (e.g., an inner surface of the vessel wall of a patient) may be small enough that an expandable element sheath is prevented from curving more than a certain amount. This may result in the angle $\theta_1$ being greater than 90 degrees and preventing a tip of a puncture element from catching on, and puncturing through, the tissue wall at the intended target location. Instead, the tip of the puncture element may slide along the tissue wall before puncturing through, potentially damaging more of the tissue wall than intended and puncturing through the tissue wall at a different location than the target location. In some embodiments, the curved nature of puncture element 502 may bias the tip of puncture element 502 towards tissue wall 520 when in use, such that the angle $\theta_1$ between the second axis 509 (defined by the tip of the puncture element 502) and the third axis 522 is closer to 90 degrees. When the angle $\theta_1$ is closer to 90 degrees, puncture element 502 may more easily pierce through the tissue wall 520, preventing excess damage to the tissue wall 520 from dragging, and puncturing the tissue wall 520 more accurately at the target location.

In some embodiments, the puncture assembly 501 includes a tube (e.g., a hypotube) to support the dilator 524 and the expandable element sheath 514. The tube may include a plurality of laser cuts generally perpendicular to longitudinal axis defined by expandable element sheath 514. In some embodiments, the tube may be formed of a conductive material configured to transmit energy to one or more electrodes on the puncture assembly 501 to transmit energy to puncture tissue of a patient. In some instances, the tube is made of stainless steel or nitinol. In certain instances, the tube may further include a pull wire assembly to control the flex or angle of the expandable element sheath 514 and/or the puncture element 502 relative to the catheter shaft 503.

The pull wire assembly may be laser welded to the tube or inside the tube at a distal end of the tube. In some embodiments, the pull wire assembly may include nitinol, stainless steel (SS), cobalt, chromium, titanium, or a combination thereof. The expandable element sheath 514 may be made of a semi-rigid or rigid material to have a pre-formed angle before deployment. After the puncture assembly 501 is deployed, the pre-formed angle may be further adjusted using the pull wire assembly to further adjust and/or stabilize the contact point between the puncture element 502 and the tissue wall 520. In some embodiments, the expandable element sheath 514 may be made of a semi-malleable material, where the curve in the expandable element sheath 514 is formed in response to manipulation of the pull wire to adjust and/or stabilize the contact point between the puncture element 502 and the tissue wall 520.

In certain embodiments, during deployment, the guidewire may be used to guide the shunting catheter into the CS of a patient. In yet certain embodiments, the guidewire may be used to indicate the location of the shunting catheter including one or more of the components (e.g., the puncture assembly, the shaft opening of the catheter 500, etc.) in the CS of a patient.

Figure 6:
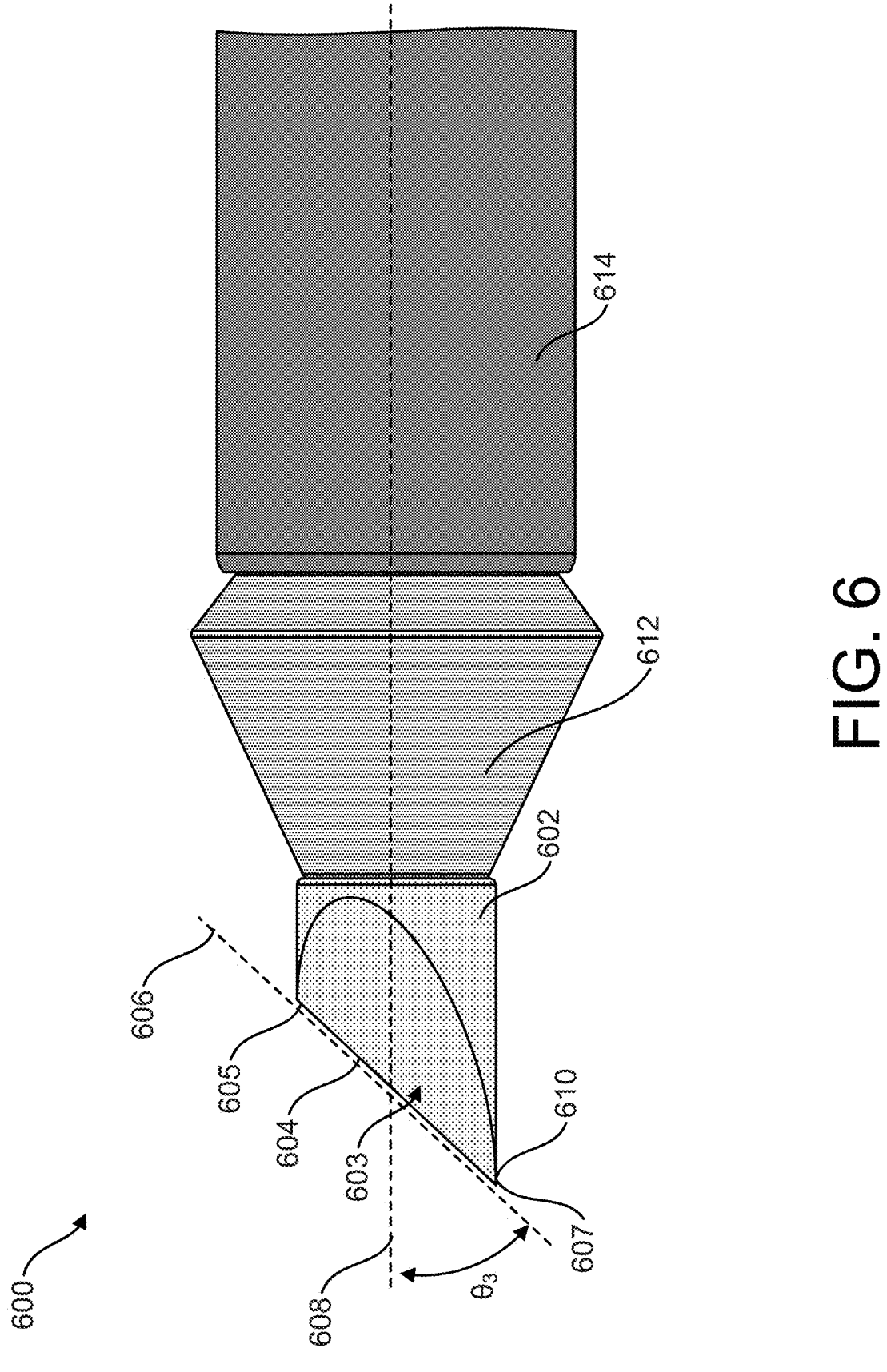
FIG. 6 is a schematic diagram illustrating an example of a puncture assembly, in accordance with embodiments of the present disclosure.

FIG. 6 is a schematic diagram illustrating an example of a puncture assembly 600, in accordance with embodiments of the present disclosure. As shown, the puncture assembly 600 includes a puncture element 602, a dilator 612, and a distal portion of an expandable element sheath 614. According to some embodiments, dilator 612 and expandable element sheath 614 may define one or more lumens, in which a hypotube may be disposed. The puncture element 602 may define a first axis 608. In some embodiments, first axis 608 may be coincident with a longitudinal axis defined by one or more of the puncture assembly 600, the dilator 612, and/or the puncture element 602.

According to certain embodiments, as shown, puncture element 602 includes a tip 610 defining a distal point of the puncture element 602, and a blade section 603. In some embodiments, the blade section 603 includes a first end 607, a second end 605, and a line 606 that is angled with respect to the first axis 608. In some embodiments, the first end 607, second end 605, and line 606 defines a blade edge 604 along the line 606. In some embodiments, the first end 607 of the blade edge 604 is the tip 610 of the puncture element 602. In certain embodiments, the blade section 603 has a tapered shape and includes a blade edge 604. For example, the blade section 603 has a distal end at the blade edge 604 and a proximal end close to the dilator 612, with the proximal end having a first thickness and the distal end having a second thickness, where the second height is smaller than the first thickness. In certain embodiments, the blade section includes two flat surfaces, where the intersection of the two flat surfaces (e.g., along the line 606) defines the blade edge 604, and a curved surface surrounding the two flat surfaces (see e.g., FIG. 9B).

In some embodiments, the puncture element 602 may be configured to deliver energy. or includes one or more electrodes configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall of a patient).

In some embodiments, the angle $\theta_3$ formed between the line 606 and the first axis 608 may be between 0 and 90 degrees. In some examples, the angle $\theta_3$ formed between the line 606 and the first axis 608 may be between 10 and 90 degrees. In some examples, the angle $\theta_3$ formed between the line 606 and the first axis 608 may be between 10 and 80 degrees. In some examples, the angle $\theta_3$ formed between the line 606 and the first axis 608 may be between 10 and 70 degrees.

In some instances, the material of any one or more of the puncture element 602, dilator 612, and/or expandable element sheath 614 may show up under fluoroscopy. In yet some instances, the material of any one or more of the puncture element 602, dilator 612, and/or expandable element sheath 614 may include a radiopaque marker added for visualization. The radiopaque marker may include tantalum, gold, or any radiopaque marker known by a skilled person in the art. In some instances, the material of one or more of the puncture element 602, the dilator 612, and/or the expandable element sheath 614 may include nitinol or SS.

Figure 7A:
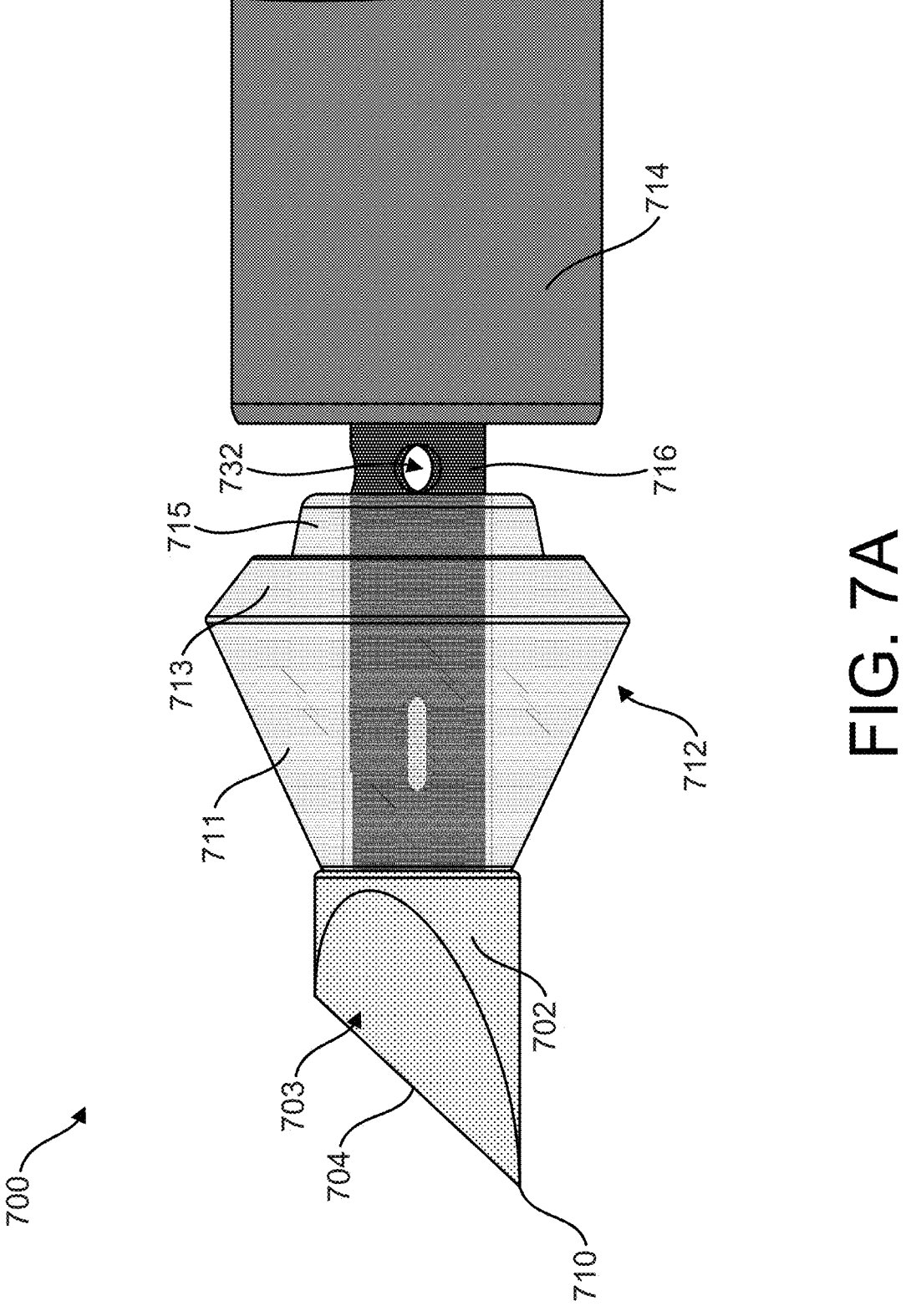
FIGS. 7A-7B are schematic diagrams of side views of an example of a puncture assembly, in accordance with embodiments of the present disclosure.
Figure 7B:
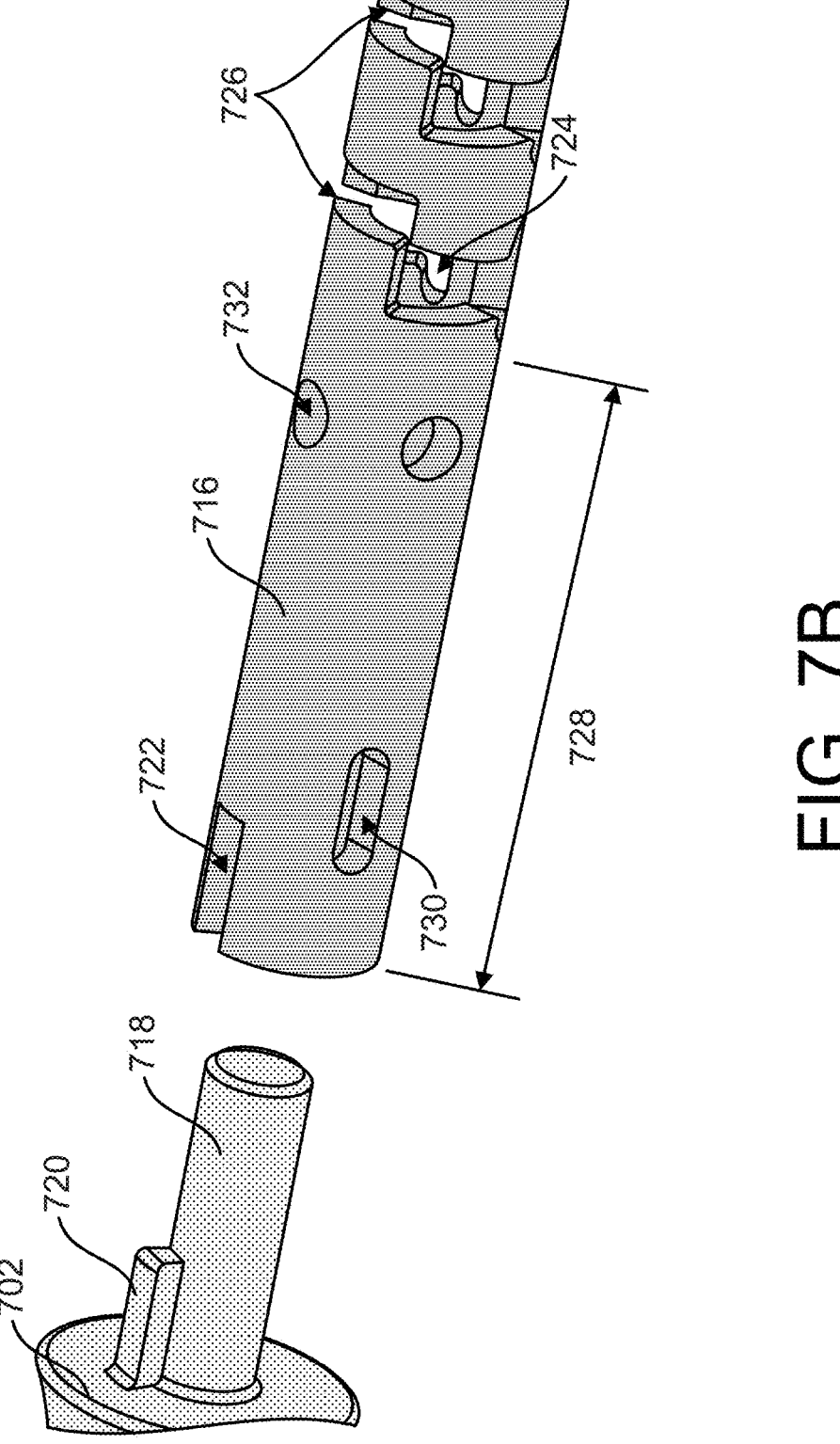

FIGS. 7A-7B are schematic diagrams of side views of an example of a puncture assembly 700, in accordance with embodiments of the present disclosure. As shown, the puncture assembly 700 includes a puncture element 702, a dilator 712, a distal portion of an expandable element sheath 714 and a distal portion of a hypotube 716. In some embodiments, the hypotube 716 may act as a core to support the dilator 712 and the expandable element sheath 714. Dilator 712 and expandable element sheath 714 may include one or more interior lumens, in which hypotube 716 is disposed. As shown in FIG. 7A, dilator 712 is shown as semi-transparent in order to better visualize hypotube 716.

According to some embodiments, as shown, puncture element 702 includes a tip 710 defining a distal point of the puncture element 702, and a blade section 703. In some embodiments, the blade section 703 of the puncture element 702 has a tapered shape and includes a blade edge 704. For example, the blade section 703 has a distal end at the blade edge 704 and a proximal end close to the expandable element sheath 714, with the blade section 703 at the proximal end having a first thickness and the blade section at the distal end having a second thickness, where the second thickness is smaller than the first thickness. In some embodiments, a distal end of the blade edge 704 is the tip 710 of the puncture element 702. In certain embodiments, the blade section 703 includes two flat surfaces, where the intersection of the two flat surfaces defines the blade edge 704, and a curved surface surrounding the two flat surfaces (see e.g., FIG. 9B).

In some embodiments, the puncture element 702 may be configured to deliver energy, or include one or more electrodes configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall of a patient).

According to certain embodiments, the dilator 712 is formed as part of the puncture element 702. In some embodiments, the dilator 712 is formed as a proximal portion of the puncture element 702. In certain embodiments, the puncture element 702 is formed of a conductive material configured to transmit ablation energy to tissue of a patient. In certain examples, the dilator 712 is formed of a conductive material configured to transmit ablation energy to tissue of a patient. In some embodiments, the dilator 712 may include nitinol, stainless steel (SS), cobalt, chromium, titanium, or a combination thereof. In certain examples, one or more of the puncture element 702 and the dilator 712 are formed of a conductive material configured to transmit ablation energy to the tissue of a patient. In certain examples, the dilator 712 is formed of a non-conductive material configured to insulate expandable element sheath 714 from the puncture element 702. In some embodiments, the dilator 712 may include a polymer material, for example, machine Acrylonitrile Butadiene Styrene (ABS), Polyoxymethylene (POM) (e.g., Delrin®), Poly(ether-b-amide) copolymers (e.g., PEBAX®), Polyamide (e.g., nylon), Polytetrafluoroethylene (PTFE), lubricious PTFE (e.g., Teflon™), Polyether ether ketone (PEEK) or a combination thereof. In certain embodiments, the dilator 712 is injected molded out of the same of similar materials as the puncture element 702. In certain embodiments, the dilator 712 is injected molded out of polymer material, ABS, POM, Poly(ether-b-amide) copolymers, Polyamide, lubricious PTFE, PEEK or a combination thereof. In certain examples, the puncture element 702 is formed of a non-conductive material. In certain embodiments, the hypotube 716 may be formed of a conductive material configured to transmit ablation energy to one or more of the puncture element and/or the dilator 712. In certain examples, the hypotube 716 may be formed of a conductive material configured to transmit ablation energy from a proximal end of the shunting catheter to one or more of the puncture element 702 and the dilator 712. In certain examples, the hypotube 716 extends within the shunting catheter from a proximal end of the shunting catheter to the puncture element 702. In certain embodiments, the expandable element sheath 714 may be configured to insulate the hypotube 716. In certain examples, the expandable element sheath 714 may be formed of a non-conductive material to insulate the hypotube 716.

The hypotube 716 may include a plurality of laser cuts 726 generally perpendicular to a longitudinal axis defined by hypotube 716. In some embodiments, at least some of the plurality of laser cuts 726 may be non-perpendicular to the longitudinal axis defined by the hypotube 716. In certain embodiments, the hypotube 716 includes a distal portion 728 devoid of laser cuts 726. In certain examples, the distal portion 728 of the hypotube 716 may be disposed primarily within a lumen defined by the dilator 712. In certain embodiments, the distal portion 728 may include a slot 722 configured to receive a keying feature 720 of puncture element 702. Keying feature 720 of puncture element 702 may be configured to fit within slot 722. The pin 718 of puncture element 702 may be configured to fit within hypotube lumen 724 through an opening on a distal end of hypotube 716. In some embodiments, the puncture element 702 may be welded to the hypotube 716. In some instances, the pin 718 and/or the keying feature 720 may be welded within hypotube 716. In some embodiments, the distal portion 728 of the hypotube 716 may include a weld port 730 (e.g., a hole through a thickness of the hypotube 716) through which the pin 718 may be welded to the inside of the hypotube 716.

In some embodiments, the distal portion 728 of the hypotube 716 may include a lumen port 732 for pulling blood from a patient's vessel. In certain embodiments, location of the puncture element 702 may be determined by pulling blood from a patient's vessel to detect oxygen level and/or pressure, then comparing the detected oxygen level and/or pressure with anticipated values for certain locations within a patient's vessel/heart chambers. In certain embodiments, the lumen port 732 may be used for pulling blood from a patient's vessel, then using the pulled blood for confirming that the puncture element 702 is located within a patient's left heart chamber. In some embodiments, the lumen port 732 may be used for shooting contrast dye into the catheter shaft, and using contrast imaging to determine location of the puncture element 702 and/or the dilator 712 within a patient's vessel/heart chambers. In some embodiments, the lumen port 732 may be used for flushing the system during the procedure.

In some instances, the hypotube 716 is made of stainless steel or nitinol, and may further include a pull wire assembly to control the flex or angle of the hypotube 716 along the plurality of laser cuts 726. The pull wire assembly may be laser welded to the hypotube 716 or inside the hypotube 716 at a distal end of the hypotube 716. In some embodiments, the pull wire assembly may be disposed within hypotube lumen 724 defined by the hypotube 716. In some embodiments, the pull wire assembly may be laser welded to a proximal end of pin 718 of puncture element 702. In some embodiments, the pull wire assembly may include nitinol, stainless steel (SS), cobalt, chromium, titanium, or a combination thereof.

In some embodiments, the dilator 712 may include a distal portion 711, a proximal portion 713, and a step portion 715. The distal portion 711 and the proximal portion 713 may both define frustocones. The frustoconical distal portion 711 may connect to the frustoconical proximal portion at a joint surface defining the largest diameter of the dilator 712. An exterior surface of the dilator 712 may be smooth. The dual frustoconical shapes of the dilator 712 may allow the dilator to smoothly dilate a puncture hole through patient tissue as the dilator 712 is extended distally through the puncture hole or withdrawn proximally through the puncture hole. The distal end of the dilator 712 may define a diameter roughly equal to a diameter defined by the puncture element 702 where the distal end of the dilator 712 contacts the puncture element 702.

The step portion 715 of the dilator 712 may be configured to center and seat a distal end of the expandable element sheath 714. In certain embodiments, a distal end of the dilator 712 may define a distal end of distal portion 711. The distal end of the dilator 712 may abut or connect to a proximal end of puncture element 702.

Figure 8:
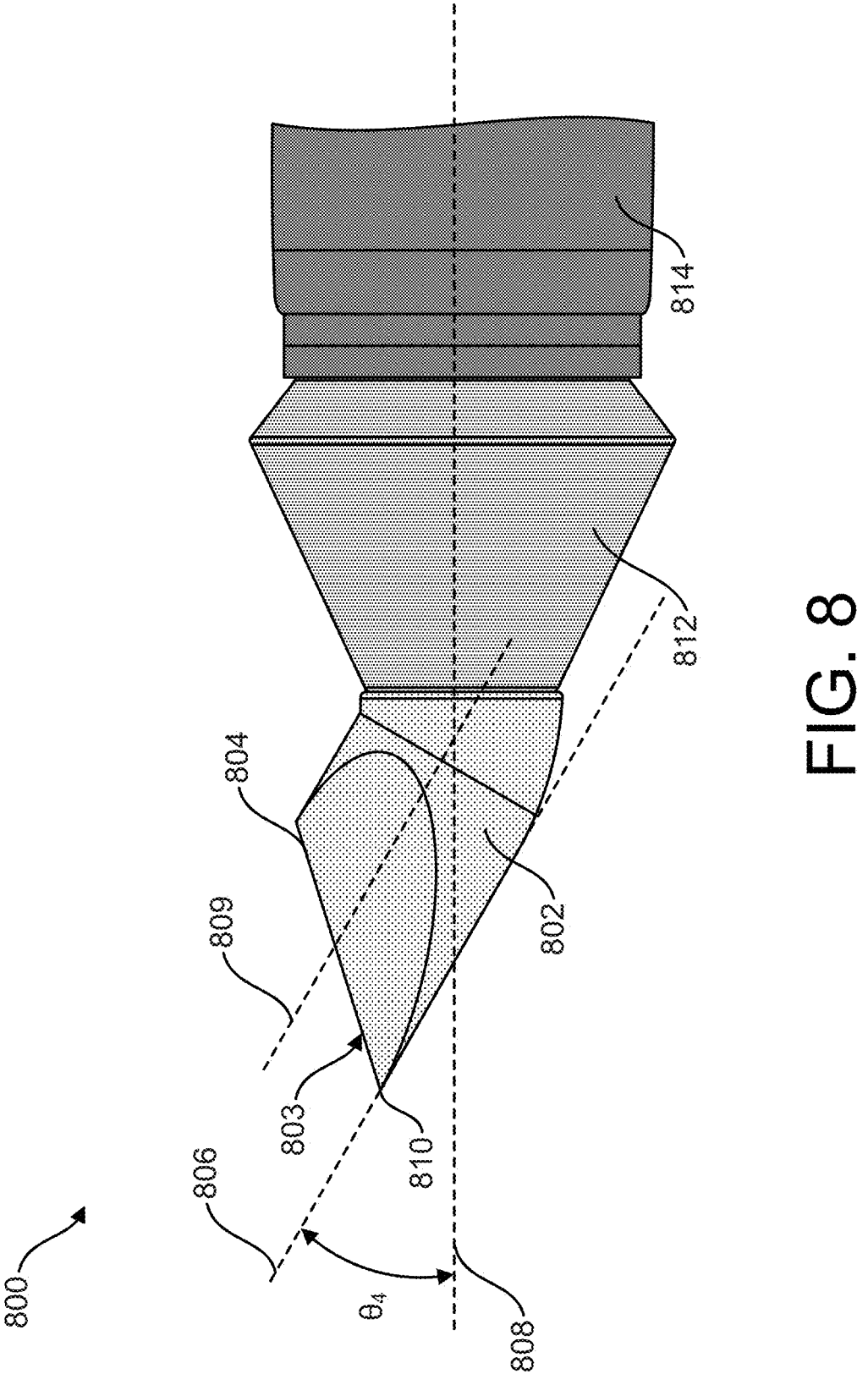
FIG. 8 is a schematic diagram of a side view of an example of a puncture assembly having a curved puncture element, in accordance with embodiments of the present disclosure.

FIG. 8 is a schematic diagram of a side view of an example of a puncture assembly 800 having a curved puncture element 802, in accordance with embodiments of the present disclosure. As shown, the puncture assembly 800 includes the puncture element 802, a dilator 812, and a distal portion of an expandable element sheath 814. The puncture element 802 includes tip 810. In some embodiments, as shown, the puncture element 802 may be curved. The curve of the puncture element 802 may bias the tip 810 and/or a blade section 803 of the puncture element 802 towards a tissue wall of a patient when in use (e.g., during a puncturing or shunting procedure). In some embodiments, the blade section 803 of the puncture element 802 may include a blade edge 804.

According to certain embodiments, the curved puncture element 802 defines a first axis 808 and a second axis 806. In some embodiments, the body of the puncture element 802 may define the first axis 808. In some embodiments, the first axis 808 may be coincident with a longitudinal axis defined by one or more of the puncture assembly 800, the dilator 812, the puncture element 802, and/or a distal portion of a hypotube core (e.g., the distal portion 728 of the hypotube 716 of FIGS. 7A-7B). In some embodiments, the first axis 808 may be defined by a longitudinal axis of a proximal portion of the puncture element 802. In some embodiments, the first axis 808 may be defined by a longitudinal axis of a pin (e.g., pin 718 of FIG. 7B) of the puncture element 802. In some embodiments, the first axis 808 may be defined perpendicular to a proximal surface of the puncture element 802 (e.g., the surface of the puncture element 802 which abuts the dilator 812). In some embodiments, the body of the puncture element 802 may define the second axis 806. In some embodiments, the second axis 806 may be defined by the tip 810 of the puncture element 802. As shown in FIG. 8, second axis 806 passes through the tip 810 and extends along an external surface of the puncture element 802 in a longitudinal direction with respect to a distal portion of the puncture element 802. In some embodiments, a distal portion of the puncture element 802 may define a generally cylindrical shape and the second axis 806 may trace a generatrix defined by the generally cylindrical shape. In some embodiments, a longitudinal axis 809 of a distal portion of the puncture element 802 (e.g., a blade section) may define the second axis 806 (e.g., the second axis may be coincident with the longitudinal axis 809). As shown in FIG. 8, The first axis 808 and the second axis 806 may define the angle $\theta_4$ greater than zero degrees. In some embodiments, the angle $\theta_3$ between the first axis 808 and the second axis 806 may be between 0 and 180 degrees. In some embodiments, the angle $\theta_3$ may be between 10 and 90 degrees.

According to certain embodiments, as shown, the tip 810 of the puncture element 802 defines a distal point of the puncture element 802. In some embodiments, the angle $\theta_4$ between the first axis 808 and the second axis 806 is configured to bias the tip 810 towards a tissue wall of a patient when in use (e.g., during a shunting procedure). In some embodiments, the puncture assembly 800 may be disposed within the lumen of a catheter shaft at a first state (e.g., before a deployment and/or during the deployment to position the puncture assembly 800), wherein an opening in the catheter shaft is located above the puncture assembly 800 with respect to the example of FIG. 8. When the puncture assembly 800 is extended from the catheter shaft through the opening at a second state (e.g., a puncturing state to puncture the tissue wall) and/or a third state (e.g., a shunting state to perform shunting), the angle $\theta_4$ may be above zero degrees and below 180 degrees such that the tip 810 is biased toward the tissue wall surrounding the catheter shaft when in use.

As shown in FIG. 8, the curve of the puncture element 802 defines an abrupt pivot between the first axis 808 and the longitudinal axis 809. A proximal portion of the puncture element 802 primarily defines a single longitudinal axis coincident with first axis 808. A distal portion of the puncture element 802 primarily defines a single longitudinal axis 809 (which may be coincident with second axis 806 in certain embodiments). The longitudinal axis defined by the proximal portion of the puncture element 802 and the longitudinal axis 809 may intersect at a point that lies within the interior of the puncture element 802, wherein the intersect point is located in close proximity to a center of a shape defined by a cross-section of the puncture element 802 that includes the intersect point.

Figure 9A:
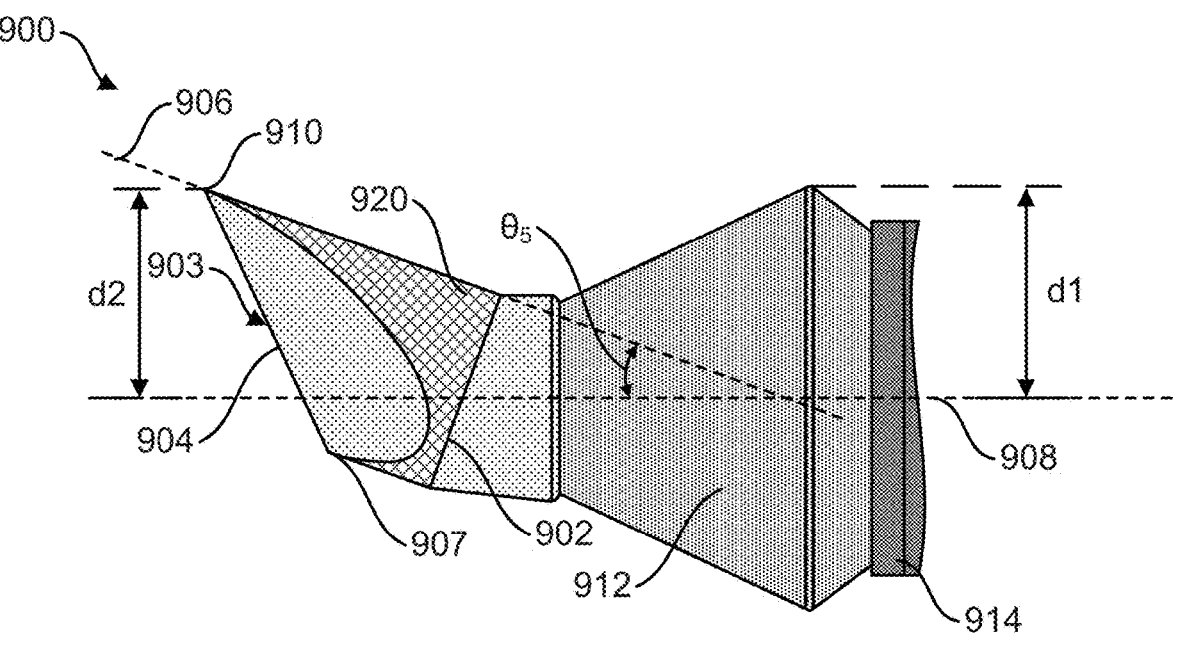
FIGS. 9A-9B are schematic diagrams of a side view and a front view, respectively, of an example of a puncture assembly having a puncture element with a single blade edge, in accordance with embodiments of the present disclosure.
Figure 9B:
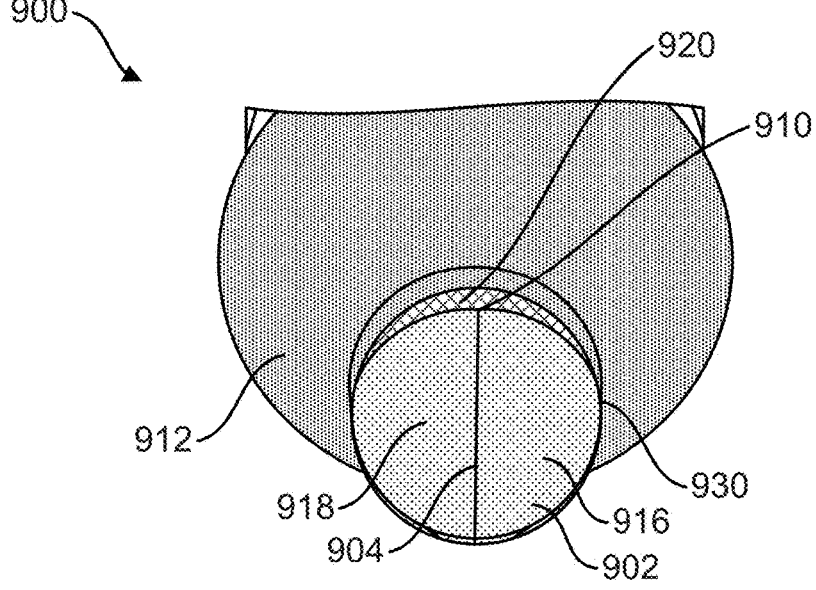

FIGS. 9A-9B are schematic diagrams of a side view and a front view, respectively, of an example of a puncture assembly 900 having a puncture element 902 with a blade section 903 having a single blade edge 904, in accordance with embodiments of the present disclosure. As shown, the puncture assembly 900 includes a puncture element 902, a dilator 912, and a distal portion of an expandable element sheath 914.

According to some embodiments, for example as shown in FIG. 9B, the blade section 903 of the puncture assembly 900 includes a first flat surface 916 and a second flat surface 918. In some embodiments, the intersection of the flat surface 916 and the flat surface 918 defines the blade edge 904. For example, the blade section 903 has a distal end at the blade edge 904 and a proximal end close to the expandable element sheath 914, with the blade section 903 at the proximal end having a first thickness and the blade section 903 at the distal end having a second thickness, where the second thickness is smaller than the first thickness. In some embodiments, a distal end of the blade edge 904 is the tip of the puncture element. In certain embodiments, the blade section 903 further includes a curved surface 920 surrounding the two flat surfaces 916 and 918.

In some embodiments, the puncture element 902 may be configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall of a patient).

According to certain embodiments, a longitudinal axis of the dilator 912 may define a first axis 908. In certain embodiments, the puncture assembly 900 may be disposed within the lumen of a catheter shaft at a first state (e.g., before a deployment and/or during a deployment to position the puncture assembly 900 at a target location in a patient's body). In some embodiments, the catheter shaft may define a longitudinal axis substantially coincident with first axis 908 at the first state. In some embodiments, a portion of the dilator 912 that is furthest away from first axis 908 may define a first distance d1 from the first axis 908. The first distance d1 may be smaller than an interior radius of the lumen of the catheter, so that the dilator 912 can be disposed within the lumen of the catheter. In some embodiments, a portion of the puncture element 902 furthest away from the first axis 908 (e.g., tip 910) defines a second distance d2 from the first axis 908. In some embodiments, second distance d2 may be smaller than an interior radius of the lumen of the catheter, so that the puncture element 902 can be disposed within the lumen of the catheter. Second distance d2 may be less than or equal to the first distance d1.

According to certain embodiments, the puncture element 902 may be curved. The curve may bias the tip 910 towards a tissue wall of a patient when in use. In some embodiments, the curve of puncture element 902 may define a first axis (e.g., a longitudinal axis of a proximal portion of the puncture element coincident with first axis 908), and a second axis 906. In some embodiments, the tip 910 defines the second axis 906. As shown in FIG. 9A, the second axis 906 passes through the tip 910 and extends along an external surface of the puncture element 902 in a longitudinal direction with respect to a distal portion of the puncture element 902. In some embodiments, an angle $\theta_5$ between the first axis 908 and the second axis 906 biases the tip 910 towards a tissue wall of a patient when in use. In some examples, the angle $\theta_5$ is between zero and 90 degrees.

According to certain embodiments, as shown, puncture element 902 includes a tip 910 defining a distal point of the puncture element 902, and a blade edge 904. The blade edge 904 may define a first end 907, and a second end. In some embodiments, as shown in FIGS. 9A-9B, the second end of the blade edge 904 is the tip 910 of the puncture element 902. In some embodiments, the cross section of a distal portion of the puncture element 902 may define a perimeter 930 of a shape. In some examples, as shown in FIG. 9B, the shape may be substantially circular. In some embodiments, the first end 907 of the blade edge 904 is coincident with a first point on the perimeter 930 of the shape. In some embodiments, the second end of the blade edge is coincident with a second point on the perimeter 930. In some embodiments, the first end 907 and the second end of the blade edge 904 are coincident with points on opposite sides of the shape defined by the cross section, and the blade edge 904 bisects the shape. In some embodiments, the first end 907 and the second end of the blade edge 904 are coincident with any two separate points on the perimeter 930 of the shape defined by the cross section of the distal portion of the puncture element 902, and the blade edge spans between the two separate points.

Figure 10:
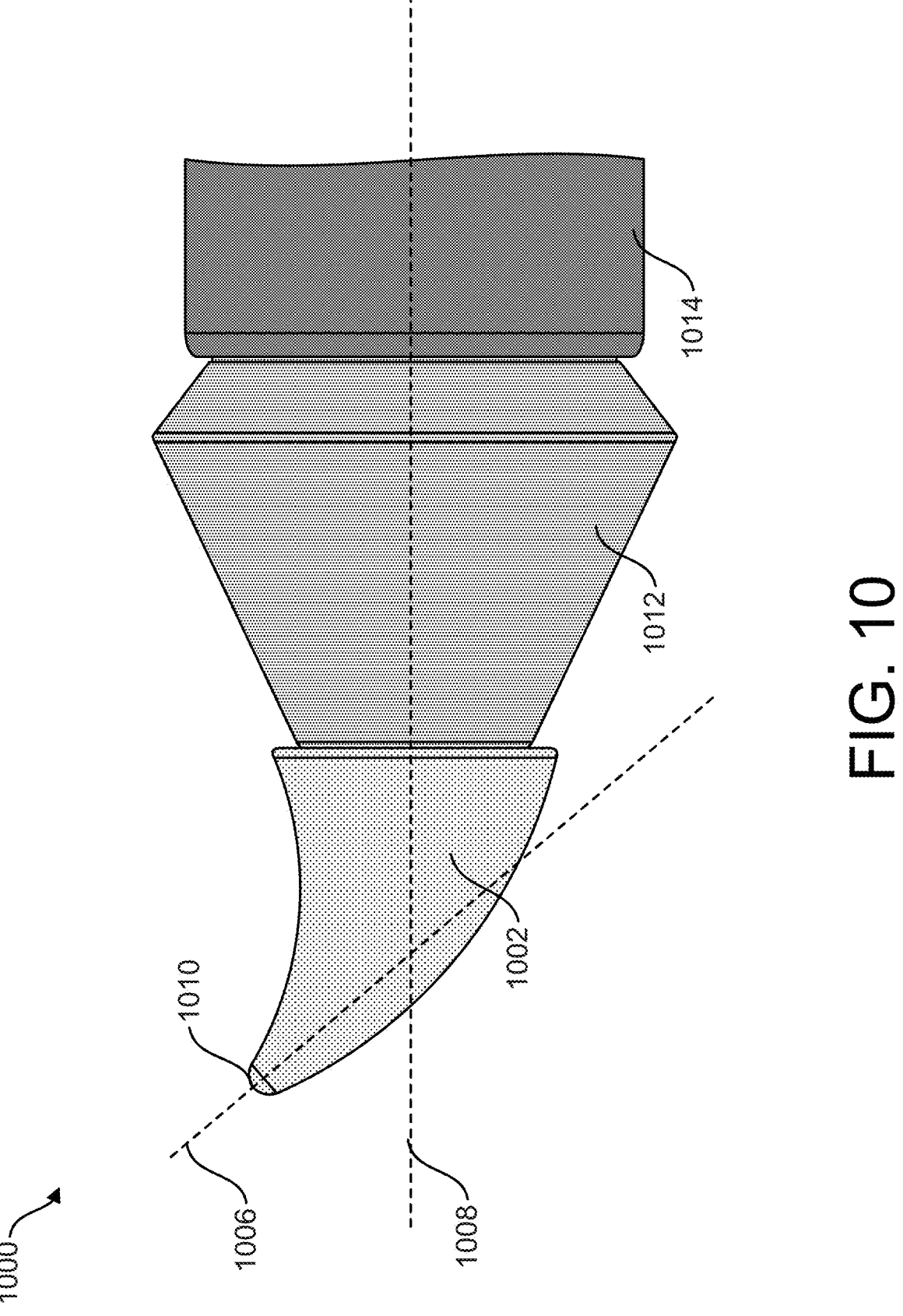
FIG. 10 is a schematic diagram of a side view of an example of a puncture assembly having a curved, conical puncture element, in accordance with embodiments of the present disclosure.

FIG. 10 is a schematic diagram of a side view of an example of a puncture assembly 1000 having a curved, conical puncture element 1002, in accordance with embodiments of the present disclosure. As shown, the puncture assembly 100 includes a puncture element 1002, a dilator 1012, and a distal portion of an expandable element sheath 1014.

The puncture assembly 1000 may define a first axis 1008. In some embodiments, the first axis 1008 may be coincident with a longitudinal axis defined by one or more of the puncture assembly 1000, the dilator 1012, and/or the distal portion of the expandable element sheath 1014. In some embodiments, the first axis 1008 may be defined by a proximal portion of the puncture element 1002. In some embodiments, the first axis 1008 may be defined by a longitudinal axis of a proximal portion of the puncture element 1002. In some embodiments, the first axis 1008 may be defined by a longitudinal axis of a pin (e.g., pin 718 of FIG. 7B) of the puncture element 1002. In some embodiments, the first axis 1008 may be defined perpendicular to a proximal surface of the puncture element 1002 (e.g., the surface of the puncture element 1002 which abuts the dilator 1012).

According to certain embodiments, the body of the puncture element 1002 may define the second axis 1006. In some embodiments, the second axis 1006 may be defined by the tip 1010 of the puncture element 1002. As shown in FIG. 10, the second axis 1006 passes through the tip 1010 and defines a longitudinal axis of the puncture element 1002 at the tip 1010. As shown, the puncture element 1002 defines a conical shape, wherein the distal tip 1010 of the puncture element 1002 is a tip of the conical shape. In some embodiments, the distal tip 1010 is a blunted tip. In some examples, the distal tip 1010 has a rounded shape that defines a radius of one to thirty thousandths of an inch. In some examples, the distal tip 1010 defines a radius of five to ten thousandths of an inch. In certain examples, the distal tip 1010 is a blunted tip defining a radius of from about five to about thirty thousandths of an inch, or from about ten to about thirty thousandths of an inch, or from about fifteen to about thirty thousandths of an inch. In certain examples, the distal tip 1010 is a blunted tip defining a radius of from about 0.0254 to about 0.762 millimeters, or from about 0.254 to about 0.762 millimeters, or from about 0.381 to about 0.762 millimeters. In some examples, the distal tip 1010 defines a radius of from about 0.127 to about 0.254 millimeters. In some embodiments, the distal tip 1010 is a blunted tip configured to tent (e.g. push against without puncturing through) a tissue wall at a target location to locate the puncture element and/or confirm a location of the distal tip and/or a direction the distal tip is contacting the tissue wall before puncturing. Tenting before puncturing may help the physician or operator to locate the tip 1010 of the puncture element 1002 and ensure that the puncturing is at the intended location before applying ablative energy. In some embodiments, tenting may be used together with ultrasound techniques (e.g., by taking an echocardiogram of a patient's heart) to locate where the tip is contacting the tissue.

According to certain embodiments, as shown, the puncture element 1002 may be curved. The curve may bias the tip 1010 towards a tissue wall of a patient when in use. In some embodiments, an angle between the first axis 1008 and the second axis 1006 biases the tip 1010 towards a tissue wall of a patient when the puncture element 1002 is in use. This may be the case if a tissue wall of a patient were above the puncture assembly 1000 with respect to FIG. 10. In some examples, the angle is between zero and 90 degrees. In some examples, the angle is between 10 and 90 degrees.

As shown in FIG. 10, the curve of the puncture element 1002 defines a smooth transition between the first axis 1008 and the second axis 1006. In some embodiments, the longitudinal axis defined by the puncture element 1002 along a length of the puncture element 1002 may gradually shift from the first axis 1008 to the second axis 1006 through the angle between the first axis 1008 and the second axis 1006.

Figure 11A:
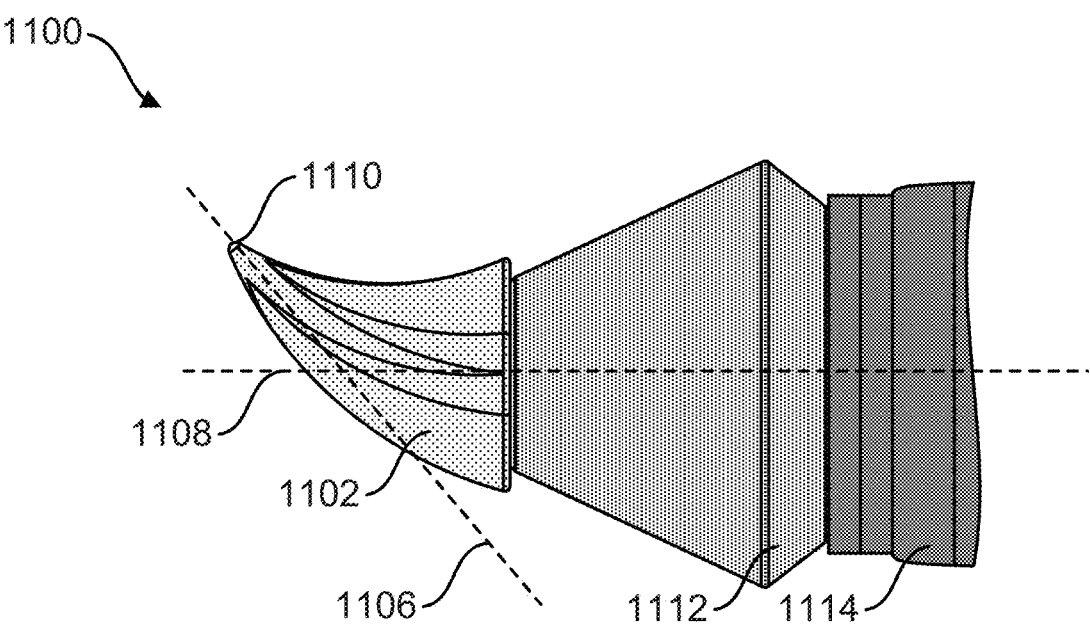
FIGS. 11A-11B are schematic diagrams of a side view and a front view, respectively, of an example of a puncture assembly having a curved, arrowhead puncture element, in accordance with embodiments of the present disclosure.
Figure 11B:
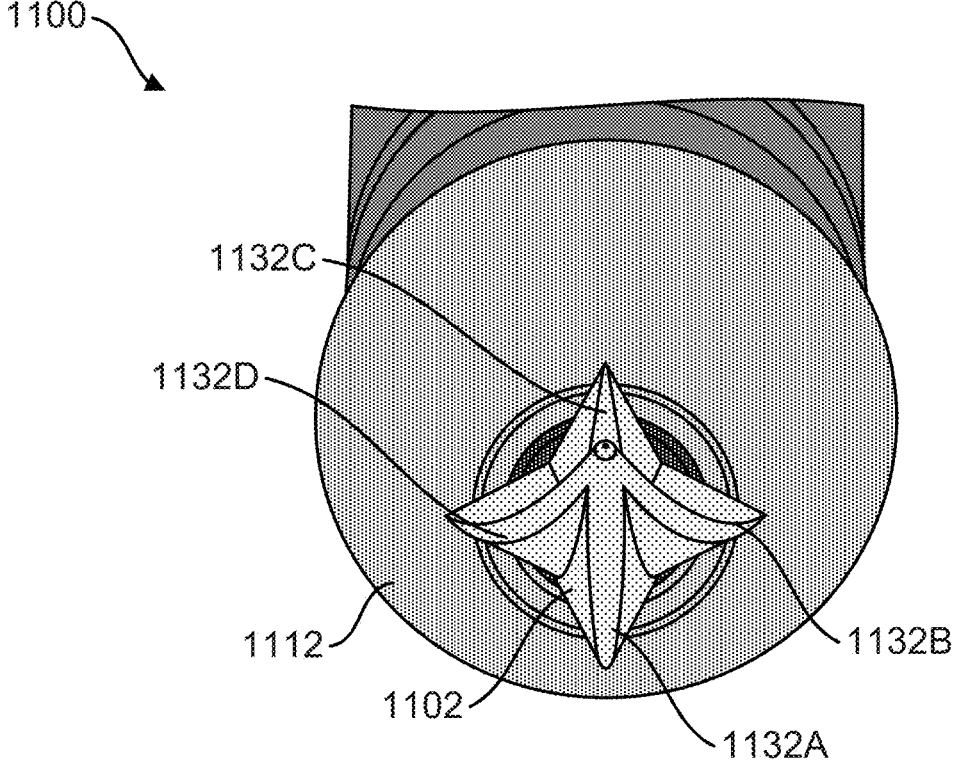

FIGS. 11A-11B are schematic diagrams of a side view and a front view, respectively, of an example of a puncture assembly 1100 having a curved, arrowhead puncture element 1102, in accordance with embodiments of the present disclosure. As shown, the puncture assembly 1100 includes a puncture element 1102, a dilator 1112, and a distal portion of an expandable element sheath 1114.

The puncture assembly 1100 may define a first axis 1108. In some embodiments, the first axis 1108 may be coincident with a longitudinal axis defined by one or more of the puncture assembly 1100, the dilator 1112, and/or the distal portion of the expandable element sheath 1114. In some embodiments, the first axis 1108 may be defined by a proximal portion of the puncture element 1102. In some embodiments, the first axis 1108 may be defined by a longitudinal axis of a proximal portion of the puncture element 1102. In some embodiments, the first axis 1108 may be defined by a longitudinal axis of a pin (e.g., pin 718 of FIG. 7B) of the puncture element 1102. In some embodiments, the first axis 1108 may be defined perpendicular to a proximal surface of the puncture element 1102 (e.g., the surface of the puncture element 1102 which abuts the dilator 1112).

According to certain embodiments, the body of the puncture element 1102 may define the second axis 1106. In some embodiments, the second axis 1106 may be defined by the tip 1110 of the puncture element 1102. As shown in FIGS. 11A-11B, the second axis 1106 passes through the distal tip 1110 and defines a longitudinal axis of the puncture element 1102 at the distal tip 1110. As shown, the puncture element 1102 is formed in the shape of a curved arrowhead comprising four protruding leaves 1132A-1132D, wherein the distal tip 1110 of the puncture element 1102 is a tip of the curved arrowhead. In some embodiments, the arrowhead may have any number of protruding leaves. In some examples, the distal tip 1110 defines a radius of one to thirty thousandths of an inch. In some examples, the distal tip 1110 defines a radius of five to ten thousandths of an inch. In certain examples, the distal tip 1110 is a blunted tip defining a radius of from about 0.0254 to about 0.762 millimeters, or from about 0.254 to about 0.762 millimeters, or from about 0.381 to about 0.762 millimeters. In some examples, the distal tip 1110 defines a radius of from about 0.127 to about 0.254 millimeters.

According to certain embodiments, as shown, the puncture element 1102 may be curved. The curve may bias the tip 1110 towards a tissue wall of a patient when the puncture element 1102 is in use. In some embodiments, an angle between the first axis 1108 and the second axis 1106 biases the tip 1110 towards a tissue wall of a patient when the puncture element 1102 is in use. This may be the case if a tissue wall of a patient were above the puncture assembly 1100 with respect to FIG. 11A. In some examples, the angle is between zero and 90 degrees. In some examples, the angle is between 10 and 90 degrees.

As shown in FIGS. 11A-11B, the curve of the puncture element 1102 defines a smooth transition between the first axis 1108 and the second axis 1106. In some embodiments, the longitudinal axis defined by the puncture element 1102 along a length of the puncture element 1102 may gradually shift from the first axis 1108 to the second axis 1106 through the angle between the first axis 1108 and the second axis 1106.

Figure 12A:
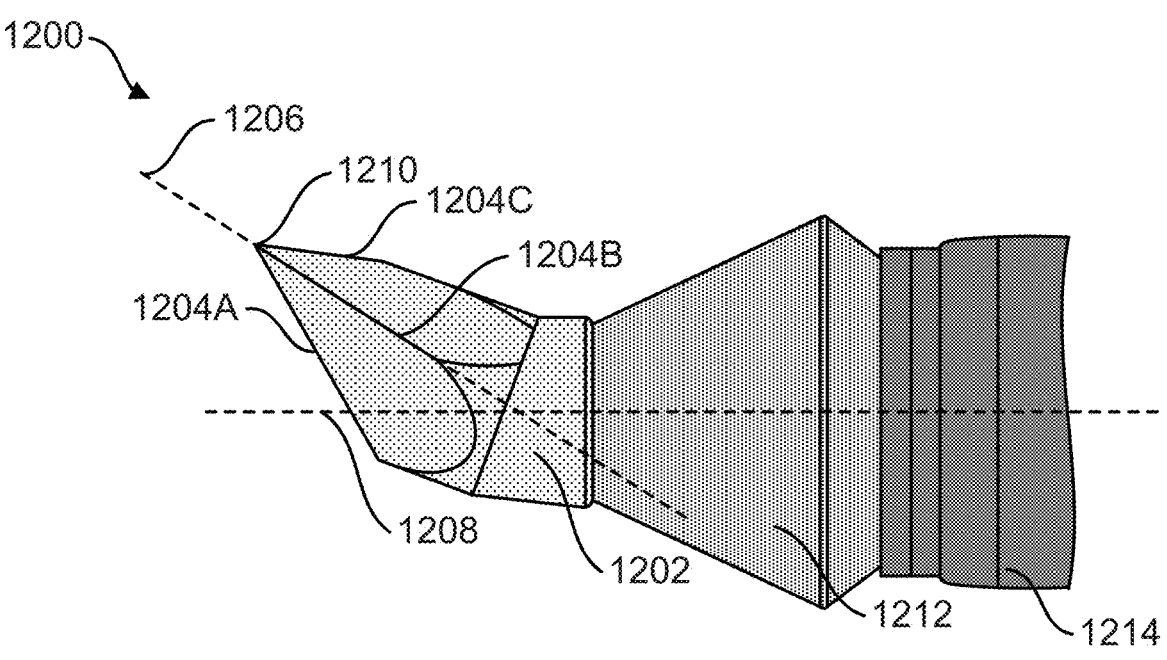
FIGS. 12A-12B are schematic diagrams of a side view and a front view, respectively, of an example of a puncture assembly having a curved puncture element with multiple blade edges, in accordance with embodiments of the present disclosure.
Figure 12B:
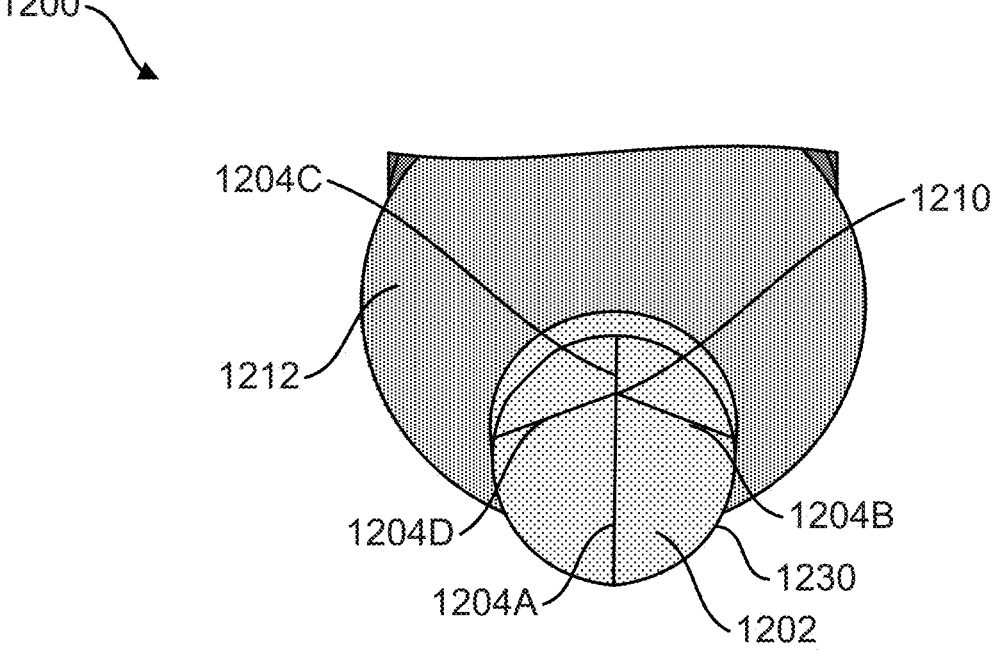

FIGS. 12A-12B are schematic diagrams of a side view and a front view, respectively, of an example of a puncture assembly 1200 having a curved puncture element 1202 with multiple blade edges 1204A-1204D, in accordance with embodiments of the present disclosure. As shown, the puncture assembly 1200 includes a puncture element 1202, a dilator 1212, and a distal portion of an expandable element sheath 1214.

The puncture assembly 1200 may define a first axis 1208. In some embodiments, the first axis 1208 may be coincident with a longitudinal axis defined by one or more of the puncture assembly 1200, the dilator 1212, and/or the distal portion of the expandable element sheath 1214. In some embodiments, the first axis 1208 may be defined by a proximal portion of the puncture element 1202. In some embodiments, the first axis 1208 may be defined by a longitudinal axis of a proximal portion of the puncture element 1202. In some embodiments, the first axis 1208 may be defined by a longitudinal axis of a pin (e.g., pin 718 of FIG. 7B) of the puncture element 1202. In some embodiments, the first axis 1208 may be defined perpendicular to a proximal surface of the puncture element 1202 (e.g., the surface of the puncture element 1202 which abuts the dilator 1212).

According to certain embodiments, the body of the puncture element 1202 may define the second axis 1206. In some embodiments, the second axis 1206 may be defined by the tip 1210 of the puncture element 1202. As shown in FIGS. 12A-12B, the second axis 1206 passes through the tip 1210 and extends parallel to a projection of a blade edge 1204B projected onto the side view plane. As shown, the puncture element 1202 includes a plurality of blade edges 1204A-1204D. In some embodiments, the puncture element 1202 may have any number of blade edges 1204A-1204D. In some embodiments, the tip 1210 of the puncture element 1202 defines a distal point of the puncture element 1202. In some embodiments, as shown, the distal tip 1210 is a first end of each of blade edges 1204A-1204D. The plurality of blade edges 1204A-1204D define a plurality of blade lengths. In some examples, each of the plurality of blade lengths are the same. In some examples, one or more of the plurality of blade lengths are different.

According to certain embodiments, as shown, the puncture element 1202 may be curved. The curve may bias the tip 1210 towards a tissue wall of a patient when the puncture element 1202 is in use. In some embodiments, an angle between the first axis 1208 and the second axis 1206 biases the tip 1210 towards a tissue wall of a patient when the puncture element 1202 is in use. This may be the case if a tissue wall of a patient were above the puncture assembly 1200 with respect to FIG. 12A. In some examples, the angle is between zero and 90 degrees. In some examples, the angle is between 10 and 90 degrees.

As shown in FIGS. 12A-12B, the curve of the puncture element 1202 defines an abrupt pivot between the first axis 1208 and the second axis 1206. A proximal portion of the puncture element 1202 primarily defines a single longitudinal axis coincident with first axis 1208. A distal portion of the puncture element 1202 primarily defines a single longitudinal axis (which may be coincident with second axis 1206 in certain embodiments).

According to certain embodiments, the cross section of a distal portion of the puncture element 1202 may define a perimeter 1230 of a shape. In some examples, as shown in FIG. 12B, the shape may be substantially circular. In some embodiments, the first end of each of the plurality of blade edges 1204A-1204D is coincident with the tip 1210. In some embodiments, the second ends of the plurality of blade edges 1204A-1204D are coincident with a plurality of points on the perimeter 1230 of the shape. In some embodiments, the location of the tip 1210 projected onto the cross section is coincident with a point on the perimeter 1230 defined by the shape. In some embodiments, the location of the tip 1210 projected onto the cross section is located within the perimeter 1230 defined by the shape. In some embodiments, the location of the tip 1210 projected onto the cross section is located substantially in the center of the shape.

Figure 13:
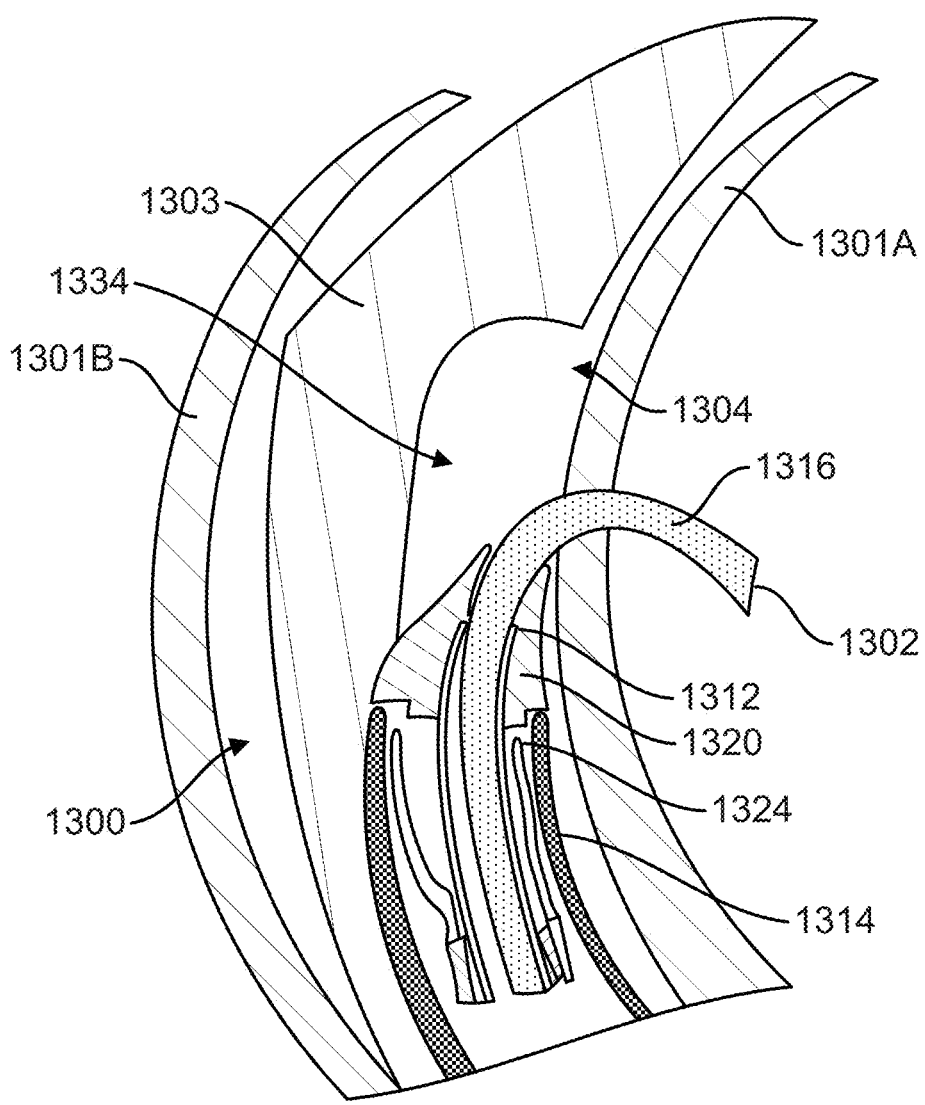
FIG. 13 is a schematic diagram of a cross-sectional view of an example of a shunting catheter within tissue walls of a patient, in accordance with embodiments of the present disclosure.

FIG. 13 is a schematic diagram of a cross-sectional view of an example of a shunting catheter 1300 within tissue walls 1301A-1301B of a patient, in accordance with embodiments of the present disclosure. The shunting catheter 1300 includes a catheter shaft 1303 having a shaft lumen 1334, and a puncture assembly. In some embodiments, the puncture assembly may include a puncture element 1302, a puncture shaft 1316, a dilator 1320, and an expandable element 1324 (e.g., a balloon, a basket). The expandable element 1324 may be deposited or positioned within a distal portion of an expandable element sheath 1314, and outside of an expandable element inner sheath 1312. In some embodiments, the expandable element 1324 may be connected to the outer surface of the expandable element inner sheath 1312.

The puncture assembly may be disposed within the shaft lumen 1334 of the shunting catheter 1300 at a first state (e.g., during deployment). At least part of the puncture assembly may be extended from the catheter shaft 1303 in another state (e.g., a puncturing state and/or an ablation state). According to certain embodiments, as shown, the expandable element inner sheath 1312 and the expandable element sheath 1314 may both define interior lumens. In certain embodiments, the puncture element 1302 and/or the puncture shaft 1316 may be disposed within one or more of the interior lumens defined by the expandable element inner sheath 1312 and the expandable element sheath 1314 at a first state (e.g., during deployment). The puncture element 1302 and the puncture shaft 1316 may be able to translate with respect to the expandable element sheath 1314 and the expandable element inner sheath 1312 independent of the movement of the expandable element sheath 1314 or the expandable element inner sheath 1312. In certain embodiments, the puncture element 1302 and a distal portion of the puncture shaft 1316 are extended from the expandable element inner sheath 1312, the expandable element sheath 1314, and the catheter shaft 1303 at a second state (e.g., a puncturing state) to puncture the tissue wall 1301A.

According to certain embodiments, one or more of the puncture element 1302 and/or the distal portion of the puncture shaft 1316 may be curved to facilitate directing a tip of the puncture element 1302 towards the tissue wall 1301A. The small diameter of the puncture shaft 1316 may allow the curve in the puncture shaft 1316 to bend the puncture shaft 1316 more towards the tissue wall 1301A than if the puncture shaft 1316 were not independently translatable with respect to the expandable element inner sheath 1312 and the expandable element sheath 1314. In certain embodiments, the puncture shaft 1316 has a predetermined curve. In some embodiments, the puncture shaft 1316 may have more flexibility to achieve a more curved shape during puncturing than, for example, the puncture assembly 501 since the puncture shaft 1316 is moving without restriction of an additional sheath (e.g., expandable element sheath 514 in FIG. 5) during the initial stage of puncturing. In certain embodiments, the expandable element sheath 1314 does not have a predetermined curve, but is made of an at least semi-malleable material that may allow a physician to manipulate the distal portion of the expandable element sheath 1314 into a curve. In some examples, portions of the puncture shaft 1316 may be formed of nitinol or stainless steel as a hypotube with a plurality of laser cuts to allow the puncture shaft 1316 to bend into a curved shape. In some examples, the plurality of laser cuts along the hypotube helps control the bending shape of the puncture shaft 1316.

According to some embodiments, when the catheter shaft 1303 is in a second state (e.g., a puncturing state) during puncturing of the tissue wall 1301A, the dilator 1320 connected to the distal end of the expandable element inner sheath 1312, the expandable element 1324 connected to an outer surface of the expandable element inner sheath 1312, as well as the expandable element sheath 1314 within which the expandable element 1324 is positioned in, may be translated together along the puncture shaft 1316 towards the distal end of the puncture shaft 1316 to enlarge an opening created by the puncture element 1302 through the punctured tissue wall 1301A. In some embodiments, after the expandable element 1324 is positioned at the target location, the expandable element sheath 1314 may be pulled back towards the proximal end of the catheter shaft 1303 separate from the dilator 1320 and the expandable element 1324, such that the expandable element 1324 is expanded to further enlarge an opening at the target location.

According to certain embodiments, the expandable element inner sheath 1312, which is connected to the dilator 1320 and the expandable element 1324, is extended from the catheter shaft 1303 at a third state (e.g., an ablation state). At the third state, the expandable element 1324 is configured to supply ablation energy to the tissue wall 1301A. In some embodiments, the expandable element inner sheath 1312 may be configured to translate along the puncture shaft 1316 of the puncture element 1302. The puncture shaft 1316 may act as a guide wire for the expandable element inner sheath 1312. In some embodiments, the expandable element 1324 and/or the dilator 1320 may be configured to deliver energy to tissue wall 1301A at the second and/or third state. In some embodiments, the dilator 1320 may be formed of a conductive material configured to transmit energy to tissue wall 1301A. In some embodiments, the dilator 1320 and/or the expandable element 1324 may include one or more electrodes configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall 1301A of a patient).

According to certain embodiments, the puncture shaft 1316 may further define an interior lumen and a pull wire assembly to control the flex or angle of the puncture shaft 1316 relative to the tissue wall 1301A. The pull wire assembly may be laser welded to the outside or inside of puncture shaft 1316. In some embodiments, the pull wire assembly may be connected to the puncture shaft 1316 at a distal end of the puncture shaft 1316. In some embodiments, the pull wire assembly may include nitinol, stainless steel (SS), cobalt, chromium, titanium, or a combination thereof.

In certain embodiments, during deployment, the guidewire may be used to guide the shunting catheter 1300 into the CS of a patient. In yet certain embodiments, the guidewire may be used to indicate the location of the shunting catheter 1300 including one or more of the components (e.g., the puncture assembly, the shaft opening 1304 of the catheter 1300, etc.) in the CS of a patient.

Figure 14:
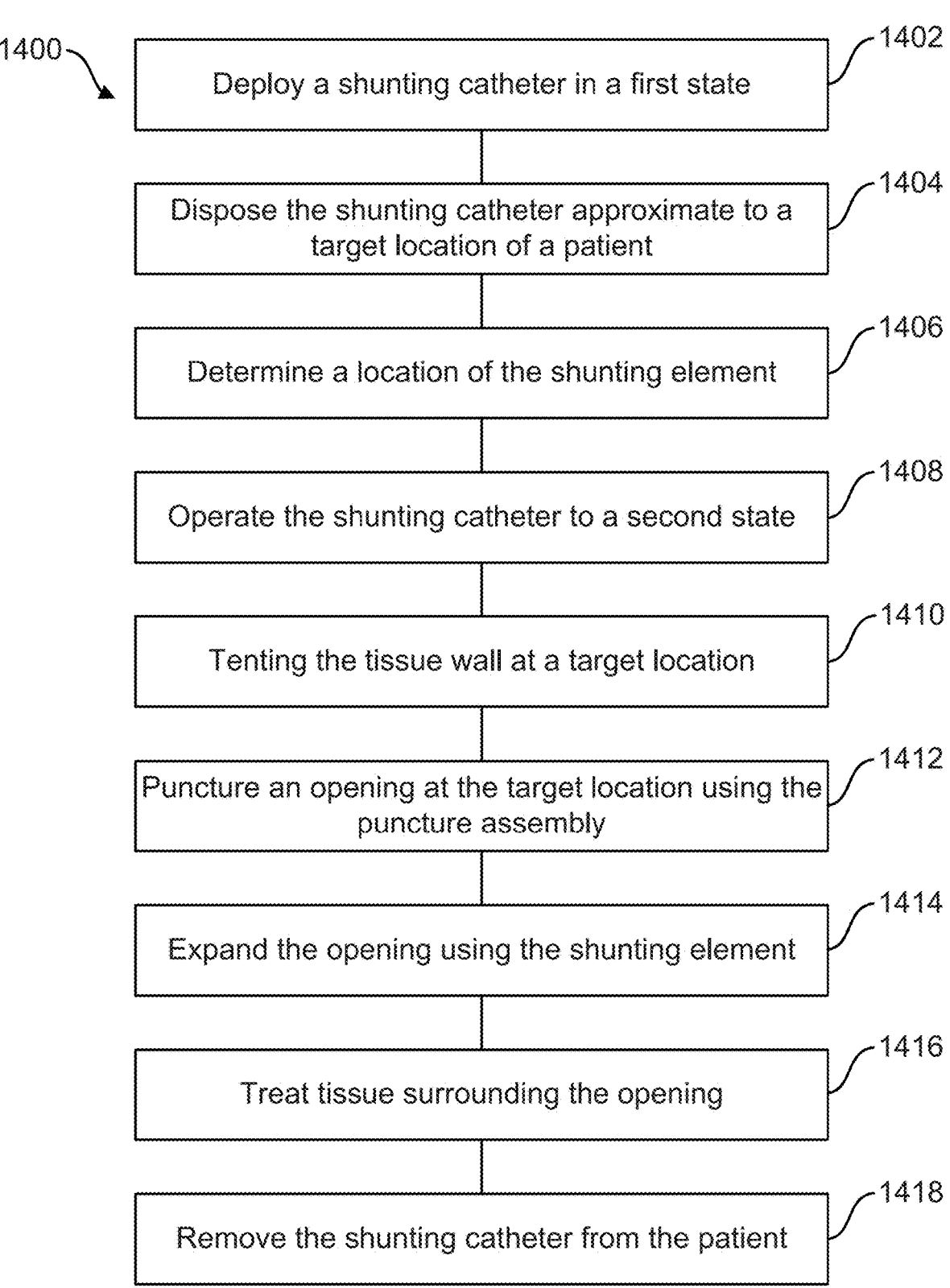
FIG. 14 is a flow diagram illustrating a process of creating a shunt in a patient, in accordance with embodiments of the present disclosure.

FIG. 14 is a flow diagram illustrating a process of creating a shunt in a patient, in accordance with embodiments of the present disclosure. The method is described in relation to the catheters discussed previously here, however, any suitable electroporation catheter can be used in the method. Aspects of embodiments of the method may be performed, for example, by a shunting catheter system or a controller (e.g., the system 104 in FIG. 1, the controller 112 in FIG. 1). One or more steps of method are optional and/or can be modified by one or more steps of other embodiments described herein. Additionally, one or more steps of other embodiments described herein may be added to the method. In some embodiments, the shunt may be formed in a coronary sinus of a patient. In certain embodiments, the shunt includes an opening between a patient's coronary sinus and left atrium.

At step 1402, the process 1400 includes deploying a shunting catheter in a first state, the shunting catheter including a catheter shaft having a distal end, a proximal end, a shaft lumen, and a puncture assembly. In some embodiments, the shunting catheter also includes a shunting component including one or more electrodes. The puncture assembly may include dilator having a proximal end and a distal end, and a puncture element disposed proximate to the distal end of the dilator. In some embodiments, the puncture assembly includes the shunting component. In some examples, the dilator is the shunting component and includes the one or more electrodes. In some embodiments, the puncture element is the shunting component and includes the one or more electrodes. In some embodiments, the puncture assembly is disposed in the shaft lumen at the first state. In certain embodiments, deploying the shunting catheter includes inserting the shunting catheter through a superior vena cava of a patient into a coronary sinus of the patient. In certain embodiments, deploying the shunting catheter includes inserting the shunting catheter through an inferior vena cava of a patient into a coronary sinus of the patient.

At step 1404, the process 1400 includes disposing the shunting catheter approximate to a target location of a patient. At step 1406, the process 1400 may include determining a location of the shunting element. In certain embodiments, location of the shunting element may be determined using an imaging device. In some embodiments, the imaging device includes one or more visualization elements disposed within or proximate the puncture assembly and/or the shunting element. In some embodiments, location of the shunting element may be determined using a sensor configured to detect the oxygen level within a vessel. In some embodiments, location of the shunting element may be determined by pulling blood from a patient's vessel to detect oxygen level, then comparing the detected oxygen level with anticipated oxygen level within a patient's vessel/heart chambers.

At step 1408, the process 1400 includes operating the shunting catheter to a second state, wherein the puncture assembly extends from the catheter shaft at an angle greater than zero degrees at the proximal end of the puncture assembly at the second state. In certain embodiments, the catheter shaft has a shaft opening, and the puncture assembly extends from the catheter shaft through the shaft opening. In some embodiments, the puncture assembly includes a curved puncture element wherein a tip of the curved puncture element defines a first axis and a body of the curved puncture element defines a second axis. In some examples, the first axis and the second axis form an angle greater than zero degrees.

At step 1410, in some embodiments, the process 1400 includes tenting the tissue wall to locate the puncture element and/or confirm a target location/direction of the tip for puncturing, using a blunted tip (e.g., tip 1010 of puncture element 1002, tip 1110 of puncture element 1102, tip 1710 of puncture element 1702, tip 1810 of puncture element 1802, tip 1910 of puncture element 1902). As used herein, tenting refers to pushing the tip of a puncture element against a tissue wall at or around the target location before ablative energy is applied to puncture through the tissue wall. Tenting before puncturing may help the physician or operator to locate the tip of the puncture element and ensure that the puncturing is at the intended location before applying ablative energy. In some embodiments, tenting may be used together with ultrasound techniques (e.g., by taking an echocardiogram of a patient's heart) to locate where the tip is contacting the tissue.

At step 1412, in some embodiments, the process 1400 includes puncturing, using the puncture element, an opening in patient tissue at the target location. In some embodiments, the target location is at a coronary sinus of a patient. In certain embodiments, the process 1400 includes delivering energy (e.g., radiofrequency (RF) energy, etc.) to the puncture element to create the opening.

At step 1414, the process 1400 includes expanding the opening using the dilator and/or the shunting element. In certain embodiments, the catheter shaft has a shaft opening, and the dilator and/or shunting element extend from the catheter shaft through the shaft opening. In some embodiments, the dilator is formed as a frustocone wherein a distal diameter of the frustocone is smaller than a proximal diameter of the frustocone.

At step 1416, the process 1400 may include treating tissue (e.g., by ablation) surrounding the opening using the puncture assembly and/or shunting element. In some embodiments, for example, the puncture element, the dilator, and/or the shunting element is configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to the tissue surrounding the opening. In some embodiments, the shunting element includes an expandable element (e.g., a balloon, a basket) that is expanded at a third state. In some embodiments, the dilator is formed as two frustocones that connect at a joint surface defining a largest diameter of the dilator.

At step 1418, the process 1400 may include removing the shunting catheter from a patient. In some embodiments, the process 1400 may include removing the shunting catheter, which includes removing the catheter shaft, the puncture assembly, and the shunting element. In certain embodiments, the process 1400 may include withdrawing one or more of the puncture assembly and the shunting element to the first state. In certain embodiments, the process 1400 does not leave any implant device at the target location. In some embodiments, a shunt is formed by creating an opening between a coronary sinus and a left atrium of a patient. In certain embodiments, the shunting catheter is removed from the coronary sinus of the patient. In certain embodiments, the formed shunt is an opening that does not include an implant (e.g., a frame or structure to support an opening). In some embodiments, the shunt consists of an opening between the coronary sinus and the left atrium of a patient; where the shunt does not include an implant.

According to some embodiments, the process 1400 includes generating a shunt using a shunting element of a shunting catheter. In certain embodiments, the shunt includes an expanded opening between the coronary sinus and left atrium of a patient. In some embodiments, the shunt does not include any implant.

FIG. 15 is a flow diagram illustrating a process of creating a shunt in a patient, in accordance with embodiments of the present disclosure. The method is described in relation to the catheters discussed previously here, however, any suitable electroporation catheter can be used in the method. Aspects of embodiments of the method may be performed, for example, by a shunting catheter system or a controller (e.g., the system 104 in FIG. 1, the controller 112 in FIG. 1). One or more steps of method are optional and/or can be modified by one or more steps of other embodiments described herein. Additionally, one or more steps of other embodiments described herein may be added to the method. In some embodiments, the shunt may be formed in a coronary sinus of a patient. In certain embodiments, the shunt includes an opening between a patient's coronary sinus and left atrium.

At step 1502, the process 1500 includes deploying a shunting catheter in a first state, the shunting catheter including a catheter shaft having a distal end, a proximal end, a shaft lumen, and a puncture assembly. In some embodiments, the shunting catheter also includes a shunting component including one or more electrodes. The puncture assembly may include dilator having a proximal end and a distal end, and a puncture element disposed proximate to the distal end of the dilator. In some embodiments, the puncture assembly includes the shunting component. In some examples, the dilator is the shunting component and includes the one or more electrodes. In some embodiments, the puncture element is the shunting component and includes the one or more electrodes. In some embodiments, the puncture assembly is disposed in the shaft lumen at the first state.

In certain embodiments, deploying the shunting catheter includes inserting the shunting catheter through a superior vena cava of a patient into a coronary sinus of the patient. In certain embodiments, deploying the shunting catheter includes inserting the shunting catheter through an inferior vena cava of a patient into a coronary sinus of the patient.

At step 1504, the process 1500 includes disposing the shunting catheter approximate to a target location of a patient. At step 1506, the process 1500 may include determining a location of the puncture assembly. In certain embodiments, location of the shunting element may be determined using an imaging device. In some embodiments, the imaging device includes one or more visualization elements disposed within or proximate the puncture assembly and/or the shunting element. In some embodiments, location of the shunting element may be determined using a sensor configured to detect the oxygen level within a vessel. In some embodiments, location of the shunting element may be determined by pulling blood from a patient's vessel to detect oxygen level, then comparing the detected oxygen level with anticipated oxygen level within a patient's vessel/heart chambers.

At step 1508, the process 1500 includes operating the shunting catheter to a second state, wherein the puncture assembly extends from the catheter shaft at an angle greater than zero degrees at the proximal end of the puncture assembly at the second state. In certain embodiments, the catheter shaft has a shaft opening, and the puncture assembly extends from the catheter shaft through the shaft opening. In some embodiments, the puncture assembly includes a curved puncture element wherein a tip of the curved puncture element defines a first axis and a body of the curved puncture element defines a second axis. In some examples, the first axis and the second axis form an angle greater than zero degrees.

At step 1510, in some embodiments, the process 1500 includes tenting the tissue wall to locate the puncture element and/or confirm a target location/direction of the tip for puncturing, using a blunted tip (e.g., tip 1010 of puncture element 1002, tip 1110 of puncture element 1102, tip 1710 of puncture element 1702, tip 1810 of puncture element 1802, tip 1910 of puncture element 1902). As used herein, tenting refers to pushing the tip of a puncture element against a tissue wall at or around the target location before ablative energy is applied to puncture through the tissue wall. Tenting before puncturing may help the physician or operator to locate the tip of the puncture element and ensure that the puncturing is at the intended location before applying ablative energy. In some embodiments, tenting may be used together with ultrasound techniques (e.g., by taking an echocardiogram of a patient's heart) to locate where the tip is contacting the tissue.

At step 1512, the process 1500 includes puncturing, using the puncture element, an opening in patient tissue at the target location. In some embodiments, the target location is at a coronary sinus of a patient.

At step 1514, the process 1500 includes operating the shunting catheter to a third state (e.g., a shunting state to use a shunting element). In certain embodiments, a shunting element shaft is extended from the shaft lumen at the third state, and the shunting element may be an expandable element (e.g., a balloon or a basket) configured to deliver ablative energy, and is expanded when the shunting element is at a third state. In some embodiments, the shunting element does not include an expandable element, and instead include one or more electrodes configured to deliver ablative energy to a patient's tissue, where the one or more electrodes are placed directly on a shunting element shaft.

In some embodiments, the shunting element translates along a puncture shaft to the opening punctured in patient tissue when transitioning form a second state to a third state. In certain embodiments, an expandable element inner sheath (e.g., expandable element inner sheath 1312), which is connected to a dilator (e.g., the dilator 1320) and a shunting element (e.g., the expandable element 1324), is extended from the catheter shaft at a third state (e.g., an ablation/shunting state).

At step 1516, the process 1500 includes expanding the opening using the dilator and/or the shunting element. In certain embodiments, the catheter shaft has a shaft opening, and the dilator and/or shunting element extend from the catheter shaft through the shaft opening. In some embodiments, the dilator is formed as a frustocone wherein a distal diameter of the frustocone is smaller than a proximal diameter of the frustocone.

At step 1518, the process 1500 may include treating tissue (e.g., by ablation) surrounding the opening using the puncture assembly and/or shunting element. In some embodiments, for example, the puncture element, the dilator, and/or the shunting element is configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to the tissue surrounding the opening. In some embodiments, the shunting element includes an expandable element (e.g., a balloon, a basket) that is expanded at a third state. In some embodiments, the dilator is formed as two frustocones that connect at a joint surface defining a largest diameter of the dilator.

At step 1520, the process 1500 may include removing the shunting catheter from a patient. In some embodiments, the process 1500 may include removing the shunting catheter, which includes removing the catheter shaft and the puncture assembly. In certain embodiments, the process 1500 may include withdrawing one or more of the puncture assembly and the shunting element to the first state. In certain embodiments, the process 1500 does not leave any implant device at the target location. In some embodiments, a shunt is formed by creating an opening between a coronary sinus and a left atrium of a patient. In certain embodiments, the shunting catheter is removed from the coronary sinus of the patient. In certain embodiments, the formed shunt is an opening that does not include an implant (e.g., a frame or structure to support an opening). In some embodiments, the shunt consists of an opening between the coronary sinus and the left atrium of a patient; where the shunt does not include an implant.

According to some embodiments, the process 1500 includes generating a shunt using a shunting element of a shunting catheter. In certain embodiments, the shunt includes an expanded opening between the coronary sinus and left atrium of a patient. In some embodiments, the shunt does not include any implant.

FIG. 16 is a flow diagram illustrating a process of creating a shunt in a patient, in accordance with embodiments of the present disclosure. The method is described in relation to the catheters discussed previously here, however, any suitable electroporation catheter can be used in the method. Aspects of embodiments of the method may be performed, for example, by a shunting catheter system or a controller (e.g., the system 104 in FIG. 1, the controller 112 in FIG. 1). One or more steps of method are optional and/or can be modified by one or more steps of other embodiments described herein. Additionally, one or more steps of other embodiments described herein may be added to the method. In some embodiments, the shunt may be formed in a coronary sinus of a patient. In certain embodiments, the shunt includes an opening between a patient's coronary sinus and left atrium.

At step 1602, the process 1600 includes deploying a shunting catheter in a first state, the shunting catheter including a catheter shaft having a distal end, a proximal end, a shaft lumen, and a puncture assembly. In some embodiments, the shunting catheter also includes a shunting component including one or more electrodes. The puncture assembly may include dilator having a proximal end and a distal end, and a puncture element disposed proximate to the distal end of the dilator. In some embodiments, the puncture assembly includes the shunting component. In some examples, the dilator is the shunting component and includes the one or more electrodes. In some embodiments, the puncture element is the shunting component and includes the one or more electrodes. In some embodiments, the puncture assembly is disposed in the shaft lumen at the first state.

In certain embodiments, deploying the shunting catheter includes inserting the shunting catheter through a superior vena cava of a patient into a coronary sinus of the patient. In certain embodiments, deploying the shunting catheter includes inserting the shunting catheter through an inferior vena cava of a patient into a coronary sinus of the patient.

At step 1604, the process 1600 includes disposing the shunting catheter approximate to a target location of a patient. At step 1606, the process 1600 may include determining a location of the puncture assembly. In certain embodiments, location of the shunting element may be determined using an imaging device. In some embodiments, the imaging device includes one or more visualization elements disposed within or proximate the puncture assembly and/or the shunting element. In some embodiments, location of the shunting element may be determined using a sensor configured to detect the oxygen level within a vessel. In some embodiments, location of the shunting element may be determined by pulling blood from a patient's vessel to detect oxygen level, then comparing the detected oxygen level with anticipated oxygen level within a patient's vessel/heart chambers.

At step 1608, the process 1600 includes operating the shunting catheter to a second state, wherein the puncture assembly extends from the catheter shaft at an angle greater than zero degrees at the proximal end of the puncture assembly at the second state. In certain embodiments, the catheter shaft has a shaft opening, and the puncture assembly extends from the catheter shaft through the shaft opening. In some embodiments, the puncture assembly includes a curved puncture element wherein a tip of the curved puncture element defines a first axis and a body of the curved puncture element defines a second axis. In some examples, the first axis and the second axis form an angle greater than zero degrees.

At step 1610, in some embodiments, the process 1600 includes tenting the tissue wall to locate the puncture element and/or confirm a target location/direction of the tip for puncturing, using a blunted tip (e.g., tip 1010 of puncture element 1002, tip 1110 of puncture element 1102, tip 1710 of puncture element 1702, tip 1810 of puncture element 1802, tip 1910 of puncture element 1902). As used herein, tenting refers to pushing the tip of a puncture element against a tissue wall at or around the target location before ablative energy is applied to puncture through the tissue wall. Tenting before puncturing may help the physician or operator to locate the tip of the puncture element and ensure that the puncturing is at the intended location before applying ablative energy. In some embodiments, tenting may be used together with ultrasound techniques (e.g., by taking an echocardiogram of a patient's heart) to locate where the tip is contacting the tissue.

At step 1612, the process 1600 includes delivering energy to the puncture element. In some embodiments, the process 1600 includes delivering energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to the puncture element to facilitate puncturing through a patient's tissue wall.

At step 1614, the process 1600 includes puncturing, using the puncture element, an opening in patient tissue at the target location. In some embodiments, the target location is at a coronary sinus of a patient.

At step 1616, the process 1600 includes operating the shunting catheter to a third state (e.g., a shunting state to use a shunting element). In certain embodiments, a shunting element shaft is extended from the shaft lumen at the third state, and the shunting element may be an expandable element (e.g., a balloon or a basket) configured to deliver ablative energy, and is expanded when the shunting element is at a third state. In some embodiments, the shunting element does not include an expandable element, and instead include one or more electrodes configured to deliver ablative energy to a patient's tissue, where the one or more electrodes are placed directly on a shunting element shaft.

In some embodiments, the shunting element translates along a puncture shaft to the opening punctured in patient tissue when transitioning form a second state to a third state. In certain embodiments, an expandable element inner sheath (e.g., expandable element inner sheath 1312), which is connected to a dilator (e.g., the dilator 1320) and a shunting element (e.g., the expandable element 1324), is extended from the catheter shaft at a third state (e.g., an ablation/shunting state).

At step 1618, the process 1600 includes expanding the opening using the dilator and/or the shunting element. In certain embodiments, the catheter shaft has a shaft opening, and the dilator and/or shunting element extend from the catheter shaft through the shaft opening. In some embodiments, the dilator is formed as a frustocone wherein a distal diameter of the frustocone is smaller than a proximal diameter of the frustocone.

At step 1620, the process 1600 may include treating tissue (e.g., by ablation) surrounding the opening using the puncture assembly and/or shunting element. In some embodiments, for example, the puncture element, the dilator, and/or the shunting element is configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to the tissue surrounding the opening. In some embodiments, the shunting element includes an expandable element (e.g., a balloon, a basket) that is expanded at a third state. In some embodiments, the dilator is formed as two frustocones that connect at a joint surface defining a largest diameter of the dilator.

At step 1622, the process 1600 may include removing the shunting catheter from a patient. In some embodiments, the process 1600 may include removing the shunting catheter, which includes removing the catheter shaft and the puncture assembly. In certain embodiments, the process 1600 may include withdrawing one or more of the puncture assembly and the shunting element to the first state. In certain embodiments, the process 1600 does not leave any implant device at the target location. In some embodiments, a shunt is formed by creating an opening between a coronary sinus and a left atrium of a patient. In certain embodiments, the shunting catheter is removed from the coronary sinus of the patient. In certain embodiments, the formed shunt is an opening that does not include an implant (e.g., a frame or structure to support an opening). In some embodiments, the shunt consists of an opening between the coronary sinus and the left atrium of a patient; where the shunt does not include an implant.

According to some embodiments, the process 1600 includes generating a shunt using a shunting element of a shunting catheter. In certain embodiments, the shunt includes an expanded opening between the coronary sinus and left atrium of a patient. In some embodiments, the shunt does not include any implant.

Figure 17:
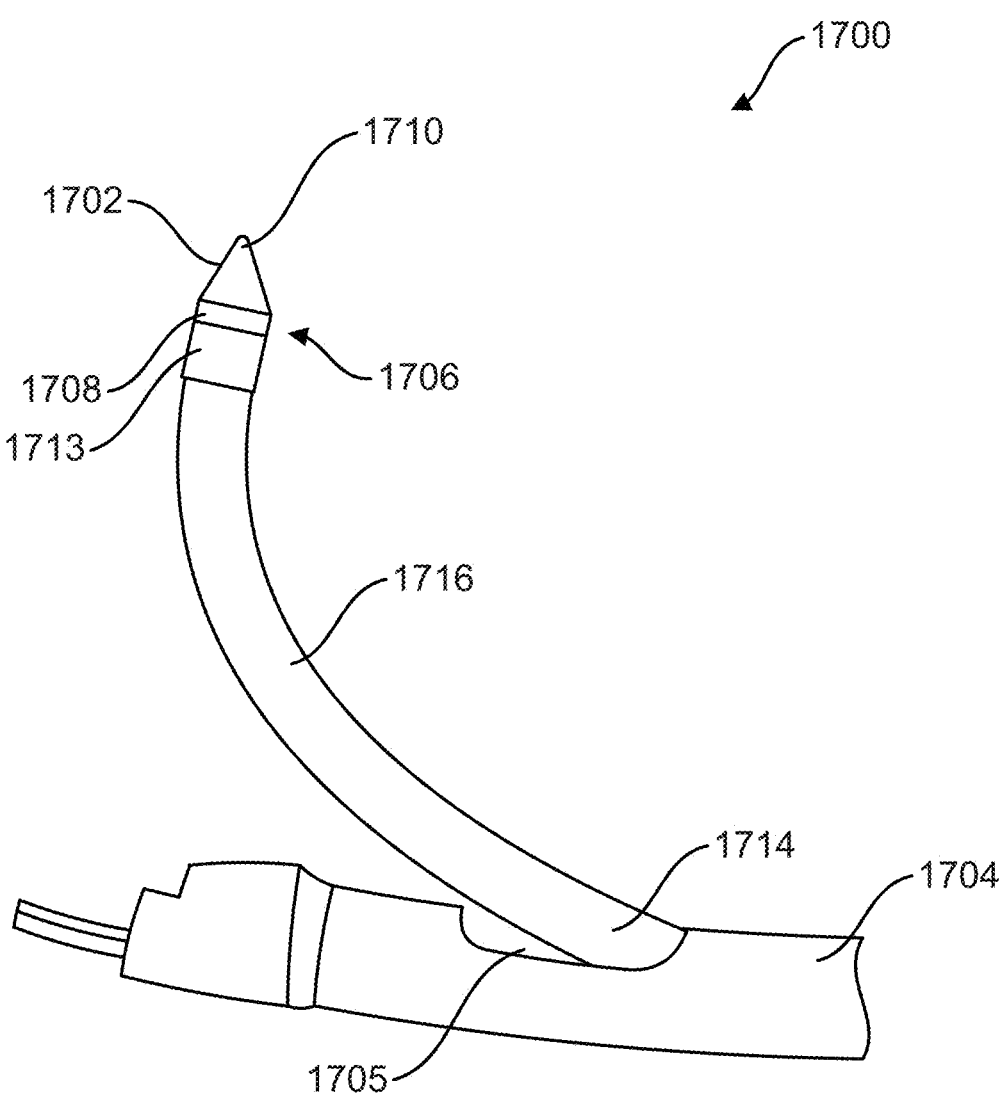
FIG. 17 is a schematic diagram of an example shunting device, in accordance with embodiments of the present disclosure.

FIG. 17 is a schematic diagram of an example shunting device 1700, in accordance with embodiments of the present disclosure. FIG. 17 is merely an example. One of the ordinary skilled in the art would recognize many variations, alternatives, and modifications. As shown, in some embodiments, the shunting device 1700 includes a shunting catheter 1704 to be delivered through a patient's coronary sinus (CS), a shunting element 1706, and a puncture element 1702.

According to certain embodiments, the shunting catheter 1704 includes a catheter shaft, and a shaft lumen. According to certain embodiments, the shunting element 1706 is disposed in the shaft lumen at a first state. In some embodiments, the shunting element 1706 includes an expandable element 1708 disposed within a shunting element shaft 1714. In certain embodiments, the expandable element 1708 may be positioned within an expandable element sheath 1713, and collectively within the catheter shaft of shunting catheter 1704, at a first state. In some embodiments, the expandable element 1708 is crimped when positioned within the expandable element sheath 1713 at a first state. In certain embodiments, the expandable element 1708 is an elongated element. The shunting element 1706 may be connected to the shunting element shaft 1714 positioned within the shaft lumen of the catheter 1704 at a first state. In certain embodiments, the shunting element shaft 1714 has a pre-determined curve 1716. In some examples, the shunting element shaft 1714 has a pre-determined curve 1716 for the shunting element 1706 to deploy. In certain embodiments, the shunting element shaft 1714 is extended from the shaft lumen of the catheter shaft at a second state (e.g., a puncturing state to puncture through a tissue wall of a patient) and/or a third state (e.g., a shunting state to use the shunting element). In some examples, the expandable element 1708 may be a balloon or a basket configured to deliver ablative energy, and is expanded when the shunting element 1706 is at a third state.

According to certain embodiments, the puncture element 1702 is disposed in the shaft lumen of catheter 1704 at a first state. The puncture element 1702 may be connected to the shunting element 1706 positioned within the shaft lumen of the catheter 1704 at a first state (e.g., before a deployment and/or during a deployment to position the shunting element 1706).

In some embodiments, the puncture element 1702 (e.g., along with the shunting element 1706) is extended from the catheter shaft of catheter 1704 through opening 1705 at a second state (e.g., a puncturing state to puncture through a tissue wall). According to some embodiments, the puncture element 1702 has a tip defining a distal point of the puncture element. In some embodiments, as shown, the puncture element 1702 may define a conical shape with a tip of the cone at a distal most point of the puncture element 1702. In some examples, the conical shape of the puncture element 1702 is primarily straight (as opposed to the curved cone shown in FIGS. 10 and 18). In some examples, the pre-determined curve 1716 of the shunting element shaft 1714 may assist the puncture element 1702 in puncturing through a tissue wall of a patient by angling the puncture element 1702 towards a tissue wall of the patient as the puncture element 1702 extends out of catheter 1704 to the second state.

In certain embodiments, the puncture element 1702 includes a blunted tip 1710. In certain examples, the distal tip 1710 is a blunted tip defining a radius of from about one to about thirty thousandths of an inch, from about five to about thirty thousandths of an inch, or from about ten to about thirty thousandths of an inch, or from about fifteen to about thirty thousandths of an inch. In certain examples, the distal tip 1710 is a blunted tip defining a radius of from about 0.0254 to about 0.762 millimeters, or from about 0.254 to about 0.762 millimeters, or from about 0.381 to about 0.762 millimeters. In some examples, the distal tip 1710 defines a radius of from about 0.127 to about 0.254 millimeters. In some embodiments, the distal tip 1710 is a blunted tip configured to tent (e.g. push against without puncturing through) a tissue wall at a target location to locate the puncture element and/or confirm a location of the distal tip and/or a direction the distal tip is contacting the tissue wall before puncturing. Tenting before puncturing may help the physician or operator to locate the tip 1710 of the puncture element 1702 and ensure that the puncturing is at the intended location before applying ablative energy. In some embodiments, tenting may be used together with ultrasound techniques (e.g., by taking an echocardiogram of a patient's heart) to locate where the tip is contacting the tissue.

In some embodiments, the puncture element 1702 may be configured to deliver energy, or include one or more electrodes configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall of a patient). As shown, in some embodiments, the puncture element 1702 may be formed of a conductive material to deliver the energy to target tissue. In some embodiments, in order to puncture through patient tissue, the puncture element 1702 may be pressed into patient tissue at a target site to tent the patient tissue. If the puncture element 1702 is determined to be positioned correctly, ablative energy may be transmitted through the puncture element 1702 to the patient tissue at the target site to puncture through the tissue.

Figure 18:
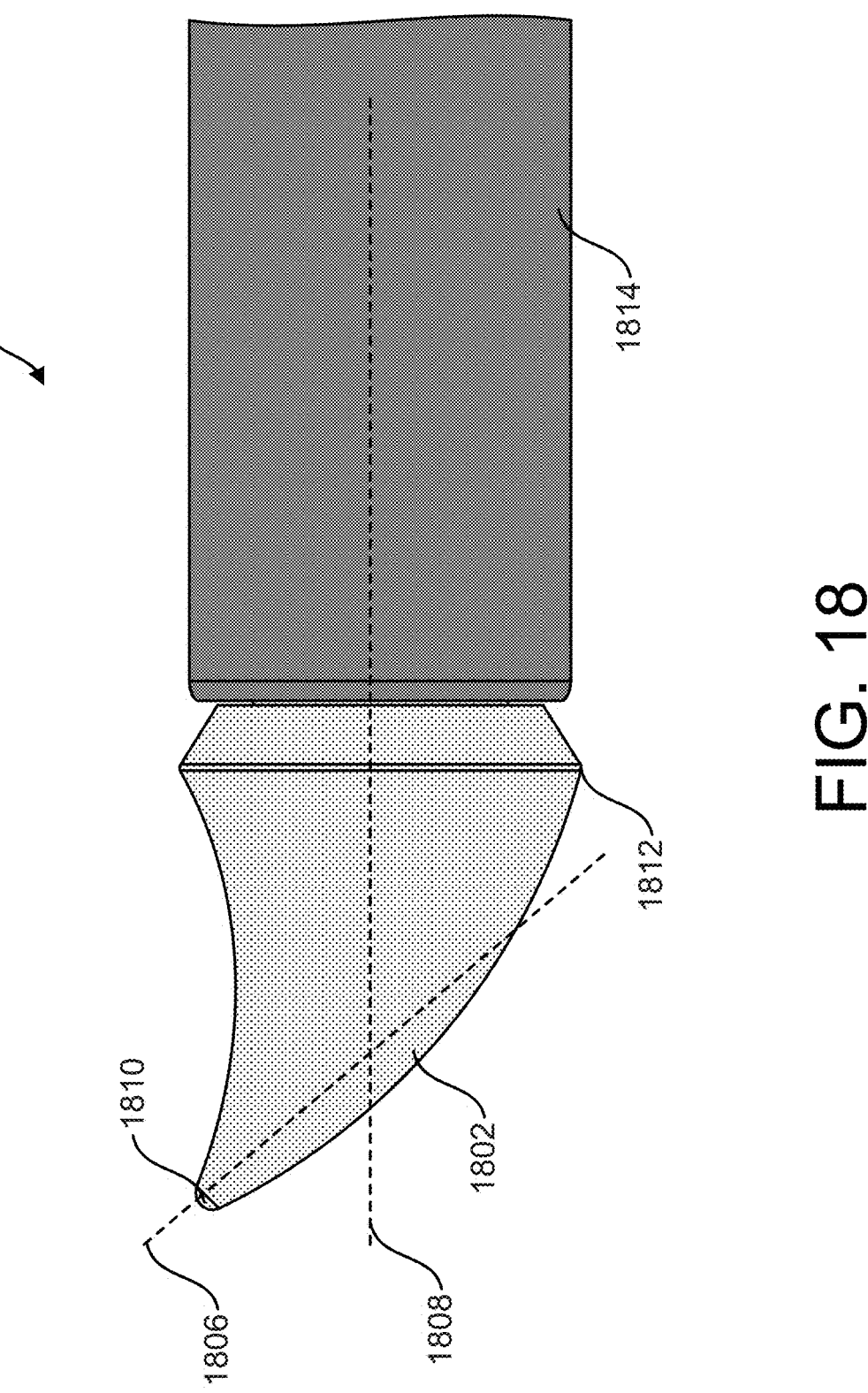
FIG. 18 is a schematic diagram of a side view of an example of a puncture assembly having a curved, conical puncture element integrated with the dilator, in accordance with embodiments of the present disclosure.

FIG. 18 is a schematic diagram of a side view of an example of a puncture assembly 1800 having a curved, conical puncture element 1802 integrated with the dilator, in accordance with embodiments of the present disclosure. As shown, the puncture assembly 1800 includes a puncture element 1802, a dilator 1812 integrated with the puncture element 1802, and a distal portion of an expandable element sheath 1814.

The puncture assembly 1800 may define a first axis 1808. In some embodiments, the first axis 1808 may be coincident with a longitudinal axis defined by one or more of the puncture assembly 1800, and/or the distal portion of the expandable element sheath 1814. In some embodiments, the first axis 1808 may be defined by a proximal portion of the puncture element 1802. In some embodiments, the first axis 1808 may be defined by a longitudinal axis of a proximal portion of the puncture element 1802. According to certain embodiments, the body of the puncture element 1802 may define the second axis 1806. In some embodiments, the second axis 1806 may be defined by the tip 1810 of the puncture element 1802. As shown in FIG. 18, the second axis 1806 passes through the tip 1810 and defines a longitudinal axis of the puncture element 1802 at the tip 1810.

As shown, the puncture element 1802 integrated with the dilator 1812 defines a conical shape, wherein the distal tip 1810 of the puncture element 1802 is a tip of the conical shape. In some embodiments, the distal tip 1810 is a blunted tip. In some examples, the distal tip 1810 has a rounded shape that defines a radius of from about one to about thirty thousandths of an inch. In certain examples, the distal tip 1810 is a blunted tip defining a radius of from about five to about thirty thousandths of an inch, or from about ten to about thirty thousandths of an inch, or from about fifteen to about thirty thousandths of an inch. In some examples, the distal tip 1810 defines a radius of five to ten thousandths of an inch. In certain examples, the distal tip 1810 is a blunted tip defining a radius of from about 0.0254 to about 0.762 millimeters, or from about 0.254 to about 0.762 millimeters, or from about 0.381 to about 0.762 millimeters. In some examples, the distal tip 1810 defines a radius of from about 0.127 to about 0.254 millimeters. The integration of both the puncture element 1802 and the dilator 1812 into a single form may provide a smoother transition from the distal tip 1810 to the expandable element sheath 1814. In addition, the integration reduces the number of components necessary for the puncture assembly.

According to certain embodiments, as shown, the puncture element 1802 may be curved. The curve may bias the tip 1810 towards a tissue wall of a patient when the puncture element 1802 is in use. In some embodiments, an angle between the first axis 1808 and the second axis 1806 biases the tip 1810 towards a tissue wall of a patient when the puncture element 1802 is in use. This may be the case if a tissue wall of a patient were above the puncture assembly 1800 with respect to FIG. 10. In some examples, the angle is between zero and 90 degrees. In some examples, the angle is between 10 and 90 degrees.

In some embodiments, the integrated puncture element 1802 and dilator 1812 may be configured to deliver energy, or include one or more electrodes configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall of a patient). In some embodiments, the integrated puncture element 1802 and dilator 1812 may be formed of a conductive material to deliver the energy to target tissue. In some embodiments, in order to puncture through patient tissue, the puncture element 1802 may be pressed into patient tissue at a target site to tent the patient tissue. If the puncture element 1802 is determined to be positioned correctly, ablative energy may be transmitted through the integrated puncture element 1802 and dilator 1812 to the patient tissue at the target site to puncture through the tissue.

As shown in FIG. 18, the curve of the puncture element 1802 defines a smooth transition between the first axis 1808 and the second axis 1806. In some embodiments, the longitudinal axis defined by the puncture element 1802 along a length of the puncture element 1802 may gradually shift from the first axis 1808 to the second axis 1806 through the angle between the first axis 1808 and the second axis 1806.

Figure 19A:
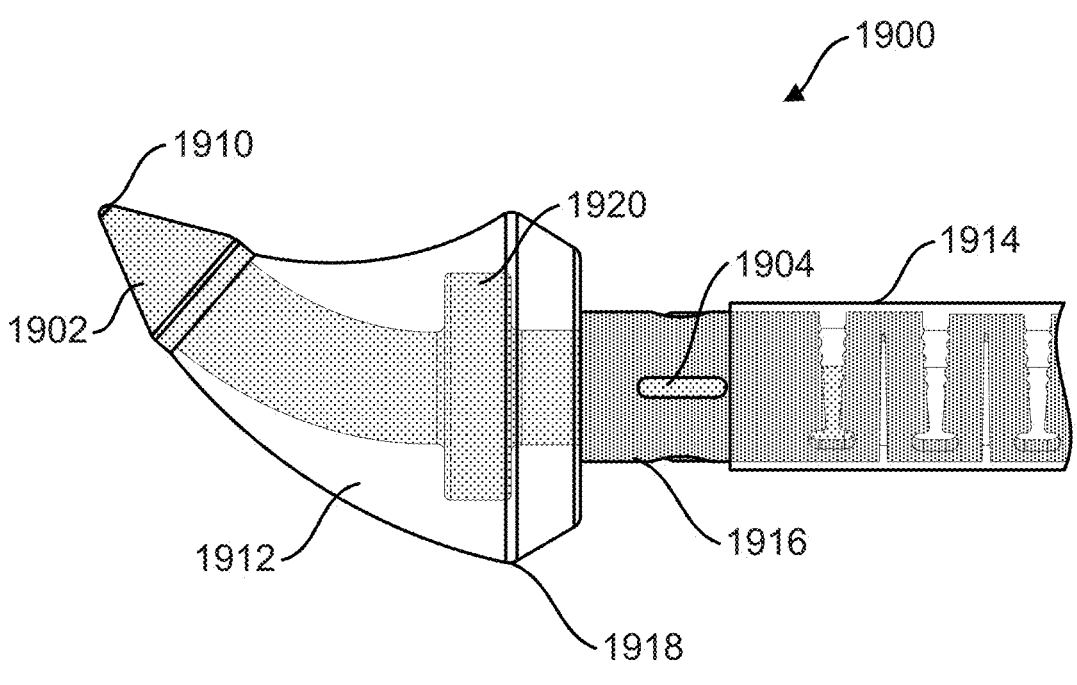
FIGS. 19A-19B are schematic diagrams of an example puncture assembly with a dilator overmolded onto a puncture element, in accordance with embodiments of the present disclosure.
Figure 19B:
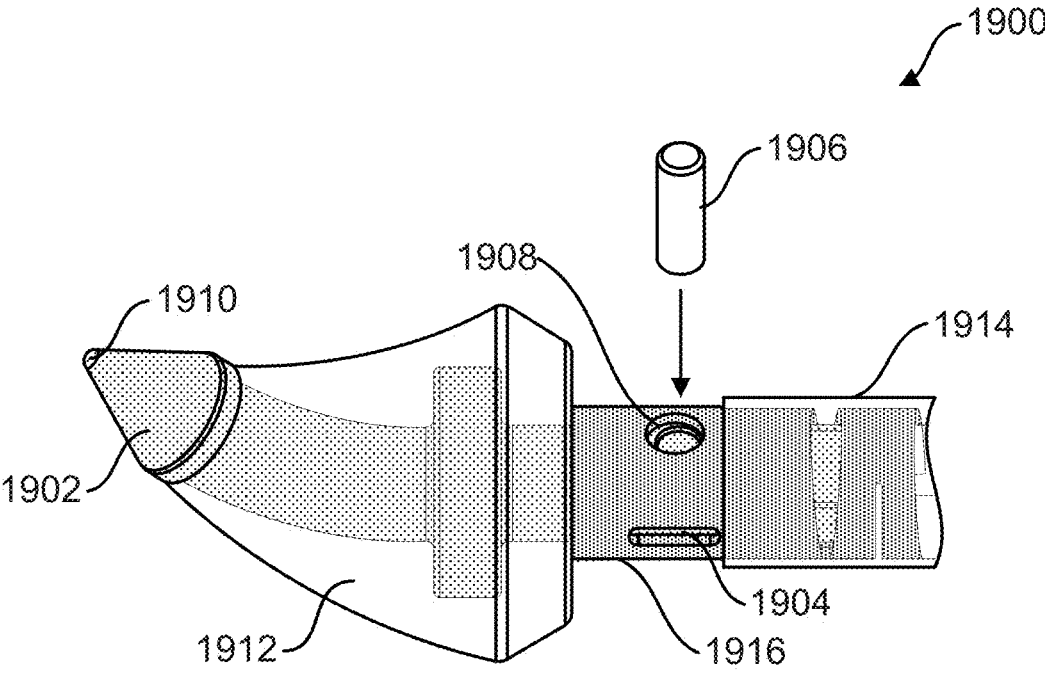

FIGS. 19A-19B are schematic diagrams of an example puncture assembly 1900 having a curved puncture element 1902 overmolded with a dilator 1912, in accordance with embodiments of the present disclosure. As shown, the puncture assembly 1900 includes a puncture element 1902, a dilator 1912 overmolding the puncture element 1902, and a distal portion of an expandable element inner sheath 1914. In certain embodiments, the puncture element may be integrated with the dilator and formed as one piece (e.g., the puncture element 1802 with dilator 1812). In yet certain embodiments, for example as shown in FIGS. 19A-19B, the dilator 1912 may be integrated with the puncture element 1902 as separate pieces, and overmolded onto the puncture element 1902. As shown in FIGS. 19A and 19B, dilator 1912 is shown as semi-transparent in order to better visualize an interior portion of puncture element 1902.

In some embodiments, the puncture assembly 1900 may further include an expandable element (e.g., shunting element 206, expandable element 412, etc.). The expandable element may be disposed outside of the expandable element inner sheath 1914, and further within an expandable element sheath (e.g., expandable element sheath 514, expandable element sheath 614, etc.). In some examples, the expandable element may be a balloon or a basket configured to deliver ablative energy, and is expanded when the expandable element is at a second state (e.g., a puncturing state to puncture a tissue wall).

The puncture assembly 1900 may also include a distal portion of a hypotube 1916. Expandable element inner sheath 1914 may include one or more interior lumens, in which hypotube 1916 is disposed. As shown in FIGS. 19A and 19B, expandable element inner sheath 1914 is shown as semi-transparent in order to better visualize hypotube 1916. In certain embodiments, the hypotube 1916 may be formed of a conductive material configured to transmit ablation energy to the puncture element 1902. In certain examples, the hypotube 1916 may be formed of a conductive material configured to transmit ablation energy from a proximal end of the shunting catheter to the puncture element 1902. In certain examples, the hypotube 1916 extends within the shunting catheter from a proximal end of the shunting catheter to the puncture element 1902. In certain embodiments, the expandable element inner sheath 1914 may be configured to insulate the hypotube 1916. In certain examples, the expandable element inner sheath 1914 may be formed of a non-conductive material to insulate the hypotube 1916.

The hypotube 1916 may include a plurality of laser cuts generally perpendicular to a longitudinal axis defined by the hypotube 1916. In some embodiments, at least some of the plurality of laser cuts may be non-perpendicular to the longitudinal axis defined by the hypotube 1916. In certain embodiments, the hypotube 1916 includes a distal portion devoid of laser cuts. In certain examples, a distal end of the hypotube 1916 may abut a proximal end of the dilator 1912. In certain embodiments, a proximal portion of the puncture element 1902 may be disposed within an interior lumen defined by the hypotube 1916. The proximal portion of the puncture element 1902 may be configured to fit within the lumen through an opening on a distal end of the hypotube 1916. In some embodiments, the puncture element 1902 may be affixed to the hypotube 1916 by press-fitting the proximal portion of the puncture element 1902 into the interior lumen defined by the hypotube 1916. In some embodiments, the puncture element 1902 may be affixed to the hypotube 1916 by welding the puncture element 1902 to the hypotube 1916, for example, using a weld port 1904. In some instances, the puncture element 1902 may be affixed to the hypotube 1916 using a pin 1906. The pin 1906 may be pressed through a pinhole 1908 in the hypotube 1916 into an interior of the puncture element 1902 to lock the hypotube 1916 together with the puncture element 1902. In some embodiments, any one or more of a press-fit, the pin 1906, and welding may be used to affix the puncture element 1902 to the hypotube 1916.

In some embodiments, the distal portion of the hypotube 1916 may include a lumen port for pulling blood from a patient's vessel. In some instances, the lumen port may be the pinhole 1908, and the puncture element 1902 is affixed to the hypotube using a method other than the pin 1906. In certain instances, the lumen port may be an opening in addition to the pinhole 1908 (not shown). In certain embodiments, location of the puncture element 1902 may be determined by pulling blood from a patient's vessel to detect oxygen level and/or pressure, then comparing the detected oxygen level and/or pressure with anticipated values for certain locations within a patient's vessel/heart chambers. In certain embodiments, the lumen port may be used for pulling blood from a patient's vessel, then the pulled blood may be used for confirming that the puncture element 1902 is located within a patient's left heart chamber. In some embodiments, the lumen port may be used for shooting contrast dye into the catheter shaft, and using contrast imaging to determine location of the puncture element 1902 and/or the dilator 1912 within a patient's vessel/heart chambers. In some embodiments, the lumen port may be used for flushing the system during the procedure.

According to some embodiments, as shown, puncture element 1902 includes a tip 1910 defining a distal point of the puncture element 1902. The tip 1910 may define a smallest diameter of puncture assembly 1900, where the diameter of the puncture assembly 1900 increases in a direction proximal of the tip 1910 along the length of the puncture element 1902 and/or dilator 1912. In some embodiments, the dilator 1912 may define a maximum diameter 1918 along the length of the dilator 1912 between a distal end and a proximal end of the dilator 1912. In some embodiments, the maximum diameter 1918 of the dilator 1912 may define a distal portion of the dilator 1912 distal of the maximum diameter 1918 and a proximal portion of the dilator 1912 proximal of the maximum diameter 1918. The distal portion and the proximal portion of the dilator 1912 may both define frustocones. An exterior surface of the dilator 1912 may be smooth. The dual frustoconical shapes of the dilator 1912 may allow the dilator 1912 to smoothly dilate a puncture hole through a patient's tissue wall as the dilator 1912 is extended distally through the puncture hole or withdrawn proximally through the puncture hole. The distal end of the dilator 1912 may define a diameter roughly equal to a diameter defined by the puncture element 1902 at the same point along the length of the puncture element 1902 that creates a smooth transition between the dilator 1912 and an exposed portion of the puncture element 1902.

In some embodiments, the puncture element 1902 may be configured to deliver energy, or include one or more electrodes configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall of a patient). In certain embodiments, the puncture element 1902 is formed of a conductive material configured to transmit ablation energy to tissue of a patient. In some embodiments, the puncture element 1902 may include a conductive material (e.g., a metal), for example, nitinol, stainless steel (SS), cobalt, chromium, titanium, or a combination thereof.

According to certain embodiments, the dilator 1912 is formed as a separate part of the puncture element 1902. In some embodiments, the dilator 1912 is overmolded on top of a proximal portion of the puncture element 1902. In certain examples, the dilator 1912 is formed of a non-conductive material configured to insulate the puncture element 1902. The dilator 1912 being formed of a non-conductive material may offer benefits of a smooth puncturing/dilating process while at the same time allow for more efficient energy delivery to the tip 1910, since a smaller portion of the puncture element 1902 is formed of a conductive material. In some embodiments, the dilator 1912 may include a polymer material, for example, machine Acrylonitrile Butadiene Styrene (ABS), Polyoxymethylene (POM) (e.g., Delrin®), Poly(ether-b-amide) copolymers (e.g., PEBAX®), Polyamide (e.g., nylon), Polytetrafluoroethylene (PTFE), lubricious PTFE (e.g., Teflon™), Polyether ether ketone (PEEK), or a combination thereof. In certain embodiments, the dilator 1912 is injected molded out of the same of similar materials as the puncture element 1902. In certain embodiments, the dilator 1912 is injected molded out of polymer material, ABS, POM, Poly(ether-b-amide) copolymers (e.g., PEBAX®), Polyamide, lubricious PTFE, PEEK or a combination thereof. In some embodiments, the dilator 1912 may include an insulative material suitable for overmolding, for example, silicone, Poly(ether-b-amide) copolymers (e.g., PEBAX®), nylon, polycarbonate, PTFE (e.g., Teflon™), polyethylene, PEEK, or a combination thereof, or any other insulative material suitable for overmolding.

As shown, the puncture element 1902 overmolded with the dilator 1912 defines a conical shape, wherein the distal tip 1910 of the puncture element 1902 is a tip of the conical shape. In certain examples, the distal tip 1910 is a blunted tip defining a radius of from about one to about thirty thousandths of an inch, or from about ten to about thirty thousandths of an inch, or from about fifteen to about thirty thousandths of an inch. In some examples, the distal tip 1910 defines a radius of five to ten thousandths of an inch. In certain examples, the distal tip 1910 is a blunted tip defining a radius of from about 0.0254 to about 0.762 millimeters, or from about 0.254 to about 0.762 millimeters, or from about 0.381 to about 0.762 millimeters. In some examples, the distal tip 1910 defines a radius of from about 0.127 to about 0.254 millimeters. The puncture element 1902 overmolded with the dilator 1912 may provide a smoother transition from the distal tip 1910 to the expandable element inner sheath 1914. Although a space is shown between a proximal end of the dilator 1912 and a distal end of the expandable element inner sheath 1914 in FIGS. 19A-19B, in some embodiments, for example during delivery of the puncture assembly 1900 to a target location, the distal end of the expandable element inner sheath 1914 abuts the proximal end of the dilator 1912. According to certain embodiments, as shown, the puncture element 1902 as well as the dilator 1912 overmolding the puncture element 1902 may be curved. The curve may bias the tip 1910 towards a tissue wall of a patient when the puncture element 1902 is in use.

In some embodiments, the distal tip 1910 is a blunted tip configured to tent (e.g. push against without puncturing through) a tissue wall at a target location to locate the puncture element and/or confirm a location of the distal tip and/or a direction the distal tip is contacting the tissue wall before puncturing. Tenting before puncturing may help the physician or operator to locate the tip 1910 of the puncture element 1902 and ensure that the puncturing is at the intended location before applying ablative energy. In some embodiments, tenting may be used together with ultrasound techniques (e.g., by taking an echocardiogram of a patient's heart) to locate where the tip is contacting the tissue.

As shown in FIGS. 19A-19B, the puncture element 1902 is overmolded with the dilator 1912. To form the puncture element 1902 and the dilator 1912 overmolding the puncture element 1902, the puncture element 1902 may first be machined out of a conductive material to transmit ablation energy to tissue of a patient, as described above, then placed in a mold. The dilator 1912 may be overmolded around the puncture element 1902 as shown. As described above, the dilator 1912 may be formed of a non-conductive material configured to insulate the puncture element 1902, as well as a material capable of being molded over puncture element 1902. In some embodiments, for example as shown in FIGS. 19A-19B, the puncture element 1902 may include one or more anchoring elements 1920 configured to anchor the dilator 1912 with respect to the puncture element 1902 when the dilator 1912 is overmolded on the puncture element 1902.

Figure 20A:
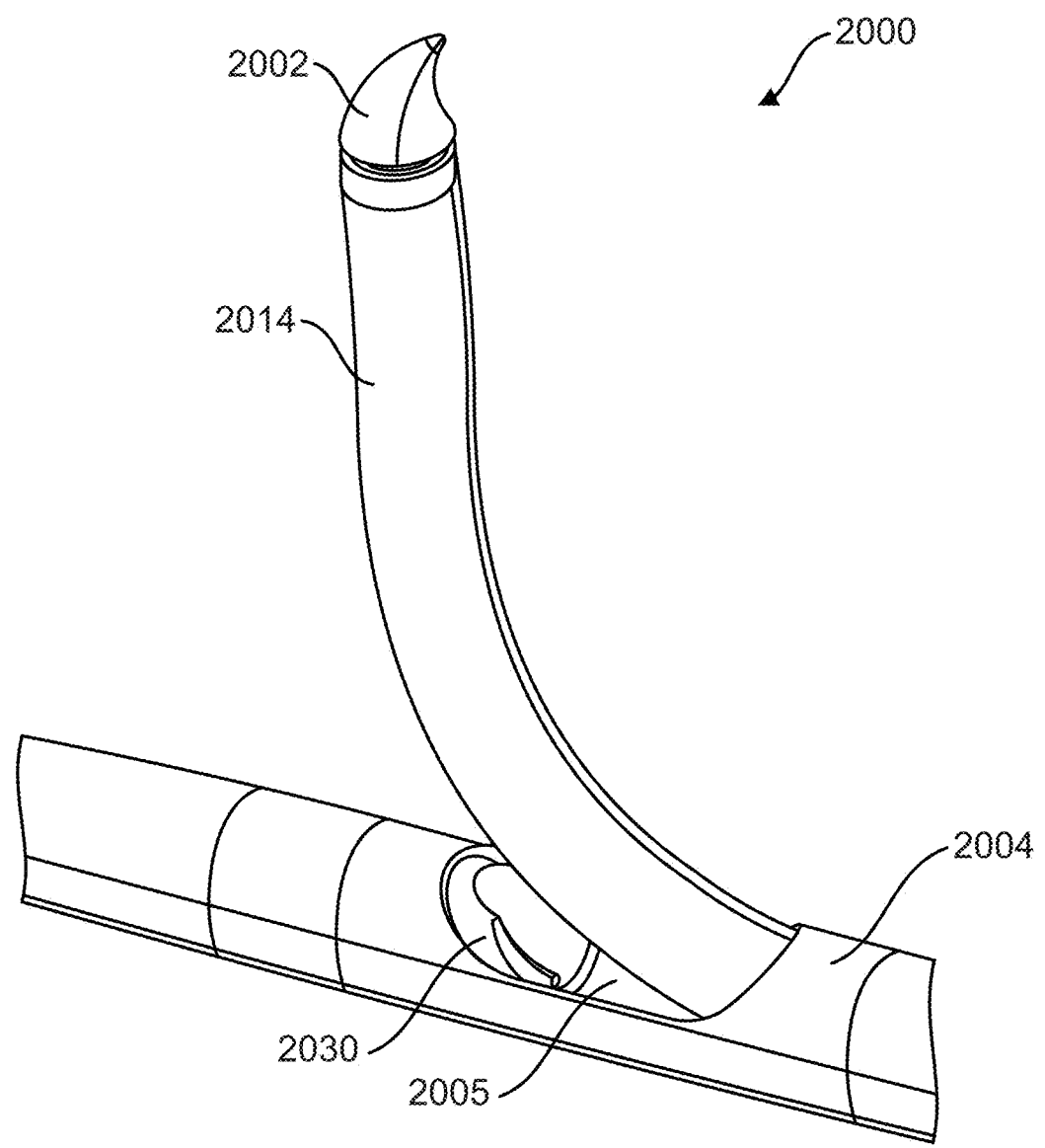
FIGS. 20A-20C are schematic diagrams of an example shunting device with a ramp element, in accordance with embodiments of the present disclosure.
Figure 20B:
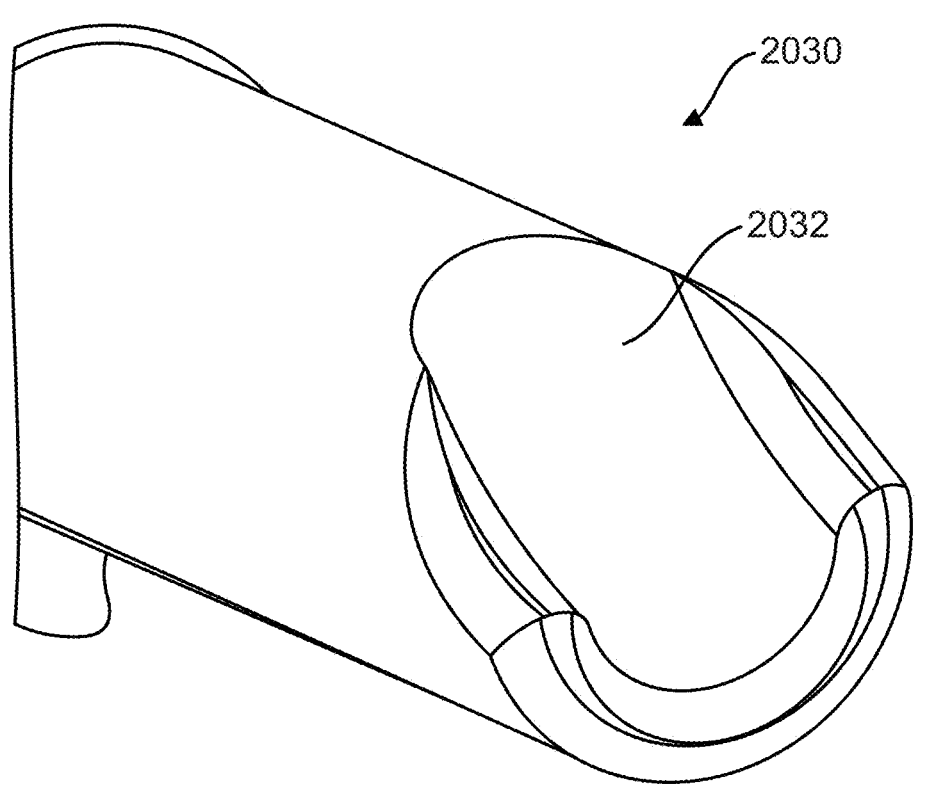
Figure 20C:
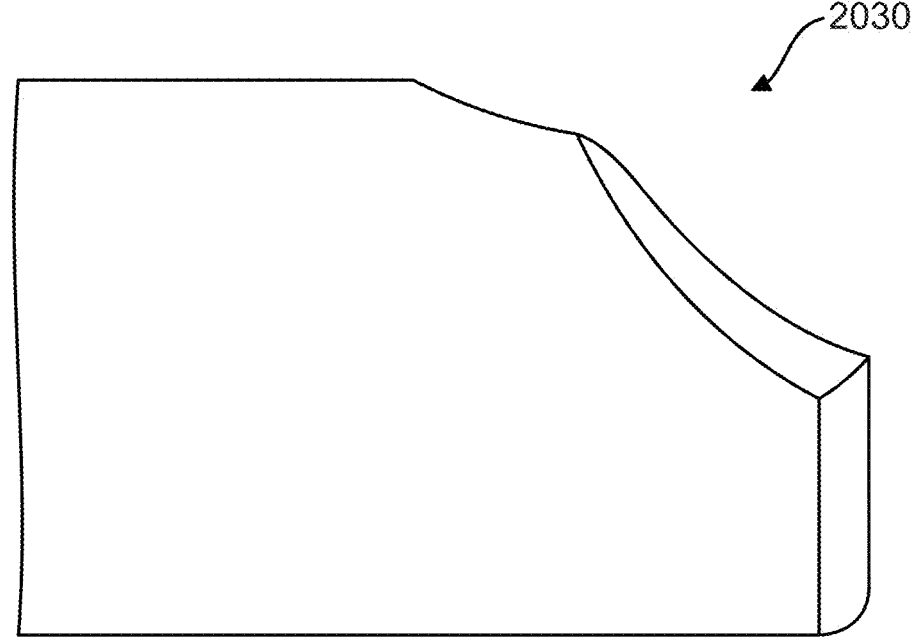

FIGS. 20A-20C are schematic diagrams of an example shunting device 2000 with a ramp element 2030, in accordance with embodiments of the present disclosure. As shown, in some embodiments, the shunting device 2000 includes a shunting catheter 2004 to be delivered through a patient's coronary sinus (CS), a ramp element 2030, a puncture element 2002, and an expandable element sheath 2014.

As discussed above, according to certain embodiments, the shunting catheter 2004 includes a catheter shaft, and a shaft lumen. According to certain embodiments, the puncture element 2002 and the expandable element sheath 2014 are disposed in the shaft lumen of the shunting catheter 2004 at a first state. In certain embodiments, the expandable element sheath 2014 has a pre-determined curve to assist with deployment of the puncture element 2002. In certain embodiments, the puncture element 2002 and the expandable element sheath 2014 are extended from the shaft lumen of the catheter shaft at a second state (e.g., a puncturing state to puncture through a tissue wall of a patient) and/or a third state (e.g., a shunting state to use a shunting element). In some embodiments, the puncture element 2002 is extended from the catheter shaft of shunting catheter 2004 through opening 2005 at the second state. In some examples, the pre-determined curve of the expandable element sheath 2014 may assist the puncture element 2002 in puncturing through a tissue wall of a patient by angling the puncture element 2002 towards a tissue wall of the patient as the puncture element 2002 extends out of catheter 2004 to the second state.

As shown, in some embodiments, the shunting device 2000 includes the ramp element 2030. The ramp element 2030 may be configured to assist with deployment of the puncture element 2002 from the first state to the second state. In some examples, the ramp element 2030 may be disposed inside the lumen of shunting catheter 2004 on a distal side of opening 2005. The ramp element 2030 may be fixed within the shunting catheter 2004 (e.g., via glue, or mechanically fixed with a pin, latch, or other locking mechanism) and may be machined or molded out of any material (e.g., metals, plastics, etc.). In some examples, the ramp element 2030 may be injection molded (e.g., molded as a part of the shunting catheter, for example, shunting catheter 202, 302, 400). In some examples, the ramp element 2030 is formed of a material with a low friction between the material of the puncture element 2002 and the material of the expandable element sheath 2014.

The ramp element 2030 may include curved feature 2032 to assist with transition of the puncture element 2002 and expandable element sheath 2014 from the first state within the lumen of shunting catheter 2004 to the second state extending from shunting catheter 2004. In some embodiments, the curved feature 2032 of the ramp element 2030 is configured to assist with curving the expandable element sheath 2014 when transitioning from a first state to a second state. In certain embodiments, the curved feature 2032 of the ramp element 2030 is configured to provide support and/or help direct the puncture element 2002 when puncturing a tissue wall. As puncture element 2002 and expandable element sheath 2014 are transited distally through the shunting catheter 2004, the puncture element 2002 may slide along the curved feature 2032, which redirects the puncture element 2002 out of the shunting catheter 2004 through the opening 2005 and towards patient tissue. In some embodiments, as shown, the curved feature 2032 may define a smooth curve with a fixed or variable radius from a generally longitudinal direction of the shunting catheter 2004 to a generally perpendicular direction to said longitudinal direction. The smooth curvature of the curved feature 2032 helps reduce friction between the materials when extending expandable element sheath 2014 from the catheter shaft of the shunting catheter 2004. Although shown as a smooth curve in FIGS. 20A-20C, in some examples, the curved feature 2032 may include a straight chamfer. In some examples, the curved feature 2032 may be flush with the opening 2005 (e.g., a portion of the track of the curved feature 2032 may be flush with a distal edge portion of the opening 2005).

According to one aspect, a shunting catheter includes a catheter shaft having a distal end and a proximal end, the catheter shaft including a shaft lumen; a shunting component including one or more electrodes; and a puncture assembly disposed in the shaft lumen at a first state and extended from the catheter shaft at a second state.

According to another aspect, the puncture assembly includes: a curved puncture element wherein a tip of the curved puncture element defining a first axis and a body of the curved puncture element defining a second axis, wherein the first axis and the second axis form an angle greater than zero degrees.

According to another aspect, the puncture assembly has a diameter approximately same as a diameter of the shunting component at a deployment state.

According to another aspect, a proximal portion of the puncture element defines the first axis, a distal portion of the puncture element defines the second axis, the puncture assembly further includes a hypotube core, a distal portion of the hypotube core defines a longitudinal axis; and the first axis is coincident with the longitudinal axis.

According to another aspect, the first axis and the second axis form an angle between 10 and 90 degrees.

According to another aspect, the curve of the puncture element biases the puncture element towards a tissue wall during a shunting procedure.

According to another aspect, the puncture element includes a blade section including two flat surfaces, and a tip defining a distal point of the puncture element; wherein an intersection of the two flat surfaces defines a blade edge; wherein the blade edge defines a first end, a second end, and a line that is angled with respect to an axis defined by the puncture element; wherein the tip includes a first end of the blade edge.

According to another aspect, the blade section has a tapered shape.

According to another aspect, the blade section includes a curved surface surrounding the two flat surfaces.

According to another aspect, the puncture assembly further includes a dilator defining a longitudinal axis, a portion of the dilator furthest away from the longitudinal axis defines a first distance from the longitudinal axis, a portion of the puncture element furthest away from the longitudinal axis defines a second distance, and the second distance is less than or equal to the first distance.

According to another aspect, the puncture element includes a plurality of blade edges; and a tip defining a distal point of the puncture element, wherein the tip includes a first end of each of the plurality of blade edges.

According to another aspect, the plurality of blade edges defines a plurality of blade lengths, and wherein each of the plurality of blade lengths are the same.

According to another aspect, the plurality of blade edges defines a plurality of blade lengths, and one or more of the plurality of blade lengths are different.

According to another aspect, the curve of the puncture element defines a smooth transition between the first axis and the second axis.

According to another aspect, the curve of the puncture element defines an abrupt pivot between the first axis and the second axis.

According to another aspect, the puncture element defines a conical shape, and wherein a distal tip of the puncture element is a tip of the conical shape.

According to another aspect, the distal tip defines a radius of 0.0254 to 0.762 millimeters.

According to another aspect, the puncture element is formed in the shape of an arrowhead including four protruding leaves.

According to another aspect, the puncture assembly further includes a dilator including a frustoconical distal portion and a frustoconical proximal portion, and the frustoconical distal portion is connected to the frustoconical proximal portion at a joint surface defining a largest diameter of the dilator.

According to another aspect, the dilator is formed as a proximal portion of the puncture element.

According to another aspect, the puncture element is formed of a conductive material configured to transmit ablation energy to tissue of a patient, the puncture assembly further includes an expandable element sheath, and the dilator is configured to insulate the expandable element sheath from the puncture element.

According to another aspect, the puncture assembly further includes a hypotube core and a puncture element, and the hypotube core and the puncture element are formed of a conductive material configured to transmit ablation energy from a proximal end of the shunting catheter to the puncture element.

According to another aspect, the puncture assembly includes an expandable element sheath disposed within the shaft lumen at the first state, and a distal portion of the expandable element sheath is curved to facilitate directing the puncture assembly towards a tissue wall in the second state during a shunting procedure.

According to another aspect, the shunting component further includes an expandable element deposited within an expandable element sheath and connected to an outer surface of an expandable element inner sheath; a puncture element connected to a puncture shaft deposited within the expandable element inner sheath; and a dilator connected to a distal end of the expandable element inner sheath; wherein the expandable element inner sheath is configured to translate along the puncture shaft together with the expandable element and the dilator.

According to one aspect, a shunting catheter includes a catheter shaft having a distal end and a proximal end, the catheter shaft including a shaft lumen; and a puncture assembly disposed in the shaft lumen at a first state and extended from the catheter shaft at a second state. In some embodiments, the puncture assembly includes: a puncture element defining a longitudinal axis and including: a blade section including: a blade edge defining a first end, a second end, and a line following the blade edge, wherein the line and the longitudinal axis form an angle greater than zero degrees; and a tip defining a distal point of the puncture element, wherein the tip includes a first end of the blade edge.

According to another aspect, the line following the blade edge and the longitudinal axis form an angle between 10 and 90 degrees.

According to one aspect, a shunting catheter includes a catheter shaft having a distal end and a proximal end, the catheter shaft including a shaft lumen; a shunting component including one or more electrodes; and a puncture assembly disposed in the shaft lumen at a first state and extended from the catheter shaft at a second state; wherein the puncture element defines a conical shape, and wherein a distal tip of the puncture element is a tip of the conical shape.

According to another aspect, the distal tip is a blunted tip defining a radius of 0.0127 to 0.762 millimeters.

According to another aspect, wherein the distal tip is a blunted tip configured to tent a tissue wall at a target location to confirm a location of the distal tip and/or a direction the distal tip is contacting the tissue wall.

According to another aspect, wherein the puncture assembly includes: a curved puncture element wherein a tip of the curved puncture element defining a first axis and a body of the curved puncture element defining a second axis, wherein the first axis and the second axis form an angle greater than zero degrees.

Various modifications and additions can be made to the exemplary embodiments discussed without departing from the scope of the present disclosure. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A shunting catheter, comprising:

a catheter shaft having a distal end and a proximal end, the catheter shaft including a shaft lumen;

a shunting component including one or more electrodes; and a puncture assembly disposed in the shaft lumen at a first state and extended from the catheter shaft at a second state;

wherein the puncture assembly is connected to the shunting component;

a shunting element shaft configured to support the shunting component, the shunting element shaft disposed in the shaft lumen at a first state and extended from the catheter shaft at a second state;

wherein the puncture assembly comprises a puncture element and a dilator portion, the puncture assembly is disposed at a distal end of the shunting element shaft and configured to deliver a first ablation energy to create an opening at the second state;

wherein at the second state:

the shunting element shaft includes a curved portion and a straight portion when the shunting element shaft extends out of the catheter shaft;

the puncture assembly is disposed proximate to the straight portion of the shunting element shaft;

a tip of the puncture element defines a first axis;

the straight portion of the shunting element shaft defines a second axis;

the first axis and the second axis form an angle greater than zero degrees; and the dilator portion is disposed between the tip of the puncture element and the shunting component supported by the straight portion of the shunting element shaft;

wherein the shunting component is configured to extend from the catheter shaft at a third state;

wherein the one or more electrodes are configured to deliver a second ablation energy to enlarge the opening at the third state after delivery of the first ablation energy;

wherein the second state is different from the third state.

2. The shunting catheter of claim 1, wherein the puncture element comprises the tip extending along the first axis and a curved body coupled to the dilator portion.

3. The shunting catheter of claim 2, wherein the curved body of the puncture element biases the puncture element towards a tissue wall during a shunting procedure.

4. The shunting catheter of claim 2, wherein the curve of the puncture element defines a smooth transition between the first axis and the second axis.

5. The shunting catheter of claim 1, wherein the puncture assembly has a diameter approximately same as a diameter of the shunting component at a deployment state.

6. The shunting catheter of claim 1, wherein the puncture assembly further comprises a hypotube core.

7. The shunting catheter of claim 1, wherein the first axis and the second axis form an angle between 10 and 90 degrees.

8. The shunting catheter of claim 1, wherein the dilator portion has a proximal end and a distal end;

wherein the proximal end of the dilator portion has a proximal diameter;

wherein the distal end of the dilator portion has a distal diameter;

wherein the proximal diameter is greater than the distal diameter.

9. The shunting catheter of claim 1, wherein the puncture element defines a conical shape, and wherein the tip of the puncture element is a tip of the conical shape.

10. The shunting catheter of claim 1, wherein the tip of the puncture element has a radius of 0.0254 to 0.762 millimeters.

11. The shunting catheter of claim 1, wherein the puncture assembly extends from the shunting component at a distal end of the shunting component;

wherein the dilator portion of the puncture assembly includes a frustoconical distal portion and a frustoconical proximal portion;

wherein the frustoconical proximal portion has an increasing diameter further away from the distal end of the shunting component;

wherein the frustoconical distal portion has a decreasing diameter further away from the distal end of the shunting component.

12. The shunting catheter of claim 11, wherein the dilator portion is formed as a proximal portion of the puncture element.

13. The shunting catheter of claim 11, wherein the puncture assembly further comprises an expandable element sheath.

14. The shunting catheter of claim 1, wherein the puncture assembly further comprises a hypotube core, wherein the hypotube core is formed of a conductive material configured to transmit ablation energy from a proximal end of the shunting catheter to the puncture element.

15. The shunting catheter of claim 1, wherein the puncture assembly comprises an expandable element sheath disposed within the shaft lumen at the first state, and wherein a distal portion of the expandable element sheath is curved to facilitate directing the puncture assembly towards a tissue wall in the second state during a shunting procedure.

16. The shunting catheter of claim 1, wherein the shunting component further comprises:

an expandable element deposited within an expandable element sheath and connected to an outer surface of an expandable element inner sheath; and wherein the dilator portion is connected to a distal end of the expandable element inner sheath;

wherein the puncture element is connected to a puncture shaft deposited within the expandable element inner sheath;

wherein the expandable element inner sheath is configured to translate along the puncture shaft together with the expandable element and the dilator.

17. The shunting catheter of claim 1, wherein the dilator portion is connected to the puncture element at a distal end of the dilator portion;

wherein the puncture element has a rounded tip.

18. The shunting catheter of claim 1, wherein the dilator portion includes an anchor element to anchor the dilator portion with respect to the puncture element.

19. A shunting catheter, comprising:

a catheter shaft having a distal end and a proximal end, the catheter shaft including a shaft lumen;

a shunting component including one or more electrodes; and a puncture assembly disposed in the shaft lumen at a first state and extended from the catheter shaft at a second state;

wherein the puncture assembly is connected to the shunting component;

wherein the puncture assembly comprises a puncture element, the puncture element configured to deliver a first ablation energy to create an opening at the second state;

wherein the puncture element has a conical shape;

wherein a distal tip of the puncture element is a tip of the conical shape;

wherein the puncture assembly comprises a dilator portion disposed between the distal tip of the puncture element and the shunting component;

wherein an anchoring element disposed within the dilator portion to anchor the dilator portion with respect to the puncture element;

wherein the shunting component is configured to extend from the catheter shaft at a third state;

wherein the one or more electrodes are configured to deliver a second ablation energy to enlarge the opening at the third state after delivery of the first ablation energy;

wherein the second state is different from the third state.

20. The shunting catheter of claim 19, wherein the distal tip is a blunted tip defining a radius of 0.0127 to 0.762 millimeters.

21. The shunting catheter of claim 19, wherein the distal tip is a blunted tip configured to tent a tissue wall at a target location to confirm a location of the distal tip and/or a direction the distal tip is contacting the tissue wall.

\*  \*  \*  \*  \*